United States Patent
Jiang et al.

(10) Patent No.: US 9,561,372 B2
(45) Date of Patent: Feb. 7, 2017

(54) ELECTROMYOGRAPHIC LEAD POSITIONING AND STIMULATION TITRATION IN A NERVE STIMULATION SYSTEM FOR TREATMENT OF OVERACTIVE BLADDER

(71) Applicant: Axonics Modulation Technologies, Inc., Irvine, CA (US)

(72) Inventors: Guangqiang Jiang, Irvine, CA (US); John Woock, Costa Mesa, CA (US); Dennis Schroeder, Irvine, CA (US); Eric Schmid, Irvine, CA (US)

(73) Assignee: AXONICS MODULATION TECHNOLOGIES, INC., Irvine, CA (US)

( * ) Notice: Subject to any disclaimer, the term of this patent is extended or adjusted under 35 U.S.C. 154(b) by 0 days.

(21) Appl. No.: 14/991,752

(22) Filed: Jan. 8, 2016

(65) Prior Publication Data
US 2016/0121123 A1    May 5, 2016

Related U.S. Application Data

(63) Continuation of application No. 14/827,108, filed on Aug. 14, 2015.

(51) Int. Cl.
*A61N 1/36* (2006.01)
*A61N 1/372* (2006.01)
*A61N 1/05* (2006.01)

(52) U.S. Cl.
CPC ....... *A61N 1/36135* (2013.01); *A61N 1/36007* (2013.01); *A61N 1/36017* (2013.01);
(Continued)

(58) Field of Classification Search
CPC ................... A61N 1/0551; A61N 1/36007
See application file for complete search history.

(56) References Cited

U.S. PATENT DOCUMENTS 3,646,940 A    3/1972    Timm et al.
4,019,518 A    4/1977    Maurer et al.
(Continued)

FOREIGN PATENT DOCUMENTS

EP    1680182 A1    7/2006
EP    1680182 B1    7/2006
(Continued)

OTHER PUBLICATIONS

Bosch, J., et al., Sacral (S3) Segmental Nerve Stimulation as a Treatment for Urge Incontinence in Patients With Detrusor Instability: Results of Chronic Electrical Stimulation Using an Implantable Neural Prosthesis, The Journal of Urology, Aug. 1995, vol. 154, pp. 504-507.

(Continued)

*Primary Examiner* — William Levicky
(74) *Attorney, Agent, or Firm* — Kilpatrick Townsend & Stockton LLP; Kenneth R. Shurtz, Esq.

(57) ABSTRACT

The present invention provides improved methods for positioning of an implantable lead in a patient with an integrated EMG and stimulation clinician programmer. The integrated clinician programmer is coupled to the implantable lead, wherein the implantable lead comprises at least four electrodes, and to at least one EMG sensing electrode minimally invasively positioned on a skin surface or within the patient. The method comprises delivering a test stimulation at a stimulation amplitude level from the integrated clinician programmer to a nerve tissue of the patient with a principal electrode of the implantable lead. Test stimulations are delivered at a same stimulation amplitude level for a same period of time sequentially to each of the four electrodes of (Continued)

the implantable lead. A stimulation-induced EMG motor response is recorded with the integrated clinician programmer for each test stimulation on each electrode of the implantable lead via the at least one pair of EMG sensing electrodes so as to facilitate initial positioning of the implantable lead at a target stimulation region.

30 Claims, 43 Drawing Sheets

Related U.S. Application Data

(60) Provisional application No. 62/038,131, filed on Aug. 15, 2014, provisional application No. 62/041,611, filed on Aug. 25, 2014, provisional application No. 62/101,888, filed on Jan. 9, 2015.

(52) U.S. Cl.
CPC ..... *A61N 1/37241* (2013.01); *A61N 1/37247* (2013.01); *A61N 1/0551* (2013.01); *A61N 1/36107* (2013.01); *A61N 1/36157* (2013.01); *A61N 1/36185* (2013.01)

(56) References Cited

U.S. PATENT DOCUMENTS

| | | |
|---|---|---|
| 4,044,774 A | 8/1977 | Corbin et al. |
| 4,210,383 A | 7/1980 | Davis |
| 4,340,062 A | 7/1982 | Thompson et al. |
| 4,558,702 A | 12/1985 | Barreras et al. |
| 4,744,371 A | 5/1988 | Harris |
| 5,690,693 A | 11/1997 | Wang et al. |
| 5,702,428 A | 12/1997 | Tippey et al. |
| 5,702,431 A | 12/1997 | Wang et al. |
| 5,735,887 A | 4/1998 | Barreras, Sr. et al. |
| 5,741,316 A | 4/1998 | Chen et al. |
| 5,876,423 A | 3/1999 | Braun |
| 6,014,588 A | 1/2000 | Fitz |
| 6,027,456 A | 2/2000 | Feler et al. |
| 6,035,237 A | 3/2000 | Schulman et al. |
| 6,052,624 A | 4/2000 | Mann |
| 6,055,456 A | 4/2000 | Gerber |
| 6,057,513 A | 5/2000 | Ushikoshi et al. |
| 6,067,474 A | 5/2000 | Schulman et al. |
| 6,076,017 A | 6/2000 | Taylor et al. |
| 6,172,556 B1 | 1/2001 | Prentice |
| 6,178,353 B1 | 1/2001 | Griffith et al. |
| 6,181,961 B1 | 1/2001 | Prass |
| 6,191,365 B1 | 2/2001 | Avellanet |
| 6,208,894 B1 | 3/2001 | Schulman et al. |
| 6,212,431 B1 | 4/2001 | Hahn et al. |
| 6,221,513 B1 | 4/2001 | Lasater |
| 6,246,911 B1 | 6/2001 | Seligman |
| 6,249,703 B1 | 6/2001 | Stanton et al. |
| 6,265,789 B1 | 7/2001 | Honda et al. |
| 6,306,100 B1 | 10/2001 | Prass |
| 6,314,325 B1 | 11/2001 | Fitz |
| 6,315,721 B2 | 11/2001 | Schulman et al. |
| 6,324,432 B1 | 11/2001 | Rigaux et al. |
| 6,354,991 B1 | 3/2002 | Gross et al. |
| 6,360,750 B1 | 3/2002 | Gerber et al. |
| 6,393,325 B1 | 5/2002 | Mann et al. |
| 6,438,423 B1 | 8/2002 | Rezai et al. |
| 6,442,434 B1 | 8/2002 | Zarinetchi et al. |
| 6,466,817 B1 | 10/2002 | Kaula et al. |
| 6,505,075 B1 | 1/2003 | Weiner |
| 6,516,227 B1 | 2/2003 | Meadows et al. |
| 6,584,355 B2 | 6/2003 | Stessman |
| 6,587,728 B2 | 7/2003 | Fang et al. |
| 6,600,954 B2 | 7/2003 | Cohen et al. |
| 6,609,031 B1 | 8/2003 | Law et al. |
| 6,609,032 B1 | 8/2003 | Woods et al. |
| 6,625,494 B2 | 9/2003 | Fang et al. |
| 6,652,449 B1 | 11/2003 | Gross et al. |
| 6,654,634 B1 | 11/2003 | Prass |
| 6,662,051 B1 | 12/2003 | Eraker et al. |
| 6,662,053 B2 | 12/2003 | Borkan |
| 6,678,563 B2 | 1/2004 | Fang et al. |
| 6,701,189 B2 | 3/2004 | Fang et al. |
| 6,721,603 B2 | 4/2004 | Zabara et al. |
| 6,735,474 B1 | 5/2004 | Loeb et al. |
| 6,745,077 B1 | 6/2004 | Griffith et al. |
| 6,809,701 B2 | 10/2004 | Amundson et al. |
| 6,836,684 B1 | 12/2004 | Rijkhoff et al. |
| 6,836,685 B1 | 12/2004 | Fitz |
| 6,847,849 B2 | 1/2005 | Mamo et al. |
| 6,871,099 B1 | 3/2005 | Whitehurst et al. |
| 6,892,098 B2 | 5/2005 | Ayal et al. |
| 6,895,280 B2 | 5/2005 | Meadows et al. |
| 6,896,651 B2 | 5/2005 | Gross et al. |
| 6,901,287 B2 | 5/2005 | Davis et al. |
| 6,907,293 B2 | 6/2005 | Grill et al. |
| 6,923,814 B1 | 8/2005 | Hildebrand et al. |
| 6,941,171 B2 | 9/2005 | Mann et al. |
| 6,959,215 B2 | 10/2005 | Gliner et al. |
| 6,971,393 B1 | 12/2005 | Mamo et al. |
| 6,989,200 B2 | 1/2006 | Byers et al. |
| 6,990,376 B2 | 1/2006 | Tanagho et al. |
| 6,999,819 B2 | 2/2006 | Swoyer et al. |
| 7,010,351 B2 | 3/2006 | Firlik et al. |
| 7,024,247 B2 | 4/2006 | Gliner et al. |
| 7,047,078 B2 | 5/2006 | Boggs, II et al. |
| 7,051,419 B2 | 5/2006 | Schrom et al. |
| 7,054,689 B1 | 5/2006 | Whitehurst et al. |
| 7,069,081 B2 | 6/2006 | Biggs et al. |
| 7,127,298 B1 | 10/2006 | He et al. |
| 7,142,925 B1 | 11/2006 | Bhadra et al. |
| 7,146,217 B2 | 12/2006 | Firlik et al. |
| 7,146,219 B2 | 12/2006 | Sieracki et al. |
| 7,151,914 B2 | 12/2006 | Brewer |
| 7,167,743 B2 | 1/2007 | Heruth et al. |
| 7,167,749 B2 | 1/2007 | Biggs et al. |
| 7,177,677 B2 | 2/2007 | Kaula et al. |
| 7,177,690 B2 | 2/2007 | Woods et al. |
| 7,177,698 B2 | 2/2007 | Klosterman et al. |
| 7,181,286 B2 | 2/2007 | Sieracki et al. |
| 7,187,978 B2 | 3/2007 | Malek et al. |
| 7,191,005 B2 | 3/2007 | Stessman |
| 7,212,110 B1 | 5/2007 | Martin et al. |
| 7,214,197 B2 | 5/2007 | Prass |
| 7,225,032 B2 | 5/2007 | Schmeling et al. |
| 7,231,254 B2 | 6/2007 | DiLorenzo |
| 7,234,853 B2 | 6/2007 | Givoletti |
| 7,236,831 B2 | 6/2007 | Firlik et al. |
| 7,245,972 B2 | 7/2007 | Davis |
| 7,283,867 B2 | 10/2007 | Strother et al. |
| 7,286,880 B2 | 10/2007 | Olson et al. |
| 7,299,096 B2 | 11/2007 | Balzer et al. |
| 7,305,268 B2 | 12/2007 | Gliner et al. |
| 7,317,948 B1 | 1/2008 | King et al. |
| 7,324,852 B2 | 1/2008 | Barolat et al. |
| 7,324,853 B2 | 1/2008 | Ayal et al. |
| 7,326,181 B2 | 2/2008 | Katims |
| 7,328,068 B2 | 2/2008 | Spinelli et al. |
| 7,330,764 B2 | 2/2008 | Swoyer et al. |
| 7,337,006 B2 | 2/2008 | Kim et al. |
| 7,359,751 B1 | 4/2008 | Erickson et al. |
| 7,369,894 B2 | 5/2008 | Gerber |
| 7,386,348 B2 | 6/2008 | North et al. |
| 7,387,603 B2 | 6/2008 | Gross et al. |
| 7,395,113 B2 | 7/2008 | Heruth et al. |
| 7,396,265 B2 | 7/2008 | Darley et al. |
| 7,406,351 B2 | 7/2008 | Wesselink |
| 7,415,308 B2 | 8/2008 | Gerber et al. |
| 7,444,181 B2 | 10/2008 | Shi et al. |
| 7,447,546 B2 | 11/2008 | Kim et al. |
| 7,450,991 B2 | 11/2008 | Smith et al. |
| 7,450,993 B2 | 11/2008 | Kim et al. |
| 7,460,911 B2 | 12/2008 | Cosendai et al. |
| 7,463,928 B2 | 12/2008 | Lee et al. |
| 7,470,236 B1 | 12/2008 | Kelleher et al. |

(56) References Cited

U.S. PATENT DOCUMENTS

| | | |
|---|---|---|
| 7,483,747 B2 | 1/2009 | Gliner et al. |
| 7,483,752 B2 | 1/2009 | Von Arx et al. |
| 7,496,404 B2 | 2/2009 | Meadows et al. |
| 7,502,651 B2 | 3/2009 | Kim et al. |
| 7,515,965 B2 | 4/2009 | Gerber et al. |
| 7,515,967 B2 | 4/2009 | Phillips et al. |
| 7,522,953 B2 | 4/2009 | Kaula et al. |
| 7,532,936 B2 | 5/2009 | Erickson et al. |
| 7,539,538 B2 | 5/2009 | Parramon et al. |
| 7,551,958 B2 | 6/2009 | Libbus et al. |
| 7,551,960 B2 | 6/2009 | Forsberg et al. |
| 7,555,346 B1 | 6/2009 | Woods et al. |
| 7,555,347 B2 | 6/2009 | Loeb |
| 7,565,199 B2 | 7/2009 | Sheffield et al. |
| 7,565,203 B2 | 7/2009 | Greenberg et al. |
| 7,571,000 B2 | 8/2009 | Boggs, II et al. |
| 7,577,481 B2 | 8/2009 | Firlik et al. |
| 7,578,819 B2 | 8/2009 | Bleich et al. |
| 7,580,752 B2 | 8/2009 | Gerber et al. |
| 7,580,753 B2 | 8/2009 | Kim et al. |
| 7,582,053 B2 | 9/2009 | Gross et al. |
| 7,582,058 B1 | 9/2009 | Miles et al. |
| 7,613,516 B2 | 11/2009 | Cohen et al. |
| 7,617,002 B2 | 11/2009 | Goetz |
| 7,620,456 B2 | 11/2009 | Gliner et al. |
| 7,623,925 B2 | 11/2009 | Grill et al. |
| 7,636,602 B2 | 12/2009 | Baru Fassio et al. |
| 7,640,059 B2 | 12/2009 | Forsberg et al. |
| 7,643,880 B2 | 1/2010 | Tanagho et al. |
| 7,664,544 B2 | 2/2010 | Miles et al. |
| 7,672,730 B2 | 3/2010 | Firlik et al. |
| 7,706,889 B2 | 4/2010 | Gerber et al. |
| 7,720,547 B2 | 5/2010 | Denker et al. |
| 7,720,548 B2 | 5/2010 | King |
| 7,725,191 B2 | 5/2010 | Greenberg et al. |
| 7,734,355 B2 | 6/2010 | Cohen et al. |
| 7,738,963 B2 | 6/2010 | Hickman et al. |
| 7,738,965 B2 | 6/2010 | Phillips et al. |
| 7,747,330 B2 | 6/2010 | Nolan et al. |
| 7,756,584 B2 | 7/2010 | Sheffield et al. |
| 7,771,838 B1 | 8/2010 | He et al. |
| 7,774,069 B2 | 8/2010 | Olson et al. |
| 7,801,601 B2 | 9/2010 | Maschino et al. |
| 7,801,619 B2 | 9/2010 | Gerber et al. |
| 7,805,196 B2 | 9/2010 | Miesel et al. |
| 7,813,803 B2 | 10/2010 | Heruth et al. |
| 7,813,809 B2 | 10/2010 | Strother et al. |
| 7,819,909 B2 | 10/2010 | Goetz et al. |
| 7,826,901 B2 | 11/2010 | Lee et al. |
| 7,831,305 B2 | 11/2010 | Gliner |
| 7,848,818 B2 | 12/2010 | Barolat et al. |
| 7,853,322 B2 | 12/2010 | Bourget et al. |
| 7,890,176 B2 | 2/2011 | Jaax et al. |
| 7,904,167 B2 | 3/2011 | Klosterman et al. |
| 7,912,555 B2 | 3/2011 | Swoyer et al. |
| 7,925,357 B2 | 4/2011 | Phillips et al. |
| 7,932,696 B2 | 4/2011 | Peterson |
| 7,933,656 B2 | 4/2011 | Sieracki et al. |
| 7,935,051 B2 | 5/2011 | Miles et al. |
| 7,937,158 B2 | 5/2011 | Erickson et al. |
| 7,945,330 B2 | 5/2011 | Gliner et al. |
| 7,952,349 B2 | 5/2011 | Huang et al. |
| 7,957,797 B2 | 6/2011 | Bourget et al. |
| 7,957,809 B2 | 6/2011 | Bourget et al. |
| 7,957,818 B2 | 6/2011 | Swoyer |
| 7,962,218 B2 | 6/2011 | Balzer et al. |
| 7,966,073 B2 | 6/2011 | Pless et al. |
| 7,979,119 B2 | 7/2011 | Kothandaraman et al. |
| 7,979,126 B2 | 7/2011 | Payne et al. |
| 7,981,144 B2 | 7/2011 | Geist et al. |
| 7,988,507 B2 | 8/2011 | Darley et al. |
| 8,000,782 B2 | 8/2011 | Gharib et al. |
| 8,000,805 B2 | 8/2011 | Swoyer et al. |
| 8,005,535 B2 | 8/2011 | Gharib et al. |
| 8,005,549 B2 | 8/2011 | Boser et al. |
| 8,005,550 B2 | 8/2011 | Boser et al. |
| 8,019,423 B2 | 9/2011 | Possover |
| 8,019,425 B2 | 9/2011 | Firlik et al. |
| 8,024,047 B2 | 9/2011 | Olson et al. |
| 8,027,716 B2 | 9/2011 | Gharib et al. |
| 8,036,756 B2 | 10/2011 | Swoyer et al. |
| 8,044,635 B2 | 10/2011 | Peterson |
| 8,050,753 B2 | 11/2011 | Libbus et al. |
| 8,050,767 B2 | 11/2011 | Sheffield et al. |
| 8,050,768 B2 | 11/2011 | Firlik et al. |
| 8,050,769 B2 | 11/2011 | Gharib et al. |
| 8,055,337 B2 | 11/2011 | Moffitt et al. |
| 8,055,349 B2 | 11/2011 | Gharib et al. |
| 8,065,012 B2 | 11/2011 | Firlik et al. |
| 8,068,912 B2 | 11/2011 | Kaula et al. |
| 8,073,546 B2 | 12/2011 | Sheffield et al. |
| 8,082,039 B2 | 12/2011 | Kim et al. |
| 8,083,663 B2 | 12/2011 | Gross et al. |
| 8,103,360 B2 | 1/2012 | Foster |
| 8,108,049 B2 | 1/2012 | King |
| 8,112,155 B2 | 2/2012 | Einav et al. |
| 8,116,862 B2 | 2/2012 | Stevenson et al. |
| 8,121,701 B2 | 2/2012 | Woods et al. |
| 8,121,702 B2 | 2/2012 | King |
| 8,129,942 B2 | 3/2012 | Park et al. |
| 8,131,358 B2 | 3/2012 | Moffitt et al. |
| 8,140,168 B2 | 3/2012 | Olson et al. |
| 8,145,324 B1 | 3/2012 | Stevenson et al. |
| 8,147,421 B2 | 4/2012 | Farquhar et al. |
| 8,150,530 B2 | 4/2012 | Wesselink |
| 8,155,753 B2 | 4/2012 | Wesselink |
| 8,175,717 B2 | 5/2012 | Haller et al. |
| 8,180,451 B2 | 5/2012 | Hickman et al. |
| 8,180,452 B2 | 5/2012 | Shaquer |
| 8,180,461 B2 | 5/2012 | Mamo et al. |
| 8,182,423 B2 | 5/2012 | Miles et al. |
| 8,190,262 B2 | 5/2012 | Gerber et al. |
| 8,195,300 B2 | 6/2012 | Gliner et al. |
| 8,214,042 B2 | 7/2012 | Ozawa et al. |
| 8,214,048 B1 | 7/2012 | Whitehurst et al. |
| 8,214,051 B2 | 7/2012 | Sieracki et al. |
| 8,219,196 B2 | 7/2012 | Torgerson |
| 8,219,202 B2 | 7/2012 | Giftakis et al. |
| 8,224,452 B2 | 7/2012 | Pless et al. |
| 8,229,565 B2 | 7/2012 | Kim et al. |
| 8,233,990 B2 | 7/2012 | Goetz |
| 8,255,057 B2 | 8/2012 | Fang et al. |
| 8,311,636 B2 | 11/2012 | Gerber et al. |
| 8,314,594 B2 | 11/2012 | Scott et al. |
| 8,326,433 B2 | 12/2012 | Blum et al. |
| 8,332,040 B1 | 12/2012 | Winstrom |
| 8,337,410 B2 | 12/2012 | Kelleher et al. |
| 8,340,786 B2 | 12/2012 | Gross et al. |
| 8,362,742 B2 | 1/2013 | Kallmyer |
| 8,369,943 B2 | 2/2013 | Shuros et al. |
| 8,380,314 B2 | 2/2013 | Panken et al. |
| 8,386,048 B2 | 2/2013 | McClure et al. |
| 8,391,972 B2 | 3/2013 | Libbus et al. |
| 8,396,555 B2 | 3/2013 | Boggs, II et al. |
| 8,412,335 B2 | 4/2013 | Gliner et al. |
| 8,417,346 B2 | 4/2013 | Giftakis et al. |
| 8,423,145 B2 | 4/2013 | Pless et al. |
| 8,423,146 B2 | 4/2013 | Giftakis et al. |
| 8,430,805 B2 | 4/2013 | Burnett et al. |
| 8,433,414 B2 | 4/2013 | Gliner et al. |
| 8,435,166 B2 | 5/2013 | Burnett et al. |
| 8,447,402 B1 | 5/2013 | Jiang et al. |
| 8,447,408 B2 | 5/2013 | North et al. |
| 8,457,756 B2 | 6/2013 | Rahman |
| 8,457,758 B2 | 6/2013 | Olson et al. |
| 8,480,437 B2 | 7/2013 | Dilmaghanian et al. |
| 8,483,839 B2 | 7/2013 | Wesselink |
| 8,494,625 B2 | 7/2013 | Hargrove |
| 8,509,919 B2 | 8/2013 | Yoo et al. |
| 8,515,545 B2 | 8/2013 | Trier |
| 8,538,530 B1 | 9/2013 | Orinski |
| 8,543,223 B2 | 9/2013 | Sage et al. |
| 8,549,015 B2 | 10/2013 | Barolat |
| 8,554,322 B2 | 10/2013 | Olson et al. |

(56) References Cited

U.S. PATENT DOCUMENTS

| | | |
|---|---|---|
| 8,555,894 B2 | 10/2013 | Schulman et al. |
| 8,562,539 B2 | 10/2013 | Marino |
| 8,571,677 B2 | 10/2013 | Torgerson et al. |
| 8,577,474 B2 | 11/2013 | Rahman et al. |
| 8,588,917 B2 | 11/2013 | Whitehurst et al. |
| 8,626,314 B2 | 1/2014 | Swoyer et al. |
| 8,634,904 B2 | 1/2014 | Kaula et al. |
| 8,634,932 B1 | 1/2014 | Ye et al. |
| 8,644,931 B2 | 2/2014 | Stadler et al. |
| 8,644,933 B2 | 2/2014 | Ozawa et al. |
| 8,655,451 B2 | 2/2014 | Klosterman et al. |
| 8,672,840 B2 | 3/2014 | Miles et al. |
| 8,694,115 B2 | 4/2014 | Goetz et al. |
| 8,700,175 B2 | 4/2014 | Fell |
| 8,712,546 B2 | 4/2014 | Kim et al. |
| 8,725,269 B2 | 5/2014 | Nolan et al. |
| 8,731,656 B2 | 5/2014 | Bourget et al. |
| 8,738,141 B2 | 5/2014 | Smith et al. |
| 8,738,148 B2 | 5/2014 | Olson et al. |
| 8,740,783 B2 | 6/2014 | Gharib et al. |
| 8,744,585 B2 | 6/2014 | Gerber et al. |
| 8,750,985 B2 | 6/2014 | Parramon et al. |
| 8,761,897 B2 | 6/2014 | Kaula et al. |
| 8,768,450 B2 | 7/2014 | Gharib et al. |
| 8,768,452 B2 | 7/2014 | Gerber |
| 8,774,912 B2 | 7/2014 | Gerber |
| 8,805,518 B2 | 8/2014 | King et al. |
| 8,812,116 B2 | 8/2014 | Kaula et al. |
| 8,825,163 B2 | 9/2014 | Grill et al. |
| 8,825,175 B2 | 9/2014 | King |
| 8,831,731 B2 | 9/2014 | Blum et al. |
| 8,831,737 B2 | 9/2014 | Wesselink |
| 8,849,632 B2 | 9/2014 | Sparks et al. |
| 8,855,773 B2 | 10/2014 | Kokones et al. |
| 8,868,199 B2 | 10/2014 | Kaula et al. |
| 8,903,486 B2 | 12/2014 | Bourget et al. |
| 8,918,184 B1 | 12/2014 | Torgerson et al. |
| 8,954,148 B2 | 2/2015 | Labbe et al. |
| 8,989,861 B2 | 3/2015 | Su et al. |
| 9,089,712 B2 | 7/2015 | Joshi et al. |
| 9,108,063 B2 | 8/2015 | Olson et al. |
| 2002/0002390 A1 | 1/2002 | Fischell et al. |
| 2002/0010498 A1 | 1/2002 | Rigaux et al. |
| 2002/0010499 A1 | 1/2002 | Rigaux et al. |
| 2002/0055761 A1 | 5/2002 | Mann et al. |
| 2002/0077572 A1 | 6/2002 | Fang et al. |
| 2002/0169485 A1 | 11/2002 | Pless et al. |
| 2003/0195586 A1 | 10/2003 | Rigaux et al. |
| 2003/0195587 A1 | 10/2003 | Rigaux et al. |
| 2004/0260357 A1 | 12/2004 | Vaughan et al. |
| 2004/0260358 A1 | 12/2004 | Vaughan et al. |
| 2005/0049648 A1 | 3/2005 | Cohen et al. |
| 2005/0104577 A1 | 5/2005 | Matei et al. |
| 2005/0119713 A1 | 6/2005 | Whitehurst et al. |
| 2005/0182454 A1* | 8/2005 | Gharib ............... A61B 5/0488 607/48 |
| 2006/0009816 A1 | 1/2006 | Fang et al. |
| 2006/0142822 A1 | 6/2006 | Tulgar |
| 2006/0206166 A1 | 9/2006 | Weiner |
| 2007/0032834 A1 | 2/2007 | Gliner et al. |
| 2007/0049988 A1 | 3/2007 | Carbunaru et al. |
| 2007/0100388 A1 | 5/2007 | Gerber |
| 2007/0208227 A1 | 9/2007 | Smith et al. |
| 2007/0265675 A1* | 11/2007 | Lund ................. A61N 1/36007 607/41 |
| 2007/0293914 A1 | 12/2007 | Woods et al. |
| 2008/0065178 A1 | 3/2008 | Kelleher et al. |
| 2008/0071191 A1 | 3/2008 | Kelleher et al. |
| 2008/0081958 A1 | 4/2008 | Denison et al. |
| 2008/0167694 A1 | 7/2008 | Bolea et al. |
| 2008/0177348 A1 | 7/2008 | Bolea et al. |
| 2008/0177365 A1 | 7/2008 | Bolea et al. |
| 2008/0183236 A1 | 7/2008 | Gerber |
| 2008/0215112 A1 | 9/2008 | Firlik et al. |
| 2008/0306325 A1 | 12/2008 | Burnett et al. |
| 2009/0018617 A1 | 1/2009 | Skelton et al. |
| 2009/0036946 A1 | 2/2009 | Cohen et al. |
| 2009/0036951 A1 | 2/2009 | Heruth et al. |
| 2009/0048531 A1 | 2/2009 | McGinnis et al. |
| 2009/0054804 A1 | 2/2009 | Gharib et al. |
| 2009/0076565 A1 | 3/2009 | Surwit |
| 2009/0118788 A1 | 5/2009 | Firlik et al. |
| 2009/0157141 A1 | 6/2009 | Chiao et al. |
| 2009/0171381 A1* | 7/2009 | Schmitz ............... A61B 5/0488 606/167 |
| 2009/0204176 A1 | 8/2009 | Miles et al. |
| 2009/0227829 A1 | 9/2009 | Burnett et al. |
| 2009/0287272 A1 | 11/2009 | Kokones et al. |
| 2009/0287273 A1 | 11/2009 | Carlton et al. |
| 2009/0306746 A1 | 12/2009 | Blischak |
| 2010/0023084 A1 | 1/2010 | Gunderson |
| 2010/0076254 A1 | 3/2010 | Jimenez et al. |
| 2010/0076534 A1 | 3/2010 | Mock |
| 2010/0131030 A1 | 5/2010 | Firlik et al. |
| 2010/0145427 A1 | 6/2010 | Gliner et al. |
| 2010/0152808 A1 | 6/2010 | Boggs, II |
| 2010/0152809 A1 | 6/2010 | Boggs, II |
| 2010/0160712 A1 | 6/2010 | Burnett et al. |
| 2010/0168820 A1* | 7/2010 | Maniak ............... A61N 1/37247 607/63 |
| 2010/0204538 A1 | 8/2010 | Burnett et al. |
| 2010/0222629 A1 | 9/2010 | Burnett et al. |
| 2010/0317989 A1 | 12/2010 | Gharib et al. |
| 2011/0004264 A1 | 1/2011 | Siejko et al. |
| 2011/0054562 A1 | 3/2011 | Gliner |
| 2011/0208263 A1 | 8/2011 | Balzer et al. |
| 2011/0238136 A1 | 9/2011 | Bourget et al. |
| 2011/0282416 A1 | 11/2011 | Hamann et al. |
| 2011/0301662 A1* | 12/2011 | Bar-Yoseph ......... A61N 1/0514 607/40 |
| 2011/0301667 A1 | 12/2011 | Olson et al. |
| 2011/0313268 A1 | 12/2011 | Kokones et al. |
| 2012/0022611 A1 | 1/2012 | Firlik et al. |
| 2012/0029382 A1 | 2/2012 | Kelleher et al. |
| 2012/0041512 A1 | 2/2012 | Weiner |
| 2012/0046712 A1 | 2/2012 | Woods et al. |
| 2012/0101537 A1 | 4/2012 | Peterson et al. |
| 2012/0116741 A1 | 5/2012 | Choi et al. |
| 2012/0130448 A1 | 5/2012 | Woods et al. |
| 2012/0136413 A1 | 5/2012 | Bonde et al. |
| 2012/0165899 A1 | 6/2012 | Gliner |
| 2012/0197370 A1 | 8/2012 | Kim et al. |
| 2012/0238893 A1 | 9/2012 | Farquhar et al. |
| 2012/0253422 A1* | 10/2012 | Thacker ............... A61N 1/0551 607/46 |
| 2012/0253442 A1 | 10/2012 | Gliner et al. |
| 2012/0265267 A1 | 10/2012 | Blum et al. |
| 2012/0271376 A1 | 10/2012 | Kokones et al. |
| 2012/0276854 A1 | 11/2012 | Joshi et al. |
| 2012/0276856 A1 | 11/2012 | Joshi et al. |
| 2012/0277839 A1 | 11/2012 | Kramer et al. |
| 2012/0290055 A1* | 11/2012 | Boggs, II ............ A61N 1/36071 607/116 |
| 2012/0296395 A1 | 11/2012 | Hamann et al. |
| 2012/0310299 A1 | 12/2012 | Kaula et al. |
| 2012/0316630 A1 | 12/2012 | Firlik et al. |
| 2013/0004925 A1 | 1/2013 | Labbe et al. |
| 2013/0006330 A1 | 1/2013 | Wilder et al. |
| 2013/0006331 A1 | 1/2013 | Weisgarber et al. |
| 2013/0041430 A1 | 2/2013 | Wang et al. |
| 2013/0072998 A1 | 3/2013 | Su et al. |
| 2013/0079840 A1 | 3/2013 | Su et al. |
| 2013/0123568 A1 | 5/2013 | Hamilton et al. |
| 2013/0131755 A1 | 5/2013 | Panken et al. |
| 2013/0150925 A1 | 6/2013 | Vamos et al. |
| 2013/0165814 A1 | 6/2013 | Kaula et al. |
| 2013/0165991 A1 | 6/2013 | Kim et al. |
| 2013/0178758 A1 | 7/2013 | Kelleher et al. |
| 2013/0197608 A1 | 8/2013 | Eiger |
| 2013/0207863 A1 | 8/2013 | Joshi |
| 2013/0226261 A1 | 8/2013 | Sparks et al. |
| 2013/0245722 A1 | 9/2013 | Ternes et al. |
| 2013/0261684 A1 | 10/2013 | Howard et al. |
| 2013/0289664 A1 | 10/2013 | Johanek et al. |

(56) References Cited

U.S. PATENT DOCUMENTS

| | | |
|---|---|---|
| 2013/0303828 A1 | 11/2013 | Hargrove |
| 2013/0310891 A1 | 11/2013 | Enrooth et al. |
| 2013/0310893 A1 | 11/2013 | Yoo et al. |
| 2013/0310894 A1 | 11/2013 | Trier |
| 2013/0331909 A1 | 12/2013 | Gerber |
| 2014/0062900 A1 | 3/2014 | Kaula et al. |
| 2014/0063003 A1 | 3/2014 | Kaula et al. |
| 2014/0063017 A1 | 3/2014 | Kaula et al. |
| 2014/0067006 A1 | 3/2014 | Kaula et al. |
| 2014/0067014 A1 | 3/2014 | Kaula et al. |
| 2014/0067016 A1 | 3/2014 | Kaula et al. |
| 2014/0067354 A1 | 3/2014 | Kaula et al. |
| 2014/0114385 A1 | 4/2014 | Nijhuis et al. |
| 2014/0142549 A1 | 5/2014 | Su et al. |
| 2014/0148870 A1 | 5/2014 | Burnett |
| 2014/0163579 A1 | 6/2014 | Tischendorf et al. |
| 2014/0163580 A1 | 6/2014 | Tischendorf et al. |
| 2014/0163644 A1 | 6/2014 | Scott et al. |
| 2014/0180363 A1* | 6/2014 | Zhu .................. A61N 1/37252 607/59 |
| 2014/0194771 A1 | 7/2014 | Parker et al. |
| 2014/0194772 A1 | 7/2014 | Single et al. |
| 2014/0194942 A1 | 7/2014 | Sathaye et al. |
| 2014/0222112 A1 | 8/2014 | Fell |
| 2014/0235950 A1 | 8/2014 | Miles et al. |
| 2014/0236257 A1 | 8/2014 | Parker et al. |
| 2014/0237806 A1 | 8/2014 | Smith et al. |
| 2014/0243931 A1 | 8/2014 | Parker et al. |
| 2014/0249446 A1 | 9/2014 | Gharib et al. |
| 2014/0249599 A1 | 9/2014 | Kaula et al. |
| 2014/0277251 A1 | 9/2014 | Gerber et al. |
| 2014/0277270 A1 | 9/2014 | Parramon et al. |
| 2014/0288374 A1 | 9/2014 | Miles et al. |
| 2014/0288375 A1 | 9/2014 | Miles et al. |
| 2014/0288389 A1 | 9/2014 | Gharib et al. |
| 2014/0296737 A1 | 10/2014 | Parker et al. |
| 2014/0304773 A1 | 10/2014 | Woods et al. |
| 2014/0324144 A1 | 10/2014 | Ye et al. |
| 2014/0343628 A1 | 11/2014 | Kaula et al. |
| 2014/0343629 A1 | 11/2014 | Kaula et al. |
| 2014/0344733 A1 | 11/2014 | Kaula et al. |
| 2014/0344740 A1 | 11/2014 | Kaula et al. |
| 2014/0350636 A1 | 11/2014 | King et al. |
| 2015/0134027 A1 | 5/2015 | Kaula et al. |
| 2015/0214604 A1 | 7/2015 | Zhao et al. |
| 2016/0045747 A1 | 2/2016 | Jiang et al. |

FOREIGN PATENT DOCUMENTS

| | | |
|---|---|---|
| EP | 1904153 B1 | 4/2008 |
| EP | 2243509 A1 | 10/2010 |
| WO | WO 96/39932 A1 | 12/1996 |
| WO | WO 00/01320 A9 | 1/2000 |
| WO | WO 00/02623 A1 | 1/2000 |
| WO | WO 00/56677 A1 | 3/2000 |
| WO | WO 00/19939 A1 | 4/2000 |
| WO | WO 00/19940 A1 | 4/2000 |
| WO | WO 00/78389 A1 | 12/2000 |
| WO | WO 01/37728 A9 | 5/2001 |
| WO | WO 01/93759 A1 | 12/2001 |
| WO | WO 02/072194 A3 | 9/2002 |
| WO | WO 02/078592 A3 | 10/2002 |
| WO | WO 03/005887 A3 | 1/2003 |
| WO | WO 03/026482 A9 | 4/2003 |
| WO | WO 03/026739 A2 | 4/2003 |
| WO | WO 03/035163 A3 | 5/2003 |
| WO | WO 03/037170 A9 | 5/2003 |
| WO | WO 03/043690 A1 | 5/2003 |
| WO | WO 03/066162 A3 | 8/2003 |
| WO | WO 2004/036765 A2 | 4/2004 |
| WO | WO 2004/047914 A1 | 6/2004 |
| WO | WO 2004/052448 A1 | 6/2004 |
| WO | WO 2004/052449 A1 | 6/2004 |
| WO | WO 2004/058347 A1 | 7/2004 |
| WO | WO 2004/064634 A1 | 8/2004 |
| WO | WO 2004/066820 A2 | 8/2004 |
| WO | WO 2004/087256 A1 | 10/2004 |
| WO | WO 2005/000394 A1 | 1/2005 |
| WO | WO 2005/002664 A3 | 1/2005 |
| WO | WO 2005/002665 A3 | 1/2005 |
| WO | WO 2005/032332 A3 | 4/2005 |
| WO | WO 2005/081740 A3 | 9/2005 |
| WO | WO 2005/087307 A3 | 9/2005 |
| WO | WO 2005/105203 A1 | 11/2005 |
| WO | WO 2005/123185 A1 | 12/2005 |
| WO | WO 2006/012423 A1 | 2/2006 |
| WO | WO 2006/019764 A2 | 2/2006 |
| WO | WO 2006/029257 A2 | 3/2006 |
| WO | WO 2006/084194 A9 | 8/2006 |
| WO | WO 2006/091611 A1 | 8/2006 |
| WO | WO 2006/116256 A1 | 11/2006 |
| WO | WO 2006/119015 A1 | 11/2006 |
| WO | WO 2006/119046 A1 | 11/2006 |
| WO | WO 2006/127366 A1 | 11/2006 |
| WO | WO 2007/064924 A1 | 6/2007 |
| WO | WO 2007/064936 A1 | 6/2007 |
| WO | WO 2007/089394 A3 | 8/2007 |
| WO | WO 2007/108863 A1 | 9/2007 |
| WO | WO 2008/021524 A2 | 2/2008 |
| WO | WO 2008/039242 A1 | 4/2008 |
| WO | WO 2008/042902 A3 | 4/2008 |
| WO | WO 2009/021080 A2 | 2/2009 |
| WO | WO 2009/042172 A3 | 4/2009 |
| WO | WO 2009/042379 A1 | 4/2009 |
| WO | WO 2009/051965 A1 | 4/2009 |
| WO | WO 2009/137119 A1 | 11/2009 |
| WO | WO 2009/139907 A1 | 11/2009 |
| WO | WO 2009/139909 A1 | 11/2009 |
| WO | WO 2009/139910 A1 | 11/2009 |
| WO | WO 2009/139917 A3 | 11/2009 |
| WO | WO 2010/014055 A1 | 2/2010 |
| WO | WO 2010/014260 A1 | 2/2010 |
| WO | WO 2010/065143 A1 | 6/2010 |
| WO | WO 2011/011748 A1 | 1/2011 |
| WO | WO 2011/053607 A1 | 5/2011 |
| WO | WO 2011/053661 A1 | 5/2011 |
| WO | WO 2011/059565 A1 | 5/2011 |
| WO | WO 2011/100162 A1 | 8/2011 |
| WO | WO 2011/139779 A1 | 11/2011 |
| WO | WO 2011/153024 A1 | 12/2011 |
| WO | WO 2011/156286 A3 | 12/2011 |
| WO | WO 2011/156287 A3 | 12/2011 |
| WO | WO 2012/003451 A3 | 1/2012 |
| WO | WO 2012/054183 A1 | 4/2012 |
| WO | WO 2012/075265 A1 | 6/2012 |
| WO | WO 2012/075281 A1 | 6/2012 |
| WO | WO 2012/075299 A1 | 6/2012 |
| WO | WO 2012/075497 A1 | 6/2012 |
| WO | 2012/135733 A1 | 10/2012 |
| WO | WO 2012/135733 A1 | 10/2012 |
| WO | WO 2012/155183 A1 | 11/2012 |
| WO | WO 2012/155184 A1 | 11/2012 |
| WO | WO 2012/155185 A1 | 11/2012 |
| WO | WO 2012/155186 A1 | 11/2012 |
| WO | WO 2012/155187 A1 | 11/2012 |
| WO | WO 2012/155188 A1 | 11/2012 |
| WO | WO 2012/155189 A1 | 11/2012 |
| WO | WO 2012/155190 A1 | 11/2012 |
| WO | WO 2012/158766 A1 | 11/2012 |
| WO | WO 2013/028428 A1 | 2/2013 |
| WO | WO 2013/036630 A1 | 3/2013 |
| WO | WO 2013/141996 A1 | 9/2013 |
| WO | WO 2013/162708 A3 | 10/2013 |
| WO | WO 2013/155117 A1 | 11/2013 |
| WO | WO 2013/165395 A1 | 11/2013 |
| WO | WO 2014/089390 A1 | 6/2014 |
| WO | WO 2014/089392 A1 | 6/2014 |
| WO | WO 2014/089400 A1 | 6/2014 |
| WO | WO 2014/089405 A1 | 6/2014 |
| WO | WO 2014/089485 A1 | 6/2014 |
| WO | WO 2014/161000 A1 | 10/2014 |

(56) References Cited

FOREIGN PATENT DOCUMENTS

| WO | WO 2014/172381 A1 | 10/2014 |
|----|-------------------|---------|
| WO | 2016/025913 A1    | 2/2016  |

OTHER PUBLICATIONS

Buhlmann, J., et al., Modeling of a segmented electrode for desynchronizing deep brain stimulation, Frontiers in Neuroengineering, Dec. 8, 2011, vol. 4, 15, pp. 1-8.

Ghovanloo, M., et al., A Small Size Large Voltage Compliance Programmable Current Source for Biomedical Implantable Microstimulators, Proceedings of the 25th Annual International Conference of the IEEE EMBS, Sep. 17-21, 2003, pp. 1979-1982.

Noblett, K. L., Neuromodulation and the role of electrodiagnostic techniques, International Urogynecology Journal, Dec. 2010, vol. 21, 2, pp. 461-466.

Tanagho, E., et al., Bladder Pacemaker: Scientific Basis and Clinical Future, Urology, Dec. 1982, vol. 20, No. 6, pp. 614-619.

U.S. Appl. No. 14/827,074, filed Aug. 14, 2015.
U.S. Appl. No. 14/991,649, filed Jan. 8, 2016.
U.S. Appl. No. 14/827,081, filed Aug. 14, 2015.
U.S. Appl. No. 14/827,095, filed Aug. 14, 2015.
U.S. Appl. No. 14/827,067, filed Aug. 14, 2015.
U.S. Appl. No. 14/991,784, filed Jan. 8, 2016.
U.S. Appl. No. 62/101,899, filed Jan. 9, 2015.
U.S. Appl. No. 62/101,897, filed Jan. 9, 2015.
U.S. Appl. No. 62/110,274, filed Jan. 30, 2015.
U.S. Appl. No. 62/038,122, filed Aug. 15, 2014.
U.S. Appl. No. 62/101,666, filed Jan. 9, 2015.
U.S. Appl. No. 62/101,884, filed Jan. 9, 2015.
U.S. Appl. No. 62/101,782, filed Jan. 9, 2015.
U.S. Appl. No. 62/191,134, filed Jul. 10, 2015.
International Search Report and Written Opinion, dated Nov. 15, 2015 for PCT/US2015/045408, 22 pages.
Noblett et al, "Neuromodulation and the role of electrodiagnostic techniques," International Urogynecology Journal, vol. 21, No. 2, (2010) pp. 461-466.

\* cited by examiner

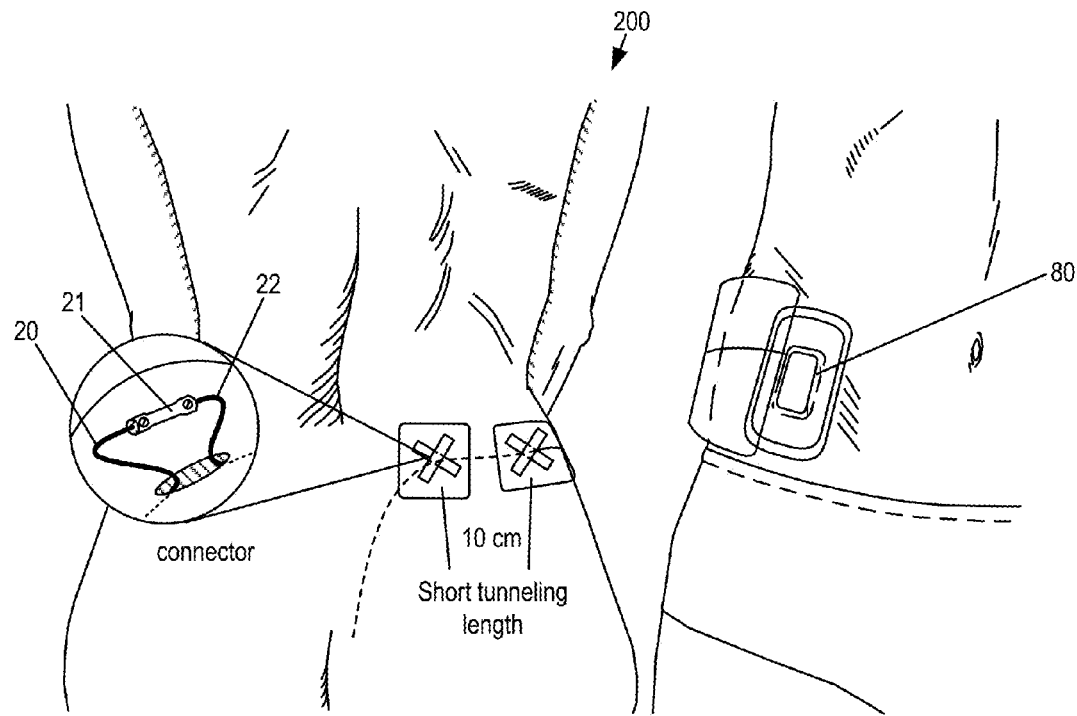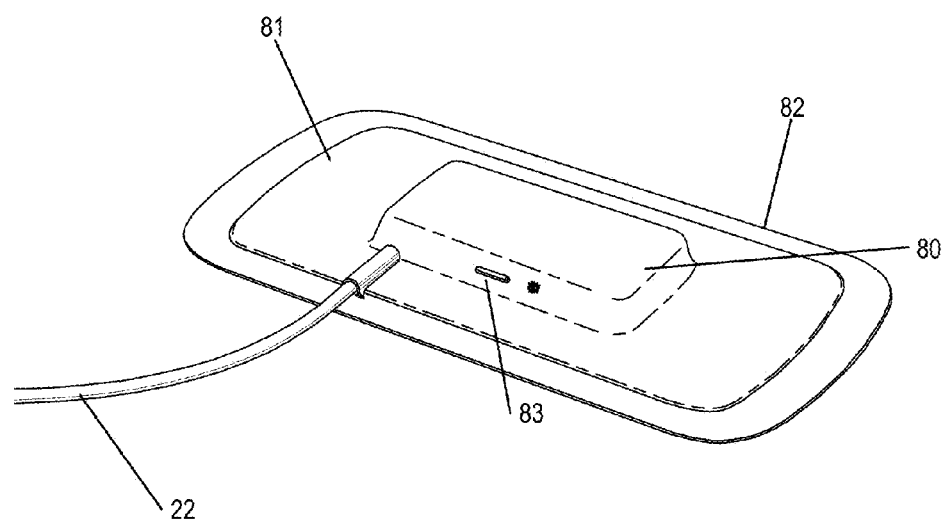
FIG. 3B

CMAP Response

Raw EMG trace + Processed using RMS

Too Shallow

Suggestion: Insert Deeper

Too Deep

Suggestion: pull back

*FIG. 12A*

Lead

20

"tilted" in an angle 3
2
1
0

Sciatic Nerve

*FIG. 12B*

Lead

20

S1
S2
S3

3
2
1
0

Sciatic Nerve

Suggestion:

Dashboard – IPG Data Display – threshold summary and contact status

CASE STUDY 1

Bipolar, Cathode = "-"; Anode= "+"

| Threshold (mA) | Recommendation A | Recommendation B | Recommendation C | Recommendation D |
|---|---|---|---|---|
| 1.7 | - | + |   | + |
| 0.9 |   |   | - |   |
| 1.2 |   |   |   | - |
| 1.9 | + | - | + |   |

Monopolar, IPG Can as anode

| Threshold (mA) | Recommendation A | Recommendation B | Recommendation C | Recommendation D |
|---|---|---|---|---|
| 1.7 | - |   |   |   |
| 0.9 |   |   | - |   |
| 1.2 |   |   |   | - |
| 1.9 |   | - |   |   |

*FIG. 19A*

CASE STUDY 2

Bipolar, Cathode = "-"; Anode= "+"

| Threshold (mA) | Recommendation A | Recommendation B | Recommendation C | Recommendation D |
|---|---|---|---|---|
| 1.3 | - |   | - | + |
| 1.6 |   | - | - |   |
| 2.7 |   |   |   | - |
| 4.1 | + | + | + |   |

Monopolar, IPG Can as anode

| Threshold (mA) | Recommendation A | Recommendation B | Recommendation C | Recommendation D |
|---|---|---|---|---|
| 1.3 | - |   | - |   |
| 1.6 |   | - | - |   |
| 2.7 |   |   |   | - |
| 4.1 |   |   |   |   |

*FIG. 19B*

ELECTROMYOGRAPHIC LEAD POSITIONING AND STIMULATION TITRATION IN A NERVE STIMULATION SYSTEM FOR TREATMENT OF OVERACTIVE BLADDER

CROSS-REFERENCES TO RELATED APPLICATIONS

The present application is a continuation of U.S. application Ser. No. 14/827,108 entitled "ELECTROMYOGRAPHIC LEAD POSITIONING AND STIMULATION TITRATION IN A NERVE STIMULATION SYSTEM FOR TREATMENT OF OVERACTIVE BLADDER," filed on Aug. 14, 2015, which claims the benefit of priority of U.S. Provisional Application Nos. 62/038,131 filed on Aug. 15, 2014; 62/041,611 filed on Aug. 25, 2014; and 62/101,888 filed on Jan. 9, 2015; the entire contents of which are incorporated herein by reference in their entireties for all purposes.

The present application is related to pending U.S. Non-Provisional patent application Ser. No. 14/827,074, U.S. Application Publication 2016/0045724, entitled "Devices and Methods for Anchoring of Neurostimulation Leads"; pending U.S. Non-Provisional patent application Ser. No. 14/827,081, U.S. Application Publication 2016/0045745, entitled "External Pulse Generator Device and Associated Methods for Trial Nerve Stimulation"; pending U.S. Non-Provisional patent application Ser. Nos. 14/827,095, U.S. Application Publication 2016/0045746, entitled "Integrated Electromyographic Clinician Programmer For Use With an Implantable Neurostimulator" and pending U.S. Non-Provisional patent application Ser. Nos. 14/827,067, U.S. Application Publication 2016/0045751, entitled "Systems and Methods for Neurostimulation Electrode Configurations Based on Neural Localization"; and U.S. Provisional Application Nos. 62/101,666, entitled "Patient Remote and Associated Methods of Use With a Nerve Stimulation System" filed on Jan. 9, 2015; 62/101,884, entitled "Attachment Devices and Associated Methods of Use With a Nerve Stimulation Charging Device" filed on Jan. 9, 2015; 62/101,782, entitled "Improved Antenna and Methods of Use For an Implantable Nerve Stimulator" filed on Jan. 9, 2015; and 62/191,134, entitled "Implantable Nerve Stimulator Having Internal Electronics Without ASIC and Methods of Use" filed on Jul. 10, 2015; each of which is assigned to the same assignee and incorporated herein by reference in its entirety for all purposes.

FIELD OF THE INVENTION

The present invention relates to neurostimulation treatment systems and associated devices, as well as methods of treatment, implantation and configuration of such treatment systems.

BACKGROUND OF THE INVENTION

Treatments with implantable neurostimulation systems have become increasingly common in recent years. While such systems have shown promise in treating a number of conditions, effectiveness of treatment may vary considerably between patients. A number of factors may lead to the very different outcomes that patients experience, and viability of treatment can be difficult to determine before implantation. For example, stimulation systems often make use of an array of electrodes to treat one or more target nerve structures. The electrodes are often mounted together on a multi-electrode lead, and the lead implanted in tissue of the patient at a position that is intended to result in electrical coupling of the electrode to the target nerve structure, typically with at least a portion of the coupling being provided via intermediate tissues. Other approaches may also be employed, for example, with one or more electrodes attached to the skin overlying the target nerve structures, implanted in cuffs around a target nerve, or the like. Regardless, the physician will typically seek to establish an appropriate treatment protocol by varying the electrical stimulation that is applied to the electrodes.

Current stimulation electrode placement/implantation techniques and known treatment setting techniques suffer from significant disadvantages. The nerve tissue structures of different patients can be quite different, with the locations and branching of nerves that perform specific functions and/or enervate specific organs being challenging to accurately predict or identify. The electrical properties of the tissue structures surrounding a target nerve structure may also be quite different among different patients, and the neural response to stimulation may be markedly dissimilar, with an electrical stimulation pulse pattern, pulse width, frequency, and/or amplitude that is effective to affect a body function of one patient and potentially imposing significant discomfort or pain, or having limited effect, on another patient. Even in patients where implantation of a neurostimulation system provides effective treatment, frequent adjustments and changes to the stimulation protocol are often required before a suitable treatment program can be determined, often involving repeated office visits and significant discomfort for the patient before efficacy is achieved. While a number of complex and sophisticated lead structures and stimulation setting protocols have been implemented to seek to overcome these challenges, the variability in lead placement results, the clinician time to establish suitable stimulation signals, and the discomfort (and in cases the significant pain) that is imposed on the patient remain less than ideal. In addition, the lifetime and battery life of such devices is relatively short, such that implanted systems are routinely replaced every few years, which requires additional surgeries, patient discomfort, and significant costs to healthcare systems.

Furthermore, since the morphology of the nerve structures vary considerably between patients, placement and alignment of neurostimulation leads relative the targeted nerve structures can be difficult to control, which can lead to inconsistent placement, unpredictable results and widely varying patient outcomes. For these reasons, neurostimulation leads typically include multiple electrodes with the hope that at least one electrode or a pair of electrodes will be disposed in a location suitable for delivering neurostimulation. One drawback with this approach is that repeated office visits may be required to determine the appropriate electrodes to use and/or to arrive at a neurostimulation program that delivers effective treatment. Often, the number of usable neurostimulation programs may be limited by imprecise lead placement.

The tremendous benefits of these neural stimulation therapies have not yet been fully realized. Therefore, it is desirable to provide improved neurostimulation methods, systems and devices, as well as methods for implanting and configuring such neurostimulation systems for a particular patient or condition being treated. It would be particularly helpful to provide such systems and methods so as to improve ease of use by the physician in positioning and configuring the system, as well as improve patient comfort and alleviation of symptoms for the patient. It would further be desirable to improve ease and accuracy of lead placement as well as improve determination and availability of effective neurostimulation treatment programs.

BRIEF SUMMARY OF THE INVENTION

The present invention generally relates to neurostimulation treatment systems and associated devices and methods, and in particular to improved integrated electromyography (EMG) clinician programmers which allow for more accurate and objective positioning, programming, and configuration of implantable electrode leads. The present invention has particular application to sacral nerve stimulation treatment systems configured to treat bladder and bowel dysfunctions. It will be appreciated however that the present invention may also be utilized for the treatment of pain or other indications, such as movement or affective disorders, as will be appreciated by one of skill in the art.

The integrated EMG clinician programmer of the present invention provides an objective and quantitative means by which to standardize placement and programming of implantable leads and neurostimulation electrodes, reducing the subjective assessment of patient sensory responses as well as surgical, programming, and re-programming time. Further, as the efficacy of treatment often relies on precise placement of the neurostimulation electrodes at target tissue locations and the consistent, repeatable delivery of neurostimulation therapy, using an objective EMG measurement can substantially improve the utility and success of treatment. Use of the integrated EMG clinician programmer to verify activation of motor responses can further improve the lead placement performance of less experienced operators and allow such physicians to perform lead placement with confidence and greater accuracy. Still further, automation of several steps or procedures associated with lead placement and programming with the integrated clinician programmer can further reduce the duration and complexity of the procedure and improve consistency of patient outcomes. For example, automation of electrode threshold determinations based on EMG responses can provide rapid feedback during lead placement and to identify optimal programming parameters.

An integrated electromyography (EMG) and signal generation clinician programmer may be coupled with an implantable temporary or permanent lead in a patient and at least one EMG sensing electrode minimally invasively positioned on a skin surface or within the patient. Generally, the integrated clinician programmer may comprise a portable housing, a signal/stimulation generator, an EMG signal processor/recorder, and a graphical user interface. The housing has an external surface and encloses circuitry at least partially disposed within the housing. The signal/stimulation generator may be disposed within the housing and configured to deliver test stimulation to a nerve tissue of the patient via a percutaneous needle or the implantable lead. The EMG signal processor may be disposed within the housing and configured to record a stimulation-induced EMG motor response for each test stimulation via the at least one pair of EMG sensing electrodes and a ground electrode. The graphical user interface at least partially comprises the external surface of the housing and has a touch screen display for direct user interaction or for use with a keyboard, mouse, or the like. As described in greater detail below, the integrated clinician programmer allows for controlled positioning or programming of the implantable lead based at least on the EMG record and provides the clinician with a convenient all-in-one setup via the EMG integrated clinician programmer.

The present invention provides improved methods for positioning of an implantable lead in a patient with an integrated EMG and stimulation clinician programmer. The integrated clinician programmer is coupled to the implantable lead, wherein the implantable lead comprises at least four electrodes, and to at least one pair of EMG sensing electrodes minimally invasively positioned on a skin surface or within the patient. The method comprises first delivering test stimulation at a stimulation amplitude level from the integrated clinician programmer to a nerve tissue of the patient with a principal or reference electrode of the implantable lead. Test stimulations are selected or adjusted in proportional increments to achieve a desired stimulation-induced EMG motor response. The method further includes test stimulations delivered at a same stimulation amplitude level for a same period of time sequentially to each of the four electrodes of the implantable lead. A stimulation-induced EMG motor response is recorded with the integrated clinician programmer for each test stimulation on each electrode of the implantable lead via the at least one EMG sensing electrode so as to facilitate initial positioning of the implantable lead at a target stimulation region.

The principal electrode is selected from the at least four electrodes of the implantable lead. For example, user input may be received related to selection of the principal electrode via a graphical user interface of the integrated clinician programmer. Additionally, user input related to adjustment of the stimulation amplitude level of the test stimulation for the principal electrode to achieve a desired stimulation-induced EMG motor response may be received via the graphical user interface of the integrated clinician programmer. For example, the user may adjust the stimulation amplitude of the test stimulation in increments in a range from about 0.05 mA to about 0.25 mA, wherein the test stimulation amplitude is generally less than 10 mA. The use of proportional increases in stimulation amplitude during test stimulation and/or programming effectively reduces the time required for such activities. The period of time for stimulation of each individual electrode comprises about 1 second and a sweeping cycle of the implantable lead is completed in less than or equal to about 5 seconds.

As discussed above, automation of certain aspects within the clinician programmer can further reduce the duration and complexity of the procedure and improve consistency of outcomes. For example, the principal electrode may be automatically selected based on a default condition by the integrated clinician programmer. Still further, the clinician programmer may be configured to automatically adjust the stimulation amplitude level of the test stimulation for the principal electrode until a desired stimulation-induced EMG motor response is detected to provide rapid feedback during initial lead placement. The desired EMG motor response may comprises a value associated with a minimum or maximum compound muscle action potential (CMAP). Automatically adjusting may comprise increasing the stimulation amplitude in increments of 0.05 mA for a test stimulation less than or equal to 1 mA, 0.1 mA for a test stimulation more than or equal to 1 mA and less than or equal to 2 mA, 0.2 mA for a test stimulation more than or equal to 2 mA and less than or equal to 3 mA, or 0.25 mA for a test stimulation more than or equal to 3 mA. The use of proportional increases in combination with the automated feature in stimulation amplitude adjusting during initial lead placement effectively reduces the time required for such activities. It will be appreciated that this automated feature may be easily terminated at any time and for any reason, patient safety or otherwise, by the user.

An EMG response value may be calculated by the integrated clinician programmer for each test stimulation delivered at a given stimulation amplitude level to each electrode based on a maximum EMG response amplitude (e.g., maximum CMAP peak, peak to peak, root mean square; up to 500 µVolts) associated with each electrode. Alternatively, the EMG response value may be calculated based on a maximum EMG response amplitude associated with each electrode which is normalized relative to an EMG response amplitude associated with the principal electrode (e.g., unitless R-value indicative of good (e.g., R≥0.5), not ideal (e.g., 0.25≤R≤0.5), or not acceptable positioning (e.g., R≤0.25)). Importantly, the EMG response value associated with each electrode may provide visual feedback to a user on how to laterally or axially position the implantable lead at the target stimulation region via the graphical user interface of the integrated clinician programmer. For example, the graphical user interface may include an implantable lead graphical element and the visual feedback comprises a color coding from at least three contrasting colors on a side of each associated electrode of the implantable lead graphical element. This visual feedback, in combination with fluoroscopy images, provides directional indication to the user on how to re-position the implantable lead with reference to the target nerve tissue. For example, whether the operator should advance the implantable lead distally along an insertion axis, retract the implantable lead proximally along the insertion axis, or steer the implantable lead along a lateral direction from the insertion axis so that a middle of the implantable lead is positioned at the target stimulation region. Alternatively or additionally, a relative distance or position of each electrode to the target stimulation region may be calculated based on the EMG response value associated with each electrode. The delivering test stimulations to each of the four electrodes of the implantable lead and recording steps after lead re-positioning may be repeated to confirm the calculated EMG response value for each electrode are within a desired similar value range (e.g., R-values=1), and/or the maximum EMG response amplitude for each electrode are within a desired robust response range (e.g., large CMAP) and the associated simulation amplitude for each electrode is within a desired reasonable stimulation range (e.g., lower stimulation amplitudes).

For sacral nerve stimulation treatment systems configured to treat bladder and bowel dysfunctions, the lead is configured to be inserted through a foramen of a sacrum and positioned in proximity of a sacral nerve root. For example, the target stimulation region may comprise an area the emergence of a sacral nerve from the sacral canal and it's convergence with other spinal nerves to form the sciatic nerve. A visual image of the recorded stimulation-induced EMG motor response during each test stimulation may be displayed on the graphical user interface of the integrated clinician programmer, wherein the visual image includes a waveform comprising a CMAP.

Methods further include validating and fine tuning lead placement by testing for a stimulation amplitude threshold for each electrode. For example, user input may be received related to an adjustment of the stimulation amplitude threshold of the test stimulation for each electrode in proportional increments to achieve a desired stimulation-induced EMG motor response at a minimum stimulation amplitude threshold via a graphical user interface of the integrated clinician programmer. The graphical user interface may further receive user input related to the recorded stimulation-induced EMG motor response (e.g., yes or no) or a sensory response from the patient (e.g., none, good, or bad) associated with the stimulation amplitude threshold for each electrode. For example, a negative sensory response from the patient associated with the stimulation amplitude threshold for a particular electrode may automatically override any positive or neutral feedback to the user on the stimulation amplitude threshold for that particular electrode. As discussed in greater detail below, user characterization of the presence or absence of motor and/or sensor responses may be of additional benefit in fine tuning lead placement.

Visual feedback may be displayed to the user on the stimulation amplitude threshold for each electrode, wherein the visual feedback comprises color coding from at least three contrasting colors on the graphical user interface. The graphical user interface may also include a visual indicator (e.g., color coding, symbols, shapes, empirical values) associated with each stimulation electrode and configured to indicate a status of the stimulation electrode (e.g., good if between 1-3 mA, bad if less than 0.5 mA or greater than 4 mA, ok if between 0.5-1 mA or 3-4 mA), an amplitude threshold value (e.g., up to 10 mA) of the stimulation electrode based on EMG record, an EMG value or status associated with the stimulation amplitude threshold value (e.g., up to 500 µVolts or unitless R-value indicative of good, not ideal, or not acceptable positioning), a sensory response status associated with the stimulation amplitude threshold value (e.g., none, good, bad), or an impedance status of the stimulation electrode (e.g., good if less than 3000 Ohms and greater than 50 Ohms and bad if greater than 3000 Ohms or less than 50 Ohms).

Optionally, as discussed above, the integrated clinician programmer may automatically adjust the stimulation amplitude threshold (e.g., slow proportional increases) of the test stimulation for each electrode to achieve a desired stimulation-induced EMG motor response at a minimum stimulation amplitude threshold. Of particular benefit, the integrated clinician programmer automatically stores, displays, and easily makes this characterization data available during the procedure, and is a far advancement over current clinical practices which employ paper notes and/or calculations in a clinician's head. Data for each test stimulation includes the incremental or proportional stimulation amplitude levels for each individual electrode of the at least four electrodes of the implantable lead, an associated EMG recording associated with the stimulation amplitude threshold, or user input related to the recorded stimulation-induced EMG motor response or a sensory response from the patient associated with the stimulation amplitude threshold.

The present invention provides further methods for improved positioning of an implantable lead in a patient in proximity of a sacral nerve root so as to treat bladder or bowel dysfunction. The implantable lead may comprise at least four stimulation electrodes arranged in a linear array along a length of the lead and be coupled to an integrated EMG and stimulation clinician programmer. The integrated clinician programmer may include connectors on the housing for coupling the EMG signal processor to first and second EMG sensing electrodes. EMG sensing electrodes are positionable on the medial border or sole of the foot to record EMG signals associated with plantar flexion of the big toe. The EMG sensing electrodes are positioned over and may record activity from the flexor hallucis brevis muscle and/or abductor hallucis muscle. The integrated clinician programmer may include connectors on the housing for coupling the EMG signal processor to a second pair of EMG sensing electrodes. The second pair of EMG sensing electrodes are positionable within the inner area of the patient buttocks near the anal sphincter, with positioning targeted over the levator ani muscles. These EMG sensing electrodes are positioned to record the anal bellows response of the patient, which represents activation of the levator ani muscles of the perineal musculature.

It will be appreciated that the EMG signal processor can also record a stimulation-induced EMG motor response associated with the big toe only or a stimulation-induced EMG motor response associated with the anal bellows only for each test stimulation. The test stimulation delivered by the signal generator comprises at least one electrical pulse below a muscle activation threshold and the EMG sensing electrodes detects stimulation of the nerve tissue. The integrated clinician programmer may further include an additional connector on the housing for coupling the signal generator to a foramen needle configured to identify or locate a target nerve prior to initial lead placement, as discussed in greater detail below.

The method comprises first delivering test stimulation at a plurality of stimulation amplitude levels from the integrated clinician programmer to the sacral nerve tissue of the patient with a principal electrode of the implantable lead, wherein the principal electrode is selected from the at least four electrodes of the implantable lead. Test stimulations are selected or adjusted in proportional increments to achieve a desired stimulation-induced EMG motor response. The method further includes test stimulations delivered at a same stimulation amplitude level for a same period of time sequentially to each of the four electrodes of the implantable lead. The integrated clinician programmer simultaneously records a first stimulation-induced EMG motor response associated with the big toe of the patient and a second stimulation-induced EMG motor response associated with the anal bellows of the patient for the test stimulations on each electrode of the implantable lead so as to provide for controlled positioning of the implantable lead at a target stimulation region.

As discussed above, user input may be received related to adjustment of the stimulation amplitude level of the test stimulation for the principal electrode in proportional increments to achieve a desired stimulation-induced EMG motor response via a graphical user interface of the integrated clinician programmer. Alternatively, the integrated clinician programmer may automatically adjust the stimulation amplitude level of the test stimulation for the principal electrode in proportional increments until a desired stimulation-induced EMG motor response is detected (e.g., increases rapidly until initial response is observed).

An EMG response value for each test stimulation delivered at a given stimulation amplitude level to each electrode may be calculated as discussed above. For example, it may be based on a maximum EMG response amplitude associated with each electrode which is normalized relative to an EMG response amplitude associated with the principal electrode. The EMG response value associated with each electrode provides visual feedback to a user on how to position the implantable lead at the target stimulation region within the patient.

Once the implantable lead is initially positioned, further input related to an adjustment of a stimulation amplitude threshold of the test stimulation for each electrode to achieve a desired stimulation-induced EMG motor response at a minimum stimulation amplitude threshold may be received via the graphical user interface. Additional user input related to the first or second recorded stimulation-induced EMG motor response or a sensory response from the patient associated with the stimulation amplitude threshold for each electrode may also be received. Again, the integrated clinician programmer may automatically adjust a stimulation amplitude threshold of the test stimulation for each electrode in proportional increments to achieve the desired stimulation-induced EMG motor response at a minimum stimulation amplitude threshold (e.g., increase slowly until the maximum magnitude EMG response is observed).

The integrated clinician programmer automatically stores or displays data for each test stimulation delivered at incremental or proportional stimulation amplitude levels for each individual electrode of at least four electrodes of the implantable lead and the associated EMG recording of the big toe and the anal bellows of the patient for each test stimulation. Method further include delivering the test stimulation to the sacral nerve tissue via a foramen needle and recording the stimulation-induced EMG motor response for each test stimulation delivered to the foramen needle so as to provide for initial positioning of the implantable lead at the target stimulation region. Similarly, user input may be received related to an adjustment of a stimulation amplitude level of the test stimulation for the foramen needle in proportional increments to achieve a desired stimulation-induced EMG motor response via the graphical user interface of the integrated clinician programmer. Optionally, automatic adjustments to the stimulation amplitude level of the test stimulation for the foramen needle may be made by the integrated clinician programmer until a desired stimulation-induced EMG motor response is detected.

The present invention provides methods for positioning an implantable lead in a patient with an integrated EMG and stimulation clinician programmer. The method comprises implanting a temporary or permanent lead having at least four electrodes in proximity of nerve tissue of a patient. At least one EMG sensing electrode is positioned on a skin surface or within the patient. The implantable lead is coupled to the integrated clinician programmer via a stimulation cable and the at least one EMG sensing electrode is also coupled to the integrated clinician programmer. A principal electrode is selected from the at least four electrodes of the implantable lead via a graphical user interface of the integrated clinician programmer and stimulated with a test stimulation via the integrated clinician programmer. A record of a stimulation-induced EMG motor response, as sensed by the at least one pair of EMG sensing electrodes, is displayed on the graphical user interface.

A stimulation amplitude of the test stimulation for the principal electrode is selected or adjusted in proportional increments to achieve a desired stimulation-induced EMG motor response via the graphical user interface. The method further includes sequentially stimulating the at least four electrodes of the implantable lead with the test stimulation at a same selected or adjusted stimulation amplitude level for a same period of time sequentially. Based at least on the EMG records, the implantable lead is re-positioned (e.g., advancing the implantable lead distally along an insertion axis, retracting the implantable lead proximally along the insertion axis, or steering the implantable lead along a lateral direction from the insertion axis). Re-positioning may be further supplemented by fluoroscopy or anatomical landmarks/markers. Methods may also include sequentially stimulating and re-positioning the lead until an optimal lead positioning near the nerve tissue is achieved. After initial lead placement is completed, the user may further adjust a stimulation amplitude threshold of the test stimulation for each electrode in proportional increments to achieve a desired stimulation-induced EMG motor response at a minimum stimulation amplitude threshold and/or provide input related to the EMG record associated with each test stimulation or a sensory response from the patient associated with the stimulation amplitude threshold for each electrode.

Systems for improved positioning of an implantable lead in a patient are also provided by the present invention. The system may comprise an integrated EMG and stimulation clinician programmer, an implantable lead coupleable to the clinician programmer, wherein the implantable lead comprises at least four electrodes, and at least one EMG sensing electrode minimally invasively positionable on a skin surface or within the patient, the EMG sensing electrode coupleable to the integrated clinician programmer. The clinician programmer is configured for (1) delivering a test stimulation at a stimulation amplitude level to a nerve tissue of the patient with a principal electrode of the implantable lead, wherein the principal electrode is selected from the at least four electrodes of the implantable lead, (2) delivering test stimulations at a same stimulation amplitude level for a same period of time sequentially to each of the four electrodes of the implantable lead, (3) and recording a stimulation-induced EMG motor response with the integrated clinician programmer for the test stimulations as sensed via the at least one EMG sensing electrode so as to facilitate positioning of the implantable lead at a target stimulation region.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

BRIEF DESCRIPTION OF THE DRAWINGS

FIG. 3B shows an example of a neurostimulation system having a partly implanted stimulation lead and an external pulse generator adhered to the skin of the patient for use in a trial stimulation, in accordance with aspects of the invention.

FIGS. 8A-1 thru 8A-3 and 8B schematically illustrate workflows for using a clinician programmer in placing the neurostimulation leads and programming the implanted neurostimulation lead, in accordance with aspects of the invention FIG. 9A schematically illustrates a nerve stimulation system setup for neural localization and lead implantation that utilizes a control unit with a stimulation clip, ground patches, two electromyography sensor patch sets, and ground patch sets connected during the operation of placing a trial or permanent neurostimulation system, in accordance with aspects of the invention.

FIGS. 12A-12B illustrate differing positions of the neurostimulation lead relative the targeted nerve during placement of the lead and FIGS. 13A-13F illustrate curves of R-values of the electrodes used to determine distance of the electrodes from the target nerve to facilitate placement of the lead, in accordance with aspects of the invention.

FIGS. 19A-19B illustrate electrode configuration recommendations based on example case studies of electrode thresholds, in accordance with aspects of the invention.

DETAILED DESCRIPTION OF THE INVENTION

Figure 1:
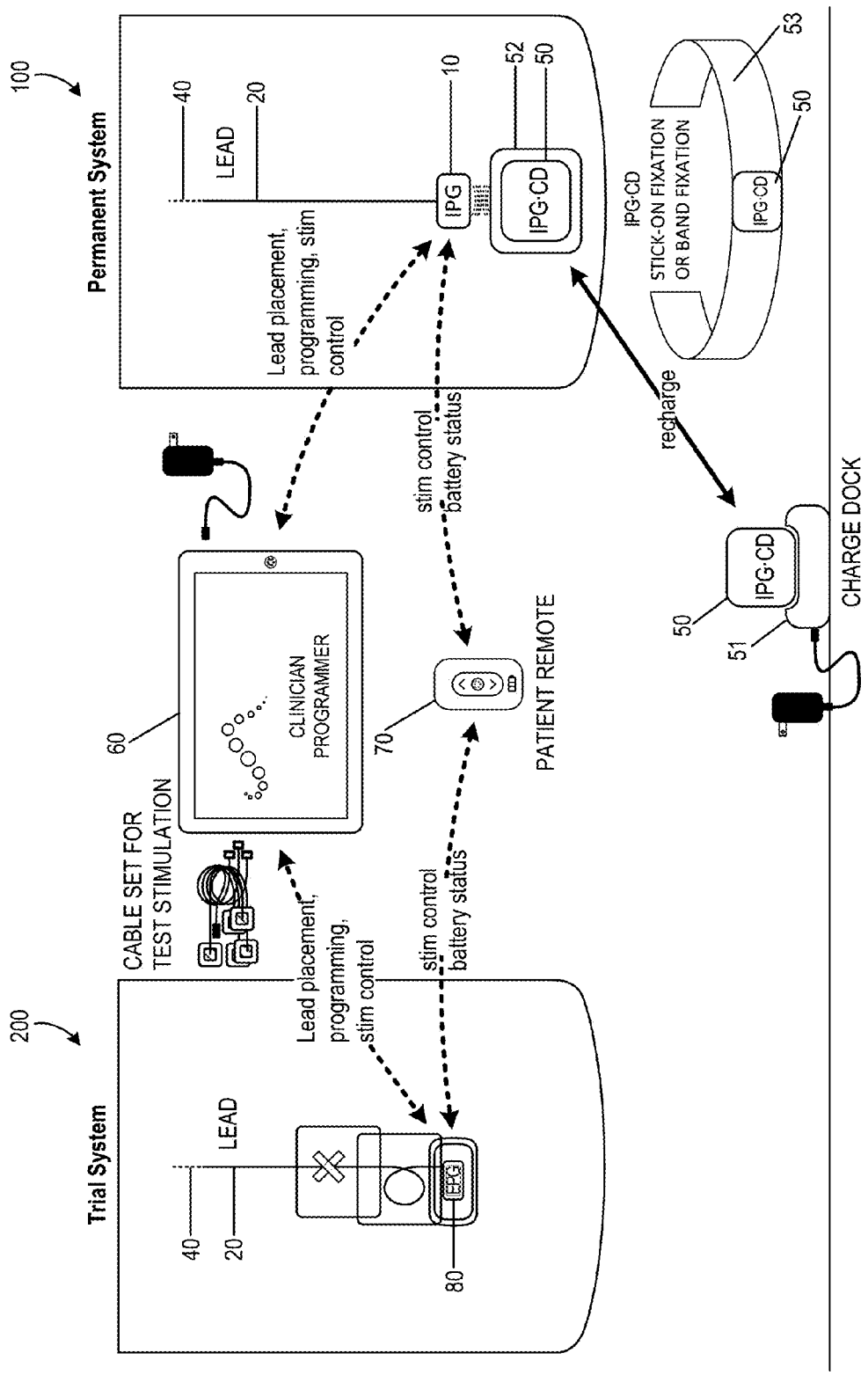
FIG. 1 schematically illustrates a nerve stimulation system, which includes a clinician programmer and a patient remote used in positioning and/or programming of both a trial neurostimulation system and a permanently implanted neurostimulation system, in accordance with aspects of the invention.

The present invention relates to neurostimulation treatment systems and associated devices, as well as methods of treatment, implantation/placement and configuration of such treatment systems. In particular embodiments, the invention relates to sacral nerve stimulation treatment systems configured to treat bladder dysfunctions, including overactive bladder ("OAB"), as well as fecal dysfunctions and relieve symptoms associated therewith. For ease of description, the present invention may be described in its use for OAB, it will be appreciated however that the present invention may also be utilized for any variety of neuromodulation uses, such as bowel disorders (e.g., fecal incontinence, fecal frequency, fecal urgency, and/or fecal retention), the treatment of pain or other indications, such as movement or affective disorders, as will be appreciated by one of skill in the art.

I. Neurostimulation Indications

Neurostimulation (or neuromodulation as may be used interchangeably hereunder) treatment systems, such as any of those described herein, can be used to treat a variety of ailments and associated symptoms, such as acute pain disorders, movement disorders, affective disorders, as well as bladder related dysfunction and bowel disorders. Examples of pain disorders that may be treated by neurostimulation include failed back surgery syndrome, reflex sympathetic dystrophy or complex regional pain syndrome, causalgia, arachnoiditis, and peripheral neuropathy. Movement orders include muscle paralysis, tremor, dystonia and Parkinson's disease. Affective disorders include depressions, obsessive-compulsive disorder, cluster headache, Tourette syndrome and certain types of chronic pain. Bladder related dysfunctions include but are not limited to OAB, urge incontinence, urgency-frequency, and urinary retention. OAB can include urge incontinence and urgency-frequency alone or in combination. Urge incontinence is the involuntary loss or urine associated with a sudden, strong desire to void (urgency). Urgency-frequency is the frequent, often uncontrollable urges to urinate (urgency) that often result in voiding in very small amounts (frequency). Urinary retention is the inability to empty the bladder. Neurostimulation treatments can be configured to address a particular condition by effecting neurostimulation of targeted nerve tissues relating to the sensory and/or motor control associated with that condition or associated symptom. Bowel disorders may include any of the variety of inflammatory, motility, and incontinence conditions.

In one aspect, the methods and systems described herein are particularly suited for treatment of urinary and fecal dysfunctions. These conditions have been historically under-recognized and significantly underserved by the medical community. OAB is one of the most common urinary dysfunctions. It is a complex condition characterized by the presence of bothersome urinary symptoms, including urgency, frequency, nocturia and urge incontinence. It is estimated that about 40 million Americans suffer from OAB. Of the adult population, about 16% of all men and women live with OAB symptoms.

OAB symptoms can have a significant negative impact on the psychosocial functioning and the quality of life of patients. People with OAB often restrict activities and/or develop coping strategies. Furthermore, OAB imposes a significant financial burden on individuals, their families, and healthcare organizations. The prevalence of co-morbid conditions is also significantly higher for patients with OAB than in the general population. Co-morbidities may include falls and fractures, urinary tract infections, skin infections, vulvovaginitis, cardiovascular, and central nervous system pathologies. Chronic constipation, fecal incontinence, and overlapping chronic constipation occur more frequently in patients with OAB.

Conventional treatments of OAB generally include lifestyle modifications as a first course of action. Lifestyle modifications include eliminating bladder irritants (such as caffeine) from the diet, managing fluid intake, reducing weight, stopping smoking, and managing bowel regularity. Behavioral modifications include changing voiding habits (such as bladder training and delayed voiding), training pelvic floor muscles to improve strength and control of urethral sphincter, biofeedback and techniques for urge suppression. Medications are considered a second-line treatment for OAB. These include anti-cholinergic medications (oral, transdermal patch, and gel) and oral beta-3 adrenergic agonists. However, anti-cholinergics are frequently associated with bothersome, systemic side effects including dry mouth, constipation, urinary retention, blurred vision, somnolence, and confusion. Studies have found that more than 50% of patients stop using anti-cholinergic medications within 90 days due to a lack of benefit, adverse events, or cost.

When these approaches are unsuccessful, third-line treatment options suggested by the American Urological Association include intradetrusor (bladder smooth muscle) injections of botulinum toxin (BTX), Percutaneous Tibial Nerve Stimulation (PTNS) and Sacral Nerve Stimulation (SNM). BTX is administered via a series of intradetrusor injections under cystoscopic guidance, but repeat injections of BTX are generally required every 4 to 12 months to maintain effect and BTX may undesirably result in urinary retention. A number or randomized controlled studies have shown some efficacy of BTX injections in OAB patients, but long-term safety and effectiveness of BTX for OAB is largely unknown.

PTNS therapy consists of weekly, 30-minute sessions over a period of 12 weeks, each session using electrical stimulation that is delivered from a hand-held stimulator to the sacral plexus via the tibial nerve. For patients who respond well and continue treatment, ongoing sessions, typically every 3-4 weeks, are needed to maintain symptom reduction. There is potential for declining efficacy if patients fail to adhere to the treatment schedule. Efficacy of PTNS has been demonstrated in a few randomized-controlled studies, however, there is limited data on PTNS effectiveness beyond 3-years and PTNS is not recommended for patients seeking a cure for urge urinary incontinence (UUI) (e.g., 100% reduction in incontinence episodes) (EAU Guidelines).

II. Sacral Neuromodulation

SNM is an established therapy that provides a safe, effective, reversible, and long-lasting treatment option for the management of urge incontinence, urgency-frequency, and non-obstructive urinary retention. SNM therapy involves the use of mild electrical pulses to stimulate the sacral nerves located in the lower back. Electrodes are placed next to a sacral nerve, usually at the S3 level, by inserting the electrode leads into the corresponding foramen of the sacrum. The electrodes are inserted subcutaneously and are subsequently attached to an implantable pulse generator (IPG). The safety and effectiveness of SNM for the treatment of OAB, including durability at five years for both urge incontinence and urgency-frequency patients, is supported by multiple studies and is well-documented. SNM has also been approved to treat chronic fecal incontinence in patients who have failed or are not candidates for more conservative treatments.

A. Implantation of Sacral Neuromodulation System

Currently, SNM qualification has a trial phase, and is followed if successful by a permanent implant. The trial phase is a test stimulation period where the patient is allowed to evaluate whether the therapy is effective. Typically, there are two techniques that are utilized to perform the test stimulation. The first is an office-based procedure termed the Percutaneous Nerve Evaluation (PNE) and the other is a staged trial.

In the PNE, a foramen needle is typically used first to identify the optimal stimulation location, usually at the S3 level, and to evaluate the integrity of the sacral nerves. Motor and sensory responses are used to verify correct needle placement, as described in Table 1 below. A temporary stimulation lead (a unipolar electrode) is then placed near the sacral nerve under local anesthesia. This procedure can be performed in an office setting without fluoroscopy. The temporary lead is then connected to an external pulse generator (EPG) taped onto the skin of the patient during the trial phase. The stimulation level can be adjusted to provide an optimal comfort level for the particular patient. The patient will monitor his or her voiding for 3 to 7 days to see if there is any symptom improvement. The advantage of the PNE is that it is an incision free procedure that can be performed in the physician's office using local anesthesia. The disadvantage is that the temporary lead is not securely anchored in place and has the propensity to migrate away from the nerve with physical activity and thereby cause failure of the therapy. If a patient fails this trial test, the physician may still recommend the staged trial as described below. If the PNE trial is positive, the temporary trial lead is removed and a permanent quadri-polar tined lead is implanted along with an IPG under general anesthesia.

Figure 3A:
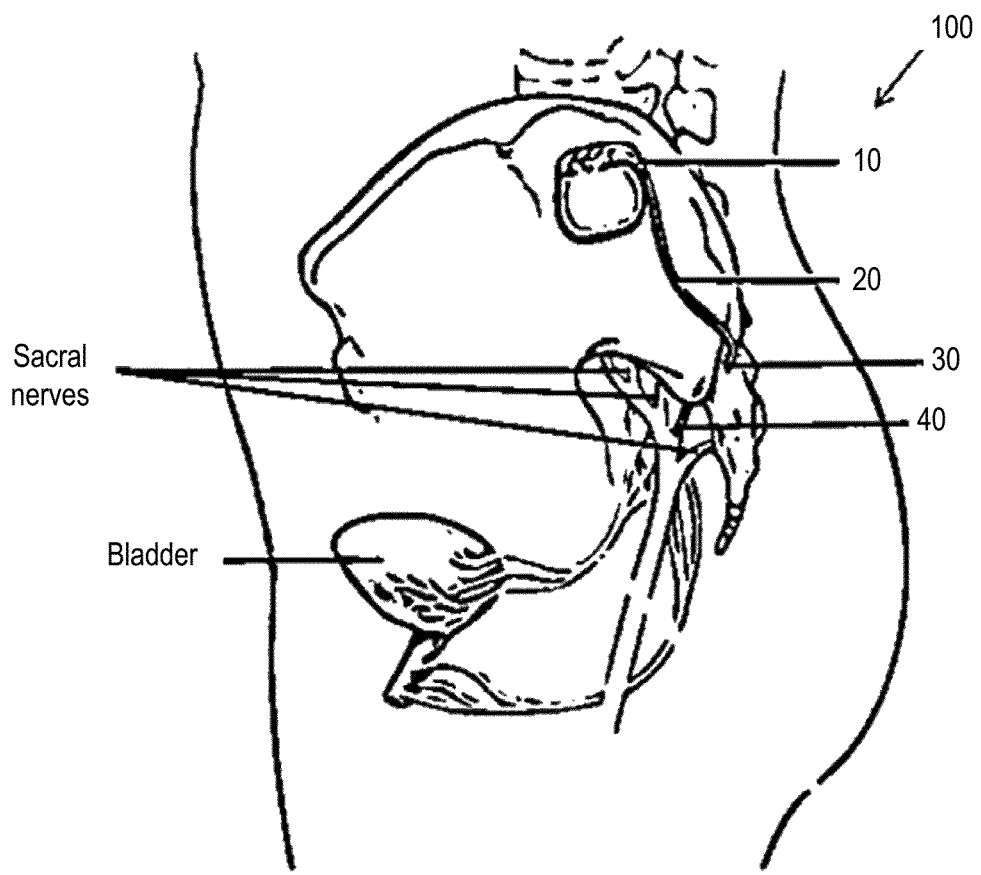
FIG. 3A shows an example of a fully implanted neurostimulation system in accordance with aspects of the invention.

A staged trial involves the implantation of the permanent quadri-polar tined stimulation lead into the patient from the start. It also requires the use of a foramen needle to identify the nerve and optimal stimulation location. The lead is implanted near the S3 sacral nerve and is connected to an EPG via a lead extension. This procedure is performed under fluoroscopic guidance in an operating room and under local or general anesthesia. The EPG is adjusted to provide an optimal comfort level for the patient and the patient monitors his or her voiding for up to two weeks. If the patient obtains meaningful symptom improvement, he or she is considered a suitable candidate for permanent implantation of the IPG under general anesthesia, typically in the upper buttock area, as shown in FIGS. 1 and 3A.

In regard to measuring outcomes for SNM treatment of voiding dysfunction, the voiding dysfunction indications (e.g., urge incontinence, urgency-frequency, and non-obstructive urinary retention) are evaluated by unique primary voiding diary variables. The therapy outcomes are measured using these same variables. SNM therapy is considered successful if a minimum of 50% improvement occurs in any of primary voiding diary variables compared with the baseline. For urge incontinence patients, these voiding diary variables may include: number of leaking episodes per day, number of heavy leaking episodes per day, and number of pads used per day. For patients with urgency-frequency, primary voiding diary variables may include: number of voids per day, volume voided per void and degree of urgency experienced before each void. For patients with retention, primary voiding diary variables may include: catheterized volume per catheterization and number of catheterizations per day. For fecal incontinence patients, the outcome measures captured by the voiding diary include: number of leaking episodes per week, number of leaking days per week, and degree of urgency experienced before each leak.

The mechanism of action of SNM is multifactorial and impacts the neuro-axis at several different levels. In patients with OAB, it is believed that pelvic and/or pudendal afferents can activate the inhibitory reflexes that promote bladder storage by inhibiting the afferent limb of an abnormal voiding reflex. This blocks input to the pontine micturition center, thereby restricting involuntary detrusor contractions without interfering with normal voiding patterns. For patients with urinary retention, SNM is believed to activate the pelvic and/or pudendal nerve afferents originating from the pelvic organs into the spinal cord. At the level of the spinal cord, these afferents may turn on voiding reflexes by suppressing exaggerated guarding reflexes, thus relieving symptoms of patients with urinary retention so normal voiding can be facilitated. In patients with fecal incontinence, it is hypothesized that SNM stimulates pelvic and/or pudendal afferent somatic fibers that inhibit colonic propulsive activity and activates the internal anal sphincter, which in turn improves the symptoms of fecal incontinence patients.

The present invention relates to a system adapted to deliver neurostimulation to targeted nerve tissues in a manner that results in partial or complete activation of the target nerve fibers, causes the augmentation or inhibition of neural activity in nerves, potentially the same or different than the

TABLE 1

Motor and Sensory Responses of SNM at Different Sacral Nerve Roots

| | Response | | |
|---|---|---|---|
| Nerve Innervation | Pelvic Floor | Foot/calf/leg | Sensation |
| S2 -Primary somatic contributor of pudendal nerve for external sphincter, leg, foot | "Clamp" * of anal sphincter | Leg/hip rotation, plantar flexion of entire foot, contraction of calf | Contraction of base of penis, vagina |
| S3 - Virtually all pelvic autonomic functions and striated mucle (levetor ani) | "bellows" ** of perineum | Plantar flexion of great toe, occasionally other toes | Pulling in rectum, extending forward to scrotum or labia |
| S4 - Pelvic autonomic and somatic; No leg pr foot | "bellows" ** | No lower extremity motor stimulation | Pulling in rectum only |

* Clamp: contraction of anal sphincter and, in males, retraction of base of penis. Move buttocks aside and look for anterior/posterior shortening of the perineal structures.
** Bellows: lifting and dropping of pelvic floor. Look for deepening and flattening of buttock groove stimulation target, that control the organs and structures associated with bladder and bowel function.

B. EMG Assisted Neurostimulation Lead Placement and Programming

While conventional sacral nerve stimulation approaches have shown efficacy in treatment of bladder and bowel related dysfunctions, there exists a need to improve positioning of the neurostimulation leads and consistency between the trial and permanent implantation positions of the lead as well as to improve methods of programming. Neurostimulation relies on consistently delivering therapeutic stimulation from a pulse generator, via one or more neurostimulation electrodes, to particular nerves or targeted regions. The neurostimulation electrodes are provided on a distal end of an implantable lead that can be advanced through a tunnel formed in patient tissue. Implantable neurostimulation systems provide patients with great freedom and mobility, but it may be easier to adjust the neurostimulation electrodes of such systems before they are surgically implanted. It is desirable for the physician to confirm that the patient has desired motor and/or sensory responses before implanting an IPG. For at least some treatments (including treatments of at least some forms of urinary and/or fecal dysfunction), demonstrating appropriate motor responses may be highly beneficial for accurate and objective lead placement while the sensory response may not be required or not available (e.g., patient is under general anesthesia).

Placement and calibration of the neurostimulation electrodes and implantable leads sufficiently close to specific nerves can be beneficial for the efficacy of treatment. Accordingly, aspects and embodiments of the present disclosure are directed to aiding and refining the accuracy and precision of neurostimulation electrode placement. Further, aspects and embodiments of the present disclosure are directed to aiding and refining protocols for setting therapeutic treatment signal parameters for a stimulation program implemented through implanted neurostimulation electrodes.

Prior to implantation of the permanent device, patients may undergo an initial testing phase to estimate potential response to treatment. As discussed above, PNE may be done under local anesthesia, using a test needle to identify the appropriate sacral nerve(s) according to a subjective sensory response by the patient. Other testing procedures can involve a two-stage surgical procedure, where a quadripolar tined lead is implanted for a testing phase (Stage 1) to determine if patients show a sufficient reduction in symptom frequency, and if appropriate, proceeding to the permanent surgical implantation of a neuromodulation device. For testing phases and permanent implantation, determining the location of lead placement can be dependent on subjective qualitative analysis by either or both of a patient or a physician.

In exemplary embodiments, determination of whether or not an implantable lead and neurostimulation electrode is located in a desired or correct location can be accomplished through use of electromyography ("EMG"), also known as surface electromyography. EMG, is a technique that uses an EMG system or module to evaluate and record electrical activity produced by muscles, producing a record called an electromyogram. EMG detects the electrical potential generated by muscle cells when those cells are electrically or neurologically activated. The signals can be analyzed to detect activation level or recruitment order. EMG can be performed through the skin surface of a patient, intramuscularly or through electrodes disposed within a patient near target muscles, or using a combination of external and internal structures. When a muscle or nerve is stimulated by an electrode, EMG can be used to determine if the related muscle is activated, (i.e. whether the muscle fully contracts, partially contracts, or does not contract) in response to the stimulus. Accordingly, the degree of activation of a muscle can indicate whether an implantable lead or neurostimulation electrode is located in the desired or correct location on a patient. Further, the degree of activation of a muscle can indicate whether a neurostimulation electrode is providing a stimulus of sufficient strength, amplitude, frequency, or duration to affect a treatment regimen on a patient. Thus, use of EMG provides an objective and quantitative means by which to standardize placement of implantable leads and neurostimulation electrodes, reducing the subjective assessment of patient sensory responses.

In some approaches, positional titration procedures may optionally be based in part on a paresthesia or pain-based subjective response from a patient. In contrast, EMG triggers a measurable and discrete muscular reaction. As the efficacy of treatment often relies on precise placement of the neurostimulation electrodes at target tissue locations and the consistent, repeatable delivery of neurostimulation therapy, using an objective EMG measurement can substantially improve the utility and success of SNM treatment. The measurable muscular reaction can be a partial or a complete muscular contraction, including a response below the triggering of an observable motor response, such as those shown in Table 1, depending on the stimulation of the target muscle. In addition, by utilizing a trial system that allows the neurostimulation lead to remain implanted for use in the permanently implanted system, the efficacy and outcome of the permanently implanted system is more consistent with the results of the trial period, which moreover leads to improved patient outcomes.

C. Example System Embodiments

FIG. 1 schematically illustrates example nerve stimulation system setups, which includes a setup for use in a trial neurostimulation system 200 and a setup for use in a permanently implanted neurostimulation system 100, in accordance with aspects of the invention. The EPG 80 and IPG 50 are each compatible with and wirelessly communicate with a clinician programmer (CP) 60 and a patient remote 70, which are used in positioning and/or programming the trial neurostimulation system 200 and/or permanently implanted system 100 after a successful trial. As discussed above, the system utilizes a cable set and EMG sensor patches in the trial system setup 100 to facilitate lead placement and neurostimulation programming. CP can include specialized software, specialized hardware, and/or both, to aid in lead placement, programming, re-programming, stimulation control, and/or parameter setting. In addition, each of the IPG and the EPG allows the patient at least some control over stimulation (e.g., initiating a pre-set program, increasing or decreasing stimulation), and/or to monitor battery status with the patient remote. This approach also allows for an almost seamless transition between the trial system and the permanent system.

In one aspect, the CP 60 is used by a physician to adjust the settings of the EPG and/or IPG while the lead is implanted within the patient. The CP can be a tablet computer used by the clinician to program the IPG, or to control the EPG during the trial period. The CP can also include capability to record stimulation-induced electromyograms to facilitate lead placement and programming. The patient remote 70 can allow the patient to turn the stimulation on or off, or to vary stimulation from the IPG while implanted, or from the EPG during the trial phase.

In another aspect, the CP 60 has a control unit which can include a microprocessor and specialized computer-code instructions for implementing methods and systems for use by a physician in deploying the treatment system and setting up treatment parameters. The CP generally includes a graphical user interface, an EMG module, an EMG input that can couple to an EMG output stimulation cable, an EMG stimulation signal generator, and a stimulation power source. The stimulation cable can further be configured to couple to any or all of an access device (e.g., a foramen needle), a treatment lead of the system, or the like. The EMG input may be configured to be coupled with one or more sensory patch electrode(s) for attachment to the skin of the patient adjacent a muscle (e.g., a muscle enervated by a target nerve). Other connectors of the CP may be configured for coupling with an electrical ground or ground patch, an electrical pulse generator (e.g., an EPG or an IPG), or the like. As noted above, the CP can include a module with hardware and computer-code to execute EMG analysis, where the module can be a component of the control unit microprocessor, a pre-processing unit coupled to or in-line with the stimulation and/or sensory cables, or the like.

In other aspects, the CP 60 allows the clinician to read the impedance of each electrode contact whenever the lead is connected to an EPG, an IPG or a CP to ensure reliable connection is made and the lead is intact. This may be used as an initial step in both positioning the lead and in programming the leads to ensure the electrodes are properly functioning. The CP 60 is also able to save and display previous (e.g., up to the last four) programs that were used by a patient to help facilitate re-programming. In some embodiments, the CP 60 further includes a USB port for saving reports to a USB drive and a charging port. The CP is configured to operate in combination with an EPG when placing leads in a patient body as well with the IPG during programming. The CP can be electronically coupled to the EPG during test simulation through a specialized cable set or through wireless communication, thereby allowing the CP to configure, modify, or otherwise program the electrodes on the leads connected to the EPG. The CP may also include physical on/off buttons to turn the CP on and off and/or to turn stimulation on and off.

The electrical pulses generated by the EPG and IPG are delivered to one or more targeted nerves via one or more neurostimulation electrodes at or near a distal end of each of one or more leads. The leads can have a variety of shapes, can be a variety of sizes, and can be made from a variety of materials, which size, shape, and materials can be tailored to the specific treatment application. While in this embodiment, the lead is of a suitable size and length to extend from the IPG and through one of the foramen of the sacrum to a targeted sacral nerve, in various other applications, the leads may be, for example, implanted in a peripheral portion of the patient's body, such as in the arms or legs, and can be configured to deliver electrical pulses to the peripheral nerve such as may be used to relieve chronic pain. It is appreciated that the leads and/or the stimulation programs may vary according to the nerves being targeted.

Figure 2A:
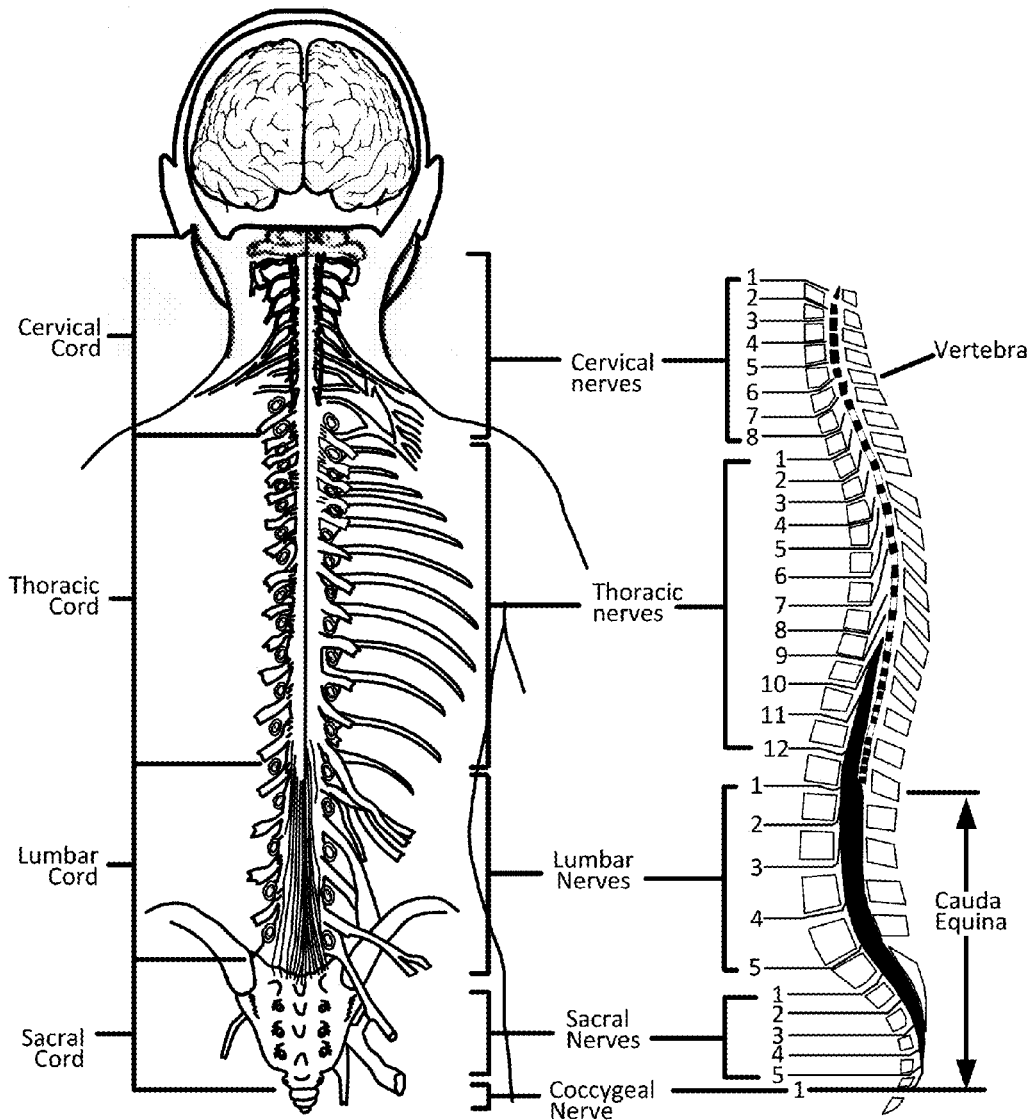
FIGS. 2A-2C show diagrams of the nerve structures along the spine, the lower back and sacrum region, which may be stimulated in accordance with aspects of the invention.
Figure 2B:
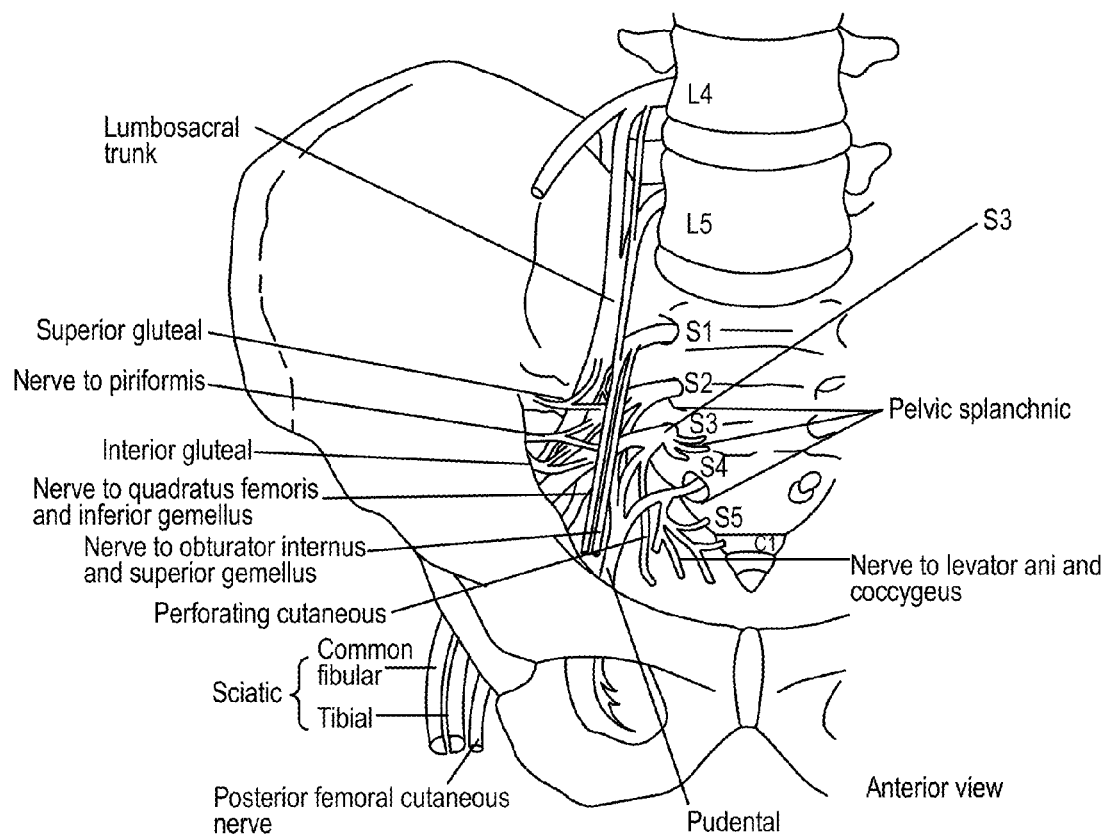
Figure 2C:
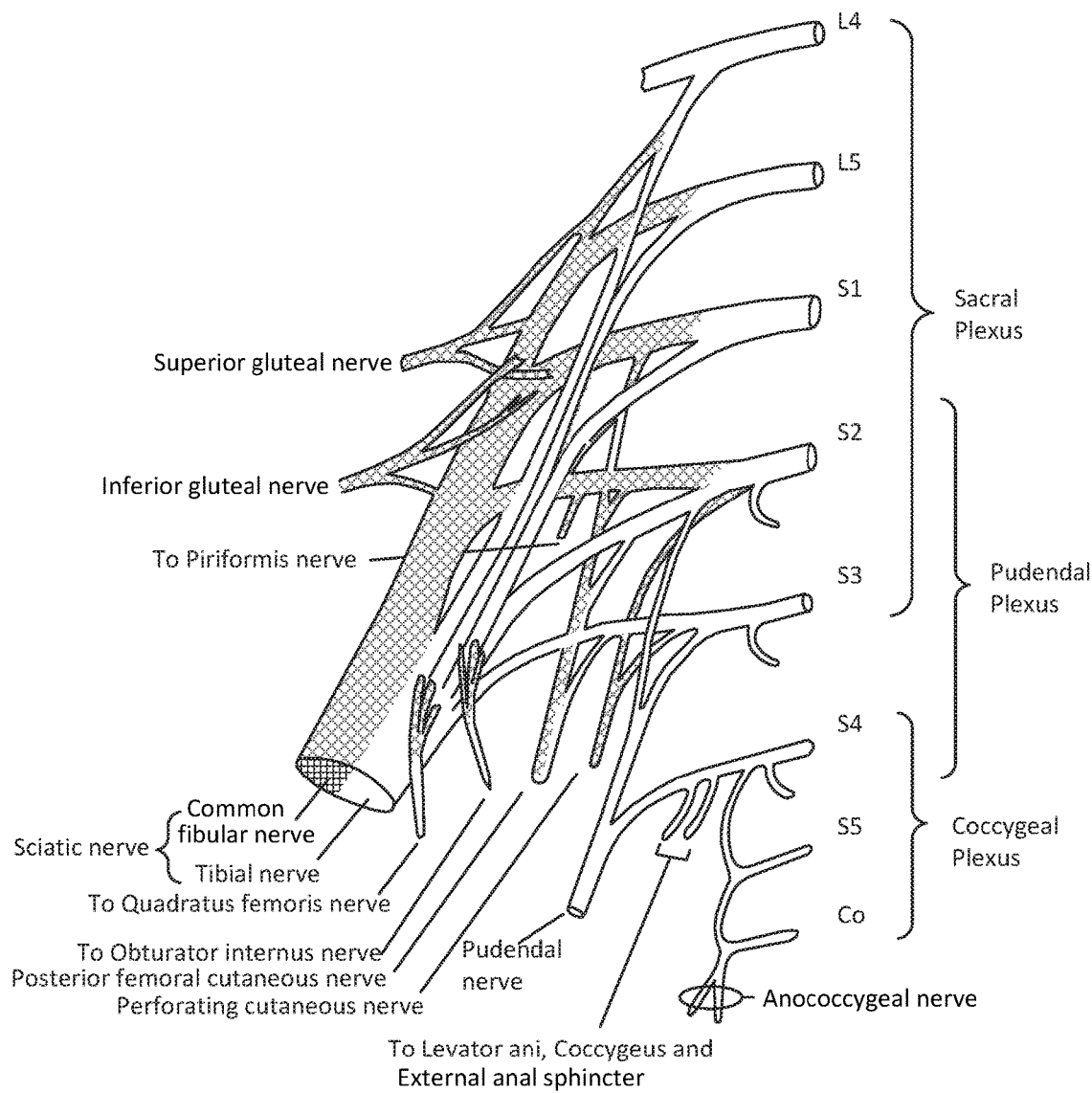

FIGS. 2A-2C show diagrams of various nerve structures of a patient, which may be used in neurostimulation treatments, in accordance with aspects of the invention. FIG. 2A shows the different sections of the spinal cord and the corresponding nerves within each section. The spinal cord is a long, thin bundle of nerves and support cells that extend from the brainstem along the cervical cord, through the thoracic cord and to the space between the first and second lumbar vertebra in the lumbar cord. Upon exiting the spinal cord, the nerve fibers split into multiple branches that innervate various muscles and organs transmitting impulses of sensation and control between the brain and the organs and muscles. Since certain nerves may include branches that innervate certain organs, such as the bladder, and branches that innervate certain muscles of the leg and foot, stimulation of the nerve at or near the nerve root near the spinal cord can stimulate the nerve branch that innervate the targeted organ, which may also result in muscle responses associated with the stimulation of the other nerve branch. Thus, by monitoring for certain muscle responses, such as those in Table 1, either visually, through the use of EMG as described herein or both, the physician can determine whether the targeted nerve is being stimulated. While stimulation at a certain level may evoke robust muscle responses visible to the naked eye, stimulation at a lower level (e.g. sub-threshold) may still provide activation of the nerve associated with the targeted organ while evoking no corresponding muscle response or a response only visible with EMG. In some embodiments, this low level stimulation also does not cause any paresthesia. This is advantageous as it allows for treatment of the condition by neurostimulation without otherwise causing patient discomfort, pain or undesired muscle responses.

FIG. 2B shows the nerves associated with the lower back section, in the lower lumbar cord region where the nerve bundles exit the spinal cord and travel through the sacral foramens of the sacrum. In some embodiments, the neurostimulation lead is advanced through the foramen until the neurostimulation electrodes are positioned at the anterior sacral nerve root, while the anchoring portion of the lead proximal of the stimulation electrodes are generally disposed dorsal of the sacral foramen through which the lead passes, so as to anchor the lead in position. FIG. 2C shows detail views of the nerves of the lumbosacral trunk and the sacral plexus, in particular, the S1-S5 nerves of the lower sacrum. The S3 sacral nerve is of particular interest for treatment of bladder related dysfunction, and in particular OAB.

FIG. 3A schematically illustrates an example of a fully implanted neurostimulation system 100 adapted for sacral nerve stimulation. Neurostimulation system 100 includes an IPG implanted in a lower back region and connected to a neurostimulation lead extending through the S3 foramen for stimulation of the S3 sacral nerve. The lead is anchored by a tined anchor portion 30 that maintains a position of a set of neurostimulation electrodes 40 along the targeted nerve, which in this example, is the anterior sacral nerve root S3 which enervates the bladder so as to provide therapy for various bladder related dysfunctions. While this embodiment is adapted for sacral nerve stimulation, it is appreciated that similar systems can be used in treating patients with, for example, chronic, severe, refractory neuropathic pain originating from peripheral nerves or various urinary dysfunctions or still further other indications. Implantable neurostimulation systems can be used to either stimulate a target peripheral nerve or the posterior epidural space of the spine.

Properties of the electrical pulses can be controlled via a controller of the implanted pulse generator. In some embodiments, these properties can include, for example, the frequency, amplitude, pattern, duration, or other aspects of the electrical pulses. These properties can include, for example, a voltage, a current, or the like. This control of the electrical pulses can include the creation of one or more electrical pulse programs, plans, or patterns, and in some embodiments, this can include the selection of one or more pre-existing electrical pulse programs, plans, or patterns. In the embodiment depicted in FIG. 3A, the implantable neurostimulation system 100 includes a controller in the IPG having one or more pulse programs, plans, or patterns that may be pre-programmed or created as discussed above. In some embodiments, these same properties associated with the IPG may be used in an EPG of a partly implanted trial system used before implantation of the permanent neurostimulation system 100.

FIG. 3B shows a schematic illustration of a trial neurostimulation system 200 utilizing an EPG patch 81 adhered to the skin of a patient, particularly to the abdomen of a patient, the EPG 80 being encased within the patch. In one aspect, the lead is hardwired to the EPG, while in another the lead is removably coupled to the EPG through a port or aperture in the top surface of the flexible patch 81. Excess lead can be secured by an additional adherent patch. In one aspect, the EPG patch is disposable such that the lead can be disconnected and used in a permanently implanted system without removing the distal end of the lead from the target location. Alternatively, the entire system can be disposable and replaced with a permanent lead and IPG. When the lead of the trial system is implanted, an EMG obtained via the CP using one or more sensor patches can be used to ensure that the leads are placed at a location proximate to the target nerve or muscle, as discussed previously.

In some embodiments, the trial neurostimulation system utilizes an EPG 80 within an EPG patch 81 that is adhered to the skin of a patient and is coupled to the implanted neurostimulation lead 20 through a lead extension 22, which is coupled with the lead 20 through a connector 21. This extension and connector structure allows the lead to be extended so that the EPG patch can be placed on the abdomen and allows use of a lead having a length suitable for permanent implantation should the trial prove successful. This approach may utilize two percutaneous incisions, the connector provided in the first incision and the lead extensions extending through the second percutaneous incision, there being a short tunneling distance (e.g., about 10 cm) there between. This technique may also minimize movement of an implanted lead during conversion of the trial system to a permanently implanted system.

In one aspect, the EPG unit is wirelessly controlled by a patient remote and/or the CP in a similar or identical manner as the IPG of a permanently implanted system. The physician or patient may alter treatment provided by the EPG through use of such portable remotes or programmers and the treatments delivered are recorded on a memory of the programmer for use in determining a treatment suitable for use in a permanently implanted system. The CP can be used in lead placement, programming and/or stimulation control in each of the trial and permanent nerve stimulation systems. In addition, each nerve stimulation system allows the patient to control stimulation or monitor battery status with the patient remote. This configuration is advantageous as it allows for an almost seamless transition between the trial system and the permanent system. From the patient's viewpoint, the systems will operate in the same manner and be controlled in the same manner, such that the patient's subjective experience in using the trial system more closely matches what would be experienced in using the permanently implanted system. Thus, this configuration reduces any uncertainties the patient may have as to how the system will operate and be controlled such that the patient will be more likely to convert a trial system to a permanent system.

As shown in the detailed view of FIG. 3B, the EPG 80 is encased within a flexible laminated patch 81, which include an aperture or port through which the EPG 80 is connected to the lead extension 22. The patch may further an "on/off" button 83 with a molded tactile detail to allow the patient to turn the EPG on and/or off through the outside surface of the adherent patch 81. The underside of the patch 81 is covered with a skin-compatible adhesive 82 for continuous adhesion to a patient for the duration of the trial period. For example, a breathable strip having skin-compatible adhesive 82 would allow the EPG 80 to remain attached to the patient continuously during the trial, which may last over a week, typically two weeks to four weeks, or even longer.

Figure 4:
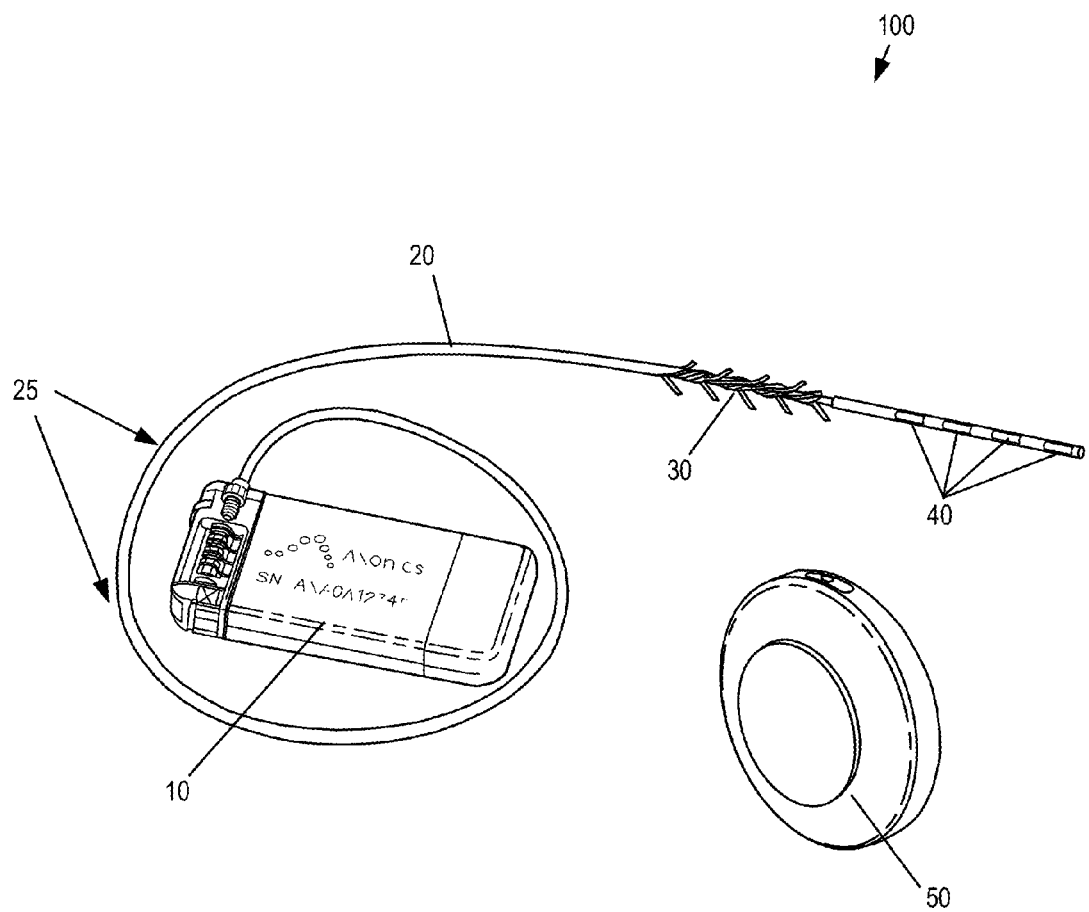
FIG. 4 shows an example of a neurostimulation system having an implantable stimulation lead, an implantable pulse generator, and an external charging device, in accordance with aspects of the invention.

FIG. 4 illustrates an example neurostimulation system 100 that is fully implantable and adapted for sacral nerve stimulation treatment. The implantable system 100 includes an IPG 10 that is coupled to a neurostimulation lead 20 that includes a group of neurostimulation electrodes 40 at a distal end of the lead. The lead includes a lead anchor portion 30 with a series of tines extending radially outward so as to anchor the lead and maintain a position of the neurostimulation lead 20 after implantation. The lead 20 may further include one or more radiopaque markers 25 to assist in locating and positioning the lead using visualization techniques such as fluoroscopy. In some embodiments, the IPG provides monopolar or bipolar electrical pulses that are delivered to the targeted nerves through one or more neurostimulation electrodes. In sacral nerve stimulation, the lead is typically implanted through the S3 foramen as described herein.

In one aspect, the IPG is rechargeable wirelessly through conductive coupling by use of a charging device 50 (CD), which is a portable device powered by a rechargeable battery to allow patient mobility while charging. The CD is used for transcutaneous charging of the IPG through RF induction. The CD can either be patched to the patient's skin using an adhesive or can be held in place using a belt 53 or by an adhesive patch 52, such as shown in the schematic of FIG. 1. The CD may be charged by plugging the CD directly into an outlet or by placing the CD in a charging dock or station 51 that connects to an AC wall outlet or other power source.

The system may further include a patient remote 70 and CP 60, each configured to wirelessly communicate with the implanted IPG, or with the EPG during a trial, as shown in the schematic of the nerve stimulation system in FIG. 1. The CP 60 may be a tablet computer used by the clinician to program the IPG and the EPG. The device also has the capability to record stimulation-induced electromyograms (EMGs) to facilitate lead placement, programming, and/or re-programming. The patient remote may be a battery-operated, portable device that utilizes radio-frequency (RF) signals to communicate with the EPG and IPG and allows the patient to adjust the stimulation levels, check the status of the IPG battery level, and/or to turn the stimulation on or off.

Figure 5A:
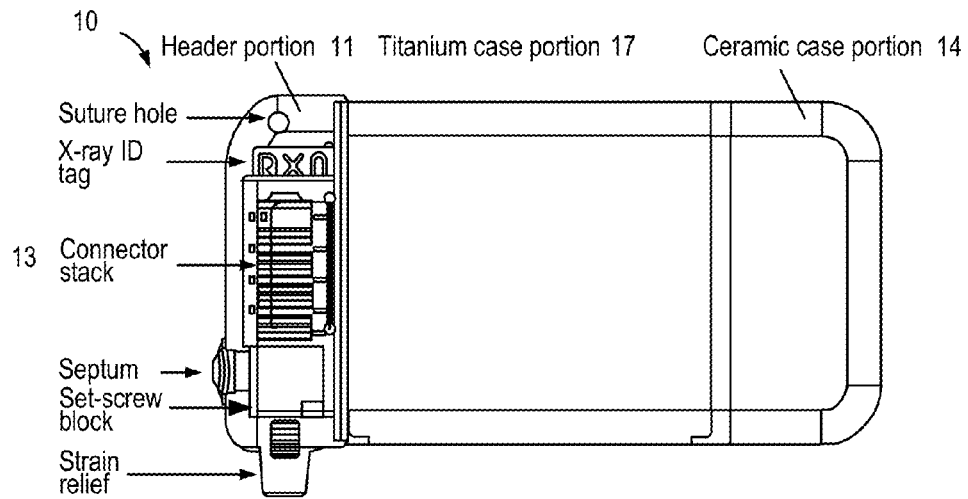
FIGS. 5A-5C show detail views of an implantable pulse generator and associated components for use in a neurostimulation system, in accordance with aspects of the invention.
Figure 5B:
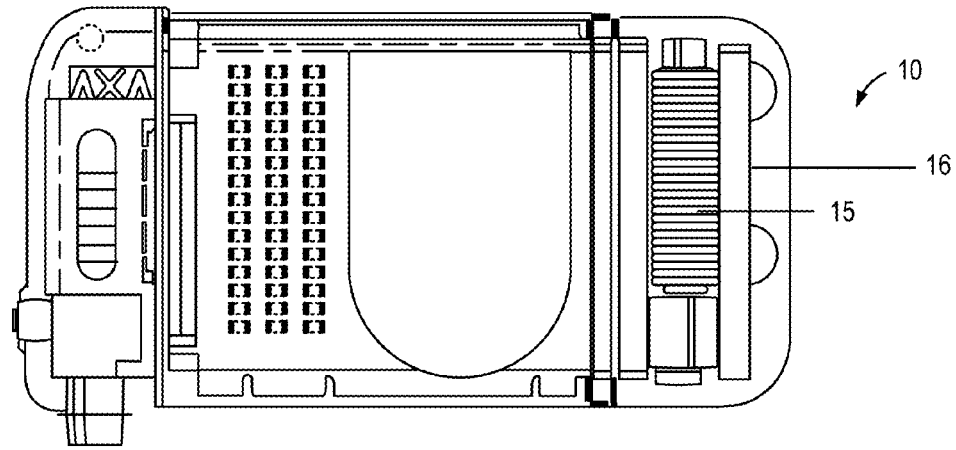
Figure 5C:
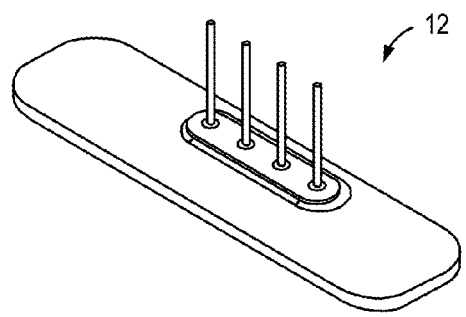

FIG. 5A-5C show detail views of the IPG and its internal components. In some embodiments, the pulse generator can generate one or more non-ablative electrical pulses that are delivered to a nerve to control pain or cause some other desired effect, for example to inhibit, prevent, or disrupt neural activity for the treatment of OAB or bladder related dysfunction. In some applications, the pulses having a pulse amplitude in a range between 0 mA to 1,000 mA, 0 mA to 100 mA, 0 mA to 50 mA, 0 mA to 25 mA, and/or any other or intermediate range of amplitudes may be used. One or more of the pulse generators can include a processor and/or memory adapted to provide instructions to and receive information from the other components of the implantable neurostimulation system. The processor can include a microprocessor, such as a commercially available microprocessor from Intel® or Advanced Micro Devices, Inc.®, or the like. An IPG may include an energy storage feature, such as one or more capacitors, one or more batteries, and typically includes a wireless charging unit.

One or more properties of the electrical pulses can be controlled via a controller of the IPG or EPG. In some embodiments, these properties can include, for example, the frequency, amplitude, pattern, duration, or other aspects of the timing and magnitude of the electrical pulses. These properties can further include, for example, a voltage, a current, or the like. This control of the electrical pulses can include the creation of one or more electrical pulse programs, plans, or patterns, and in some embodiments, this can include the selection of one or more pre-existing electrical pulse programs, plans, or patterns. In one aspect, the IPG 100 includes a controller having one or more pulse programs, plans, or patterns that may be created and/or pre-programmed. In some embodiments, the IPG can be programmed to vary stimulation parameters including pulse amplitude in a range from 0 mA to 10 mA, pulse width in a range from 50 µs to 500 µs, pulse frequency in a range from 5 Hz to 250 Hz, stimulation modes (e.g., continuous or cycling), and electrode configuration (e.g., anode, cathode, or off), to achieve the optimal therapeutic outcome specific to the patient. In particular, this allows for an optimal setting to be determined for each patient even though each parameter may vary from person to person.

As shown in FIGS. 5A-5B, the IPG may include a header portion 11 at one end and a ceramic portion 14 at the opposite end. The header portion 11 houses a feed through assembly 12 and connector stack 13, while the ceramic case portion 14 houses an antennae assembly 16 to facilitate wireless communication with the clinician program, the patient remote, and/or a charging coil to facilitate wireless charging with the CD. The remainder of the IPG is covered with a titanium case portion 17, which encases the printed circuit board, memory and controller components that facilitate the electrical pulse programs described above. In the example shown in FIG. 5C, the header portion of the IPG includes a four-pin feed-through assembly 12 that couples with the connector stack 13 in which the proximal end of the lead is coupled. The four pins correspond to the four electrodes of the neurostimulation lead. In some embodiments, a Balseal® connector block is electrically connected to four platinum/iridium alloy feed-through pins which are brazed to an alumina ceramic insulator plate along with a titanium alloy flange. This feed-through assembly is laser seam welded to a titanium-ceramic brazed case to form a complete hermetic housing for the electronics.

In some embodiment, such as that shown in FIG. 5A, the ceramic and titanium brazed case is utilized on one end of the IPG where the ferrite coil and PCB antenna assemblies are positioned. A reliable hermetic seal is provided via a ceramic-to-metal brazing technique. The zirconia ceramic may comprise a 3Y-TZP (3 mol percent Yttria-stabilized tetragonal Zirconia Polycrystals) ceramic, which has a high flexural strength and impact resistance and has been commercially utilized in a number of implantable medical technologies. It will be appreciated, however, that other ceramics or other suitable materials may be used for construction of the IPG.

In one aspect, utilization of ceramic material provides an efficient, radio-frequency-transparent window for wireless communication with the external patient remote and clinician's programmer as the communication antenna is housed inside the hermetic ceramic case. This ceramic window has further facilitated miniaturization of the implant while maintaining an efficient, radio-frequency-transparent window for long term and reliable wireless communication between the IPG and external controllers, such as the patient remote and CP. The IPG's wireless communication is generally stable over the lifetime of the device, unlike prior art products where the communication antenna is placed in the header outside the hermetic case. The communication reliability of such prior art devices tends to degrade due to the change in dielectric constant of the header material in the human body over time.

In another aspect, the ferrite core is part of the charging coil assembly 15, shown in FIG. 5B, which is positioned inside the ceramic case 14. The ferrite core concentrates the magnetic field flux through the ceramic case as opposed to the metallic case portion 17. This configuration maximizes coupling efficiency, which reduces the required magnetic field and in turn reduces device heating during charging. In particular, because the magnetic field flux is oriented in a direction perpendicular to the smallest metallic cross section area, heating during charging is minimized. This configuration also allows the IPG to be effectively charged at depth of 3 cm with the CD, when positioned on a skin surface of the patient near the IPG and reduces re-charging time.

Figure 6A:
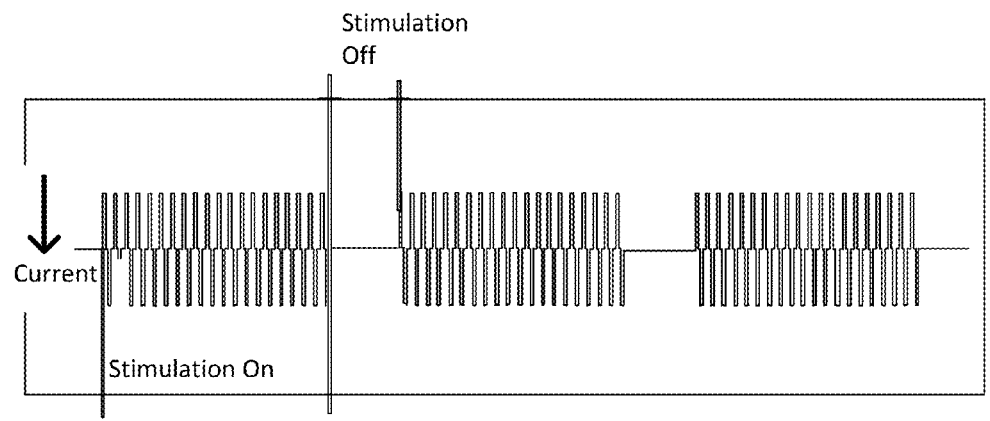
FIGS. 6A-6B show signal characteristics of a neurostimulation program, in accordance with aspects of the invention.
Figure 6B:
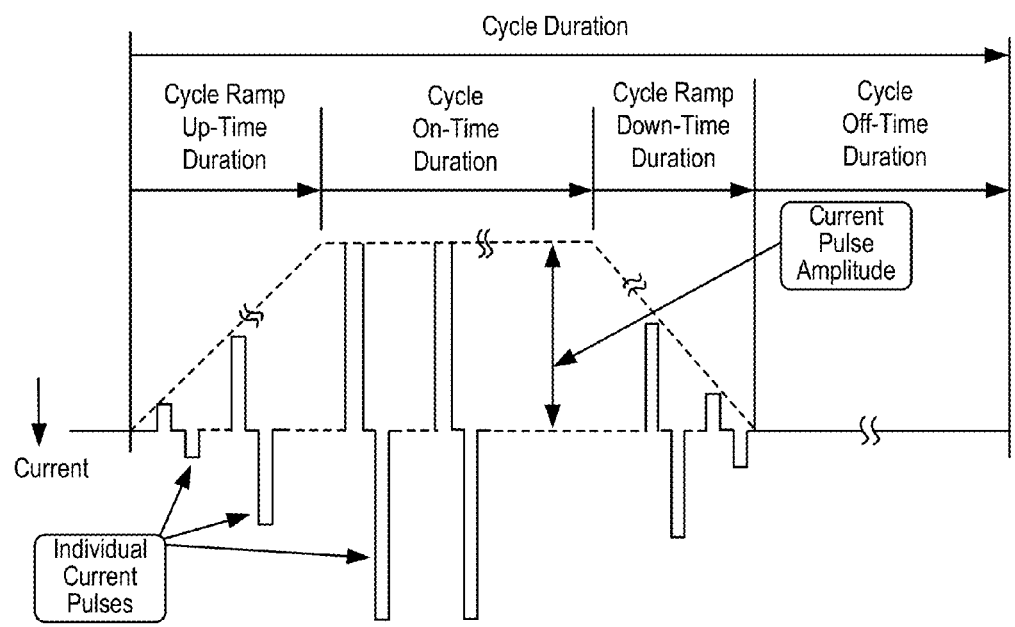

In one aspect, the CP 60 is used to program the IPG/EPG according to various stimulation modes, which can be determined by the CP or selected by the physician using the CP. In some embodiments, the IPG/EPG may be configured with two stimulation modes: continuous mode and cycling mode. The cycling mode saves energy in comparison to the continuous mode, thereby extending the recharge interval of the battery and lifetime of the device. The cycling mode may also help reduce the risk of neural adaptation for some patients. Neural adaptation is a change over time in the responsiveness of the neural system to a constant stimulus. Thus, cycling mode may also mitigate neural adaptation so to provide longer-term therapeutic benefit. FIG. 6A shows an example of stimulation in a cycling mode, in which the duty cycle is the stimulation on time over the stimulation-on time plus the stimulation-off time. In some embodiments, the IPG/EPG is configured with a ramping feature, such as shown in the example of FIG. 6B. In these embodiments, the stimulation signal is ramped up and/or down between the stimulation-on and stimulation-off levels. This feature helps reduce the sudden "jolting" or "shocking" sensation that some patients might experience when the stimulation is initially turned on or at the cycle-on phase during the cycling mode. This feature is particularly of benefit for patients who need relative high stimulation settings and/or for patients who are sensitive to electrical stimulation.

To activate an axon of a nerve fiber, one needs to apply an electric field outside of the axon to create a voltage gradient across its membrane. This can be achieved by pumping charge between the electrodes of a stimulator. Action potentials, which transmit information through the nervous system, are generated when the outside of the nerve is depolarized to a certain threshold, which is determined by the amount of current delivered. To generate continuous action potentials in the axon, this extracellular gradient threshold needs to be reached with the delivery of each stimulation pulse.

In conventional systems, a constant voltage power source is able to maintain the output voltage of the electrodes, so that enough current is delivered to activate the axon at initial implantation. However, during the first several weeks following implantation, tissue encapsulation around electrodes occurs, which results in an impedance (tissue resistance) increase. According to the ohms' law (I=V/R where I is the current, V the voltage and R the tissue impedance of the electrode pair), current delivered by a constant voltage stimulator will therefore decrease, generating a smaller gradient around the nerve. When the impedance reaches a certain value, extracellular depolarization will go down below the threshold value, so that no more action potential can be generated in the axon. Patients will need to adjust the voltage of their system to re-adjust the current, and restore the efficacy of the therapy.

In contrast, embodiments of the present invention utilize a constant current power source. In one aspect, the system uses feedback to adjust the voltage in such a way that the current is maintained regardless of what happens to the impedance (until one hits the compliance limit of the device), so that the gradient field around the nerve is maintained overtime. Using a constant current stimulator keeps delivering the same current that is initially selected regardless the impedance change, for a maintained therapeutic efficacy.

Figure 7:
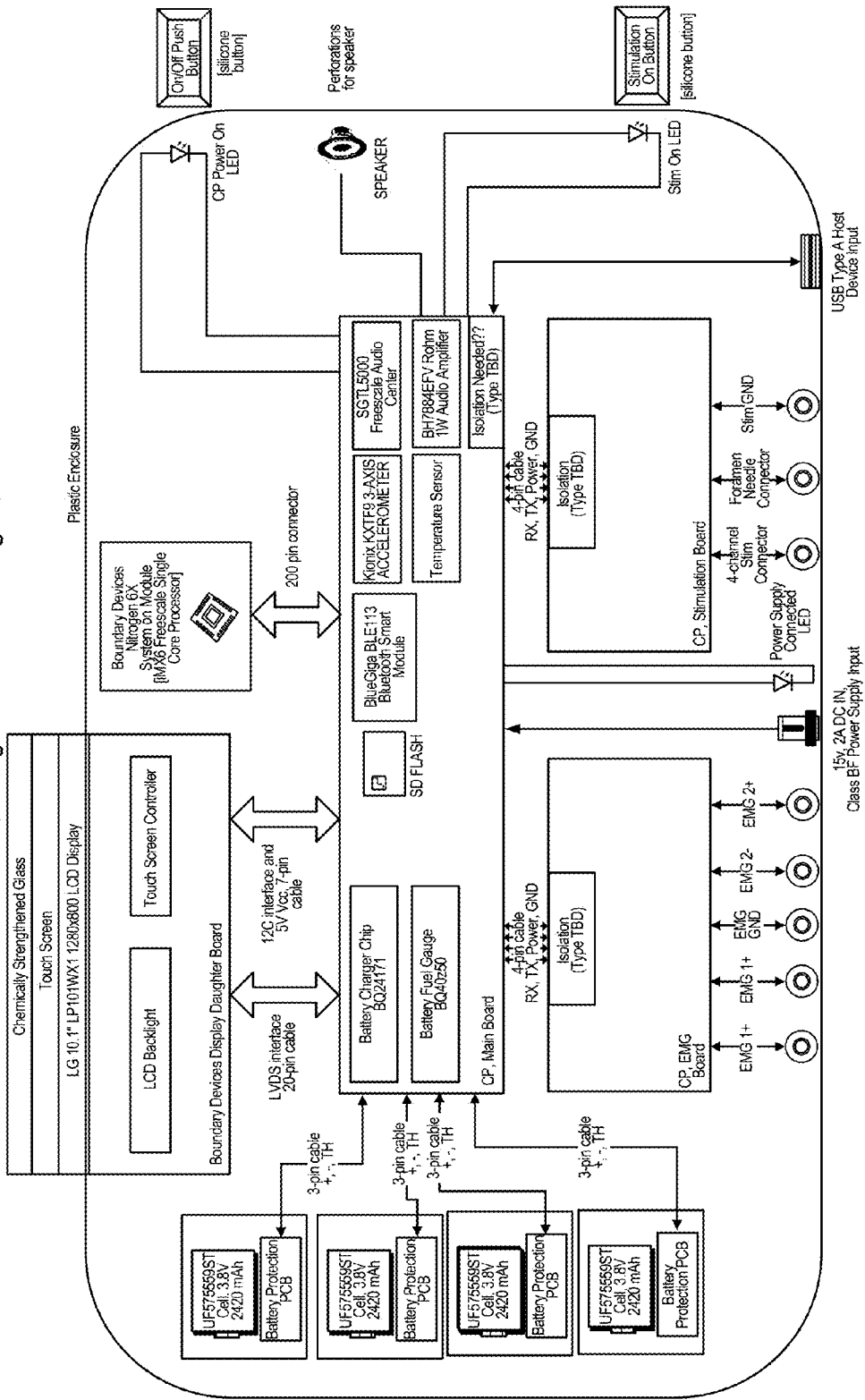
FIG. 7 illustrates a schematic of a clinician programmer configuration, in accordance with aspects of the invention.
Figures 1, 8A:
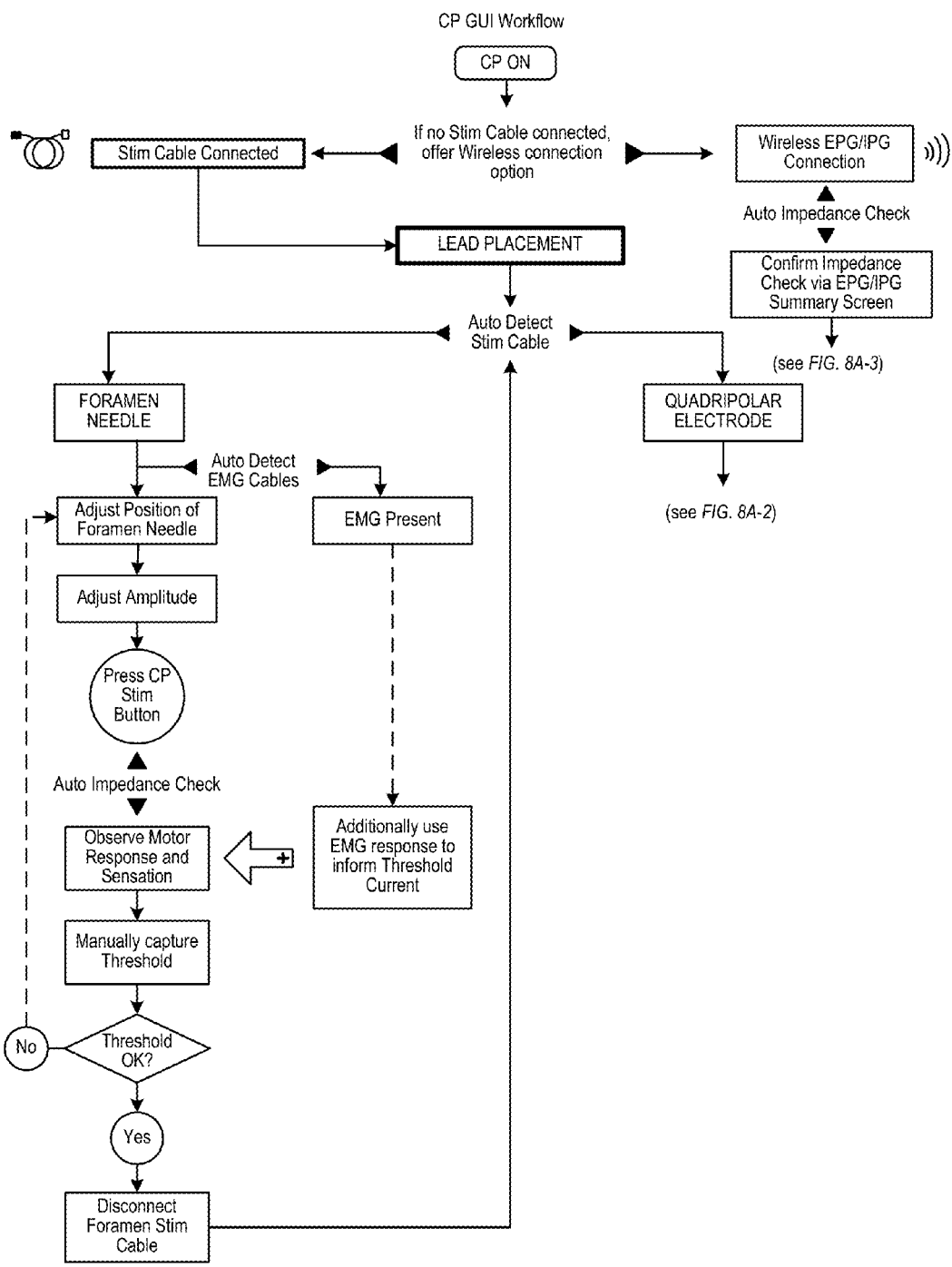
Figures 2, 8A:
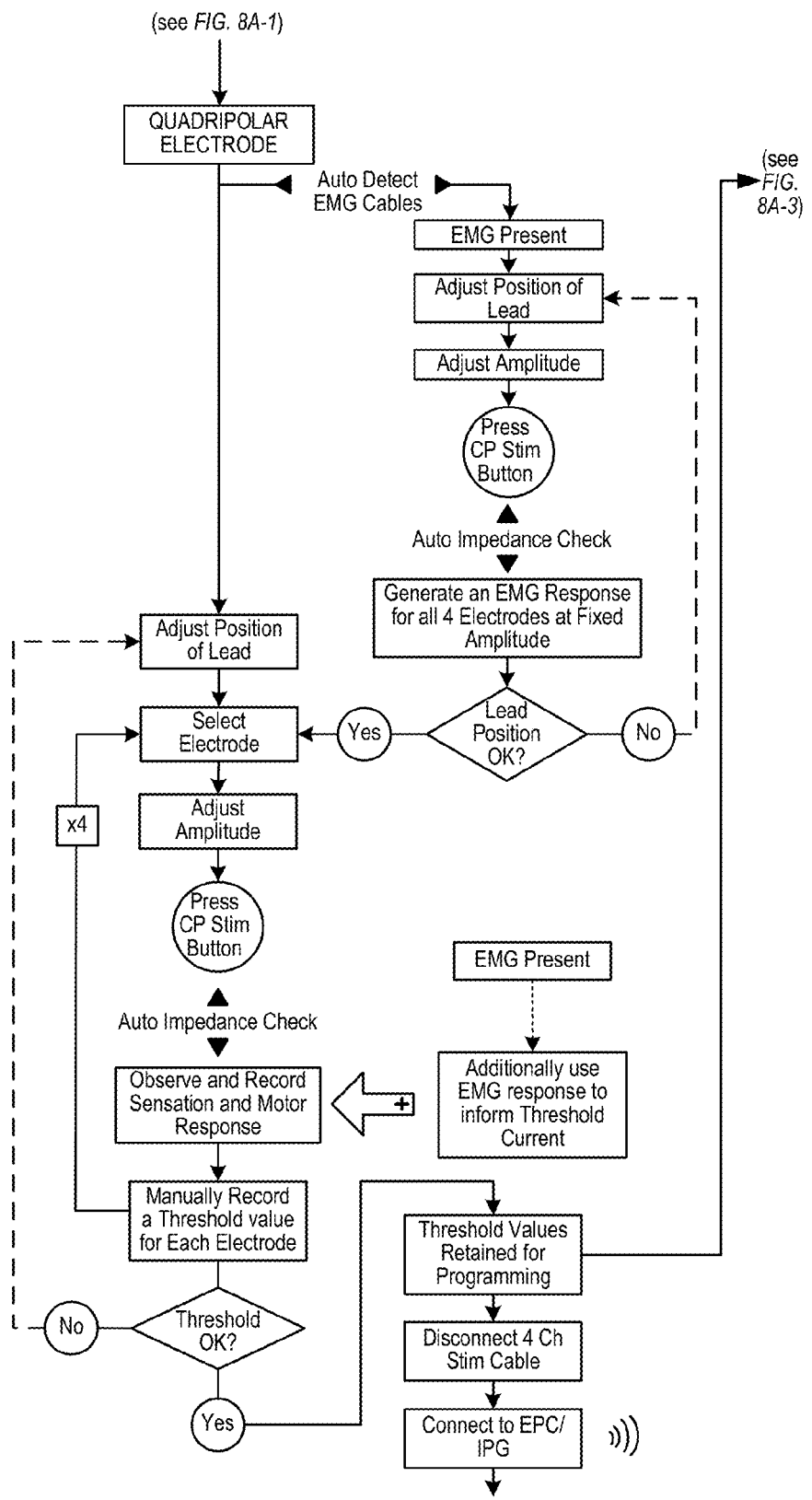
Figures 3, 8A:
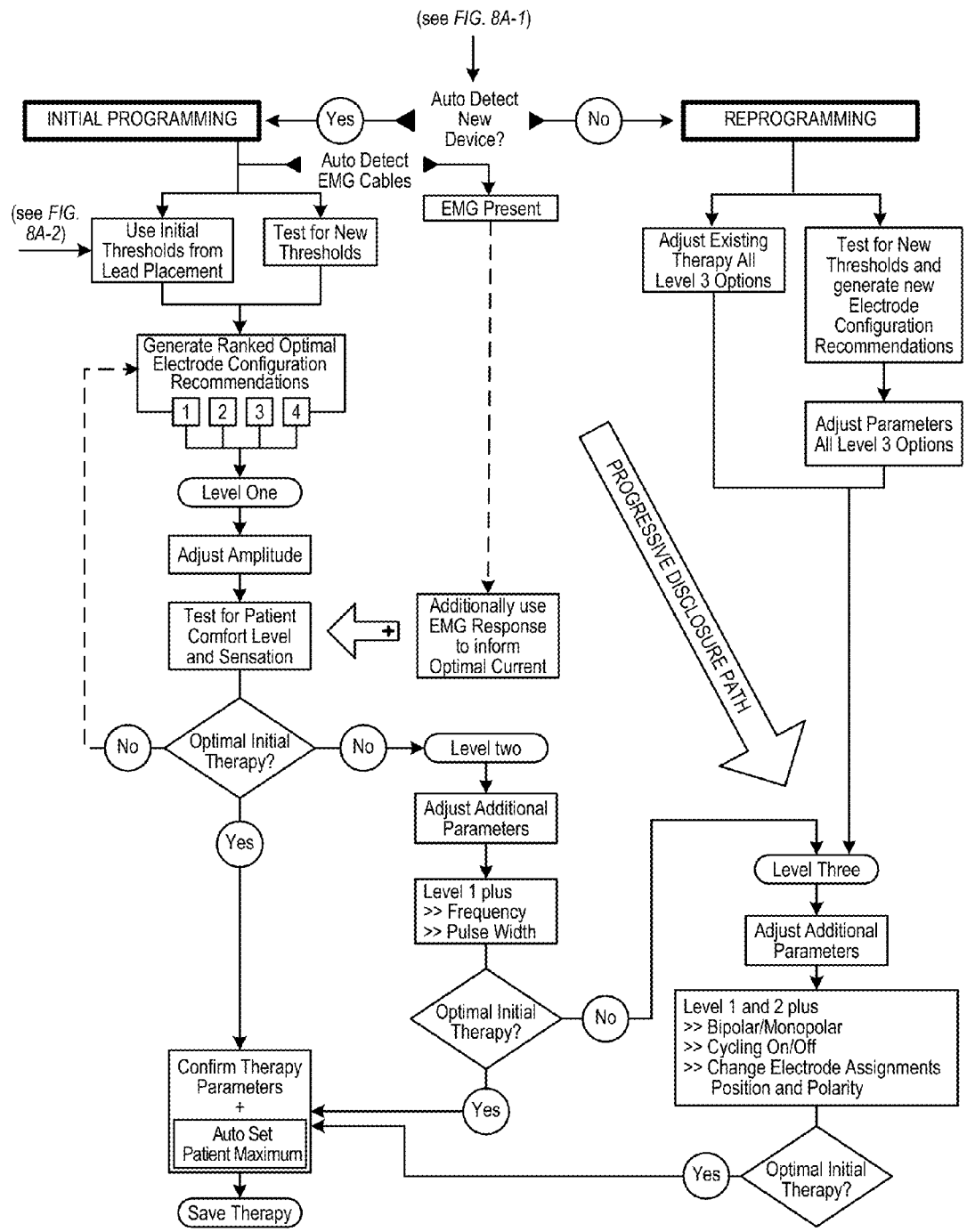
Figure 8B:
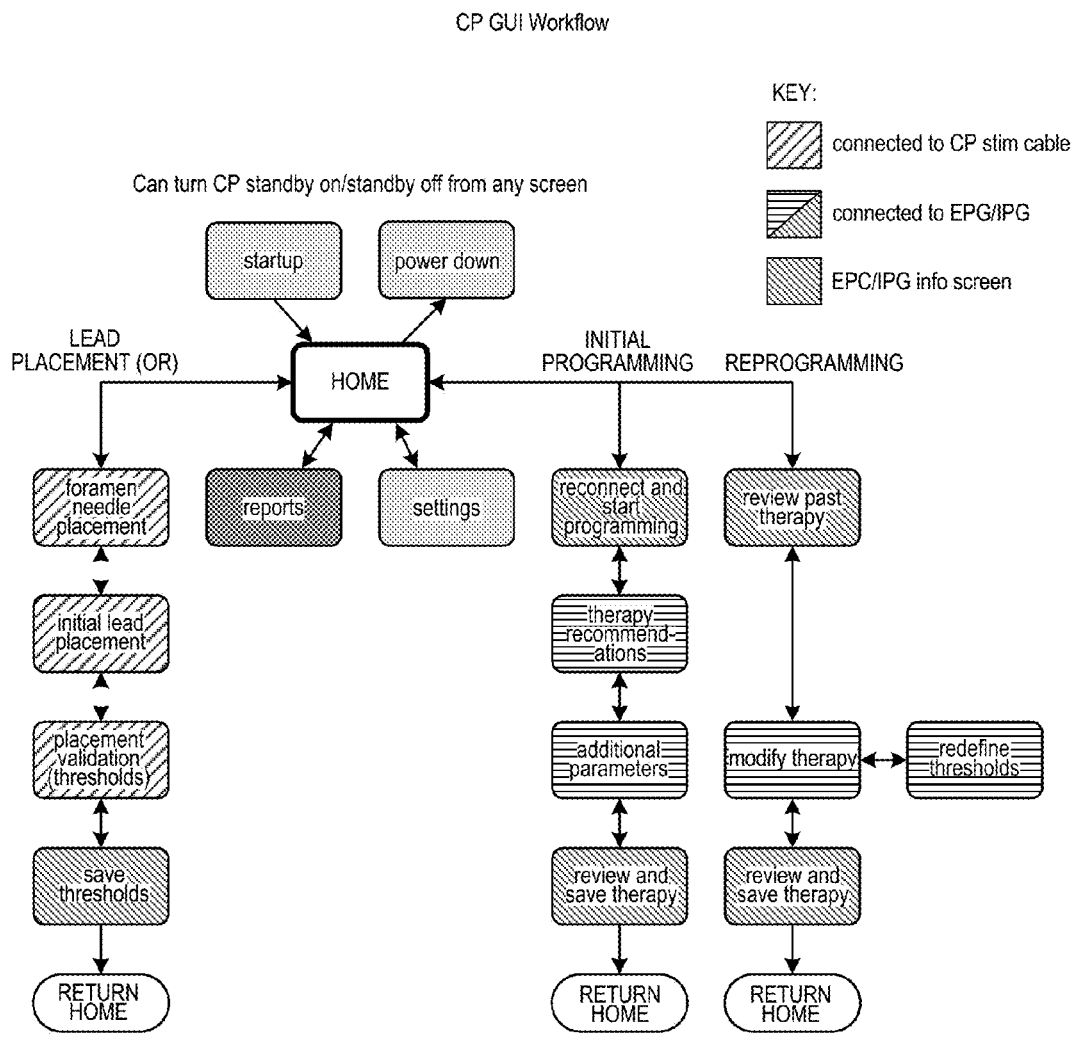

FIG. 7 schematically illustrates a block diagram of the configuration of the CP 60 and associated interfaces and internal components. As described above, CP 60 is typically a tablet computer with software that runs on a standard operating system. The CP 60 includes a communication module, a stimulation module and an EMG sensing module. The communication module communicates with the IPG and/or EPG in the medical implant communication service frequency band for programming the IPG and/or EPG. While this configuration reflects a portable user interface display device, such as a tablet computer, it is appreciated that the CP may be incorporated into various other types of computing devices, such as a laptop, desktop computer, or a standalone terminal for use in a medical facility.

D. Workflows for Lead Placement, Programming and Reprogramming with CP

Figure 9A:
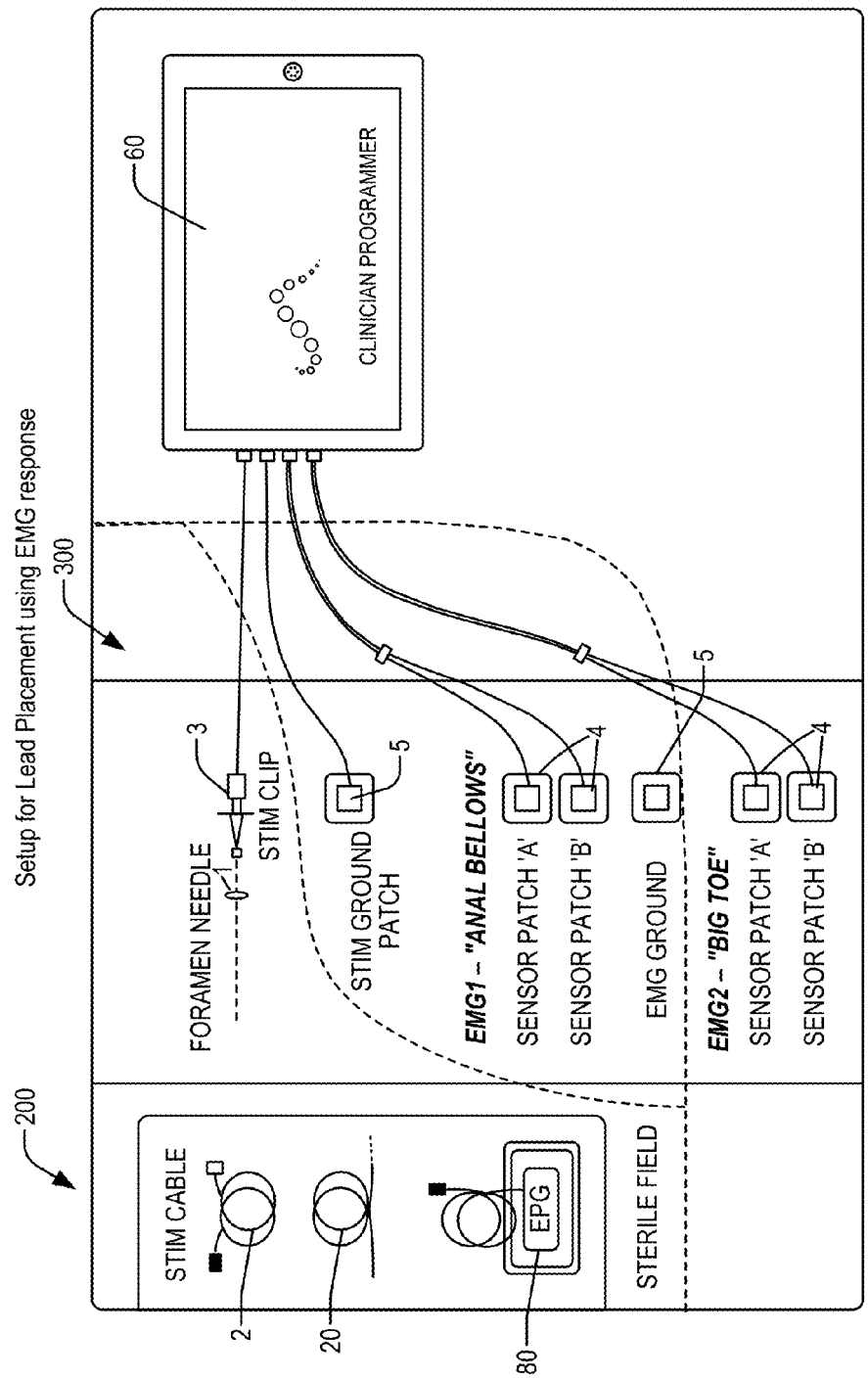
FIG. 9B illustrates electromyography sensor patches.
FIG. 9C illustrates attachment of electromyography sensor patches for big toe response.
FIG. 9D illustrates the anatomy on which electromyography sensor patches are attached to record an anal bellows response, in accordance with aspects of the invention.
FIG. 9E illustrates an example compound muscle action potential response in electromyography and FIG. 9F illustrates a raw EMG trace and processing of electromyography data, in accordance with aspects of the invention.
FIG. 9G illustrates a graphical user interface display on a clinician programmer in a system setup utilizing electromyography for neural localization with a foramen needle, in accordance with aspects of the invention.
Figure 9B:
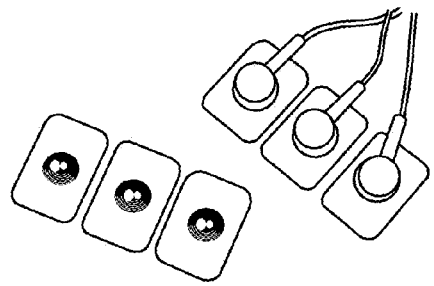

FIGS. 9A-9B illustrate schematics of the workflow used in lead placement and programming of the neurostimulation system using a CP with EMG assist, in accordance with aspects of the invention. FIG. 9A schematically illustrates a detailed overview of the use of a CP having a graphical user interface for lead placement and subsequent programming, which may include initial programming and reprogramming. FIG. 9B illustrates a CP graphical user interface screen representation schematic of workflow that includes the various setups and connections associated with each step.

III. Neurostimulation Lead Placement with EMG

Placement of the neurostimulation lead requires localization of the targeted nerve and subsequent positioning of the neurostimulation lead at the target location. Various ancillary components are used for localization of the target nerve and subsequent implantation of the lead and IPG. Such components include a foramen needle and a stylet, a directional guide, dilator and an introducer sheath, straight or curved tip stylet (inserted in tined leads), tunneling tools (a bendable tunneling rod with sharp tip on one end and a handle on the other with a transparent tubing over the tunneling rod) and often an over-the-shelf torque wrench. The foramen needle and stylet are used for locating the correct sacral foramen for implant lead and subsequent acute stimulation testing. The physician locates the targeted nerve by inserting a foramen needle and energizing a portion of needle until a neuromuscular response is observed that is indicative of neurostimulation in the target area (see Table 1 above). After the target nerve is successfully located, the direction guide, introducer and dilator are used to prepare a path along which the lead can be implanted. The directional guide is a metal rod that holds the position in the sacral foramen determined with the foramen needle for subsequent placement of the introducer sheath and dilator. The introducer sheath and dilator is a tool that increases the diameter of the hole through the foramen to allow introduction of the permanent lead. The lead stylet is a stiff wire that is inserted into the lead to increase its stiffness during lead placement and may be configured with a straight or curved tip. The torque wrench is a small wrench used to tighten the set screw that locks the lead into the IPG. The tunneling tool is a stiff, sharp device that creates a subcutaneous tunnel, allowing the lead to be placed along a path under the skin. While such approaches have sufficed for many conventional treatments, such approaches often lack resolution and may result in sub-optimal lead placement, which may unnecessarily complicate subsequent programming and result in unfavorable patient outcomes. Thus, an approach that provides more accurate and robust neural localization while improving ease of use by the physician and the patient.

A. EMG Assisted System Setup for Neural Localization and Lead Placement

In one aspect, the system utilizes EMG to improve the accuracy and resolution of neural localization with the foramen needle as well as to improve consistency and ease of performing each of neural localization and lead placement, as well as subsequent programming of the implanted neurostimulation system. In certain aspects of the invention, the system setups aim to use standard EMG recording techniques to create a unique approach to implanting a lead near the third sacral nerve and subsequent programming of electrical stimulation of the nerve. Such an approach is made feasible by integration of EMG recording, display and analysis with the CP, which is operatively coupled with the neurostimulation lead and used during lead placement and subsequent programming. Another advantageous aspect of this approach is that the use of proportional increases in stimulation amplitude during test stimulation and programming reduces the time required for these activities, as well as improve the ease with which the procedures can be conducted. In addition, recording of motor and sensory responses and stimulation amplitude thresholds directly into the CP during lead placement and conversion of these responses into feedback on the quality of lead placement and programming recommendations. Another advantageous aspect of this EMG assisted approach is that measurement and analysis of only one neuromuscular response, preferably the "big toe response," can be used as an indicator of appropriate stimulation amplitude for effective treatment during programming of the neurostimulation system. In another aspect, automation of these aspects within the CP can further reduce the duration and complexity of the procedure and improve consistency of outcomes. For example, automation of electrode threshold determinations based on EMG responses can provide rapid feedback during lead placement and to identify optimal programming parameters.

FIG. 9A illustrates a system setup for neural localization and lead placement using EMG response, as described above. As can be seen, several cable sets are connected to the CP 60. The stimulation cable set consists of one stimulation mini-clip 3 and one ground patch 5. It is used with a foramen needle 1 to locate the sacral nerve and verify the integrity of the nerve via test stimulation. Another stimulation cable set with four stimulation channels 2 is used to verify the lead position with a tined stimulation lead 20 during the staged trial. Both cable sets are sterilizable as they will be in the sterile field. A total of five over-the-shelf sensing electrode patches 4 (e.g., two sensing electrode pairs for each sensing spot and one common ground patch) are provided for EMG sensing at two different muscle groups (e.g., perineal musculature and big toe) simultaneously during the lead placement procedure. This provides the clinician with a convenient all-in-one setup via the EMG integrated CP. Typically, only one electrode set (e.g., two sensing electrodes and one ground patch) is needed for detecting an EMG signal on the big toe during an initial electrode configuration and/or re-programming session. Placement of the EMG patches on the patient for detection of an EMG waveform are shown in FIGS. 17A and 17B, which illustrate patch placement for detection of big toe response and anal bellow response, respectively.

Figure 9C:
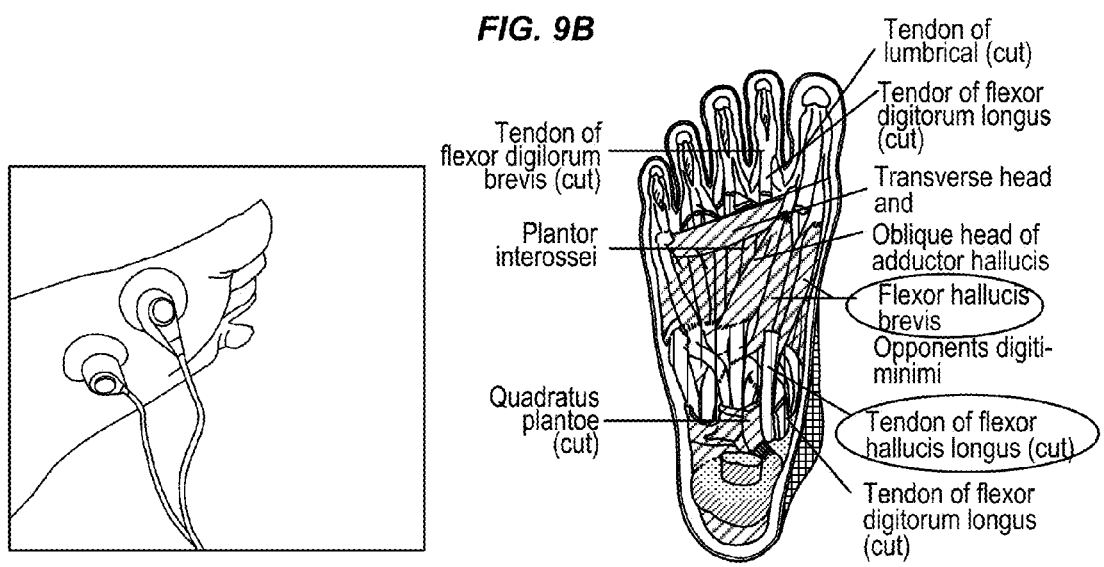
Figure 9D:
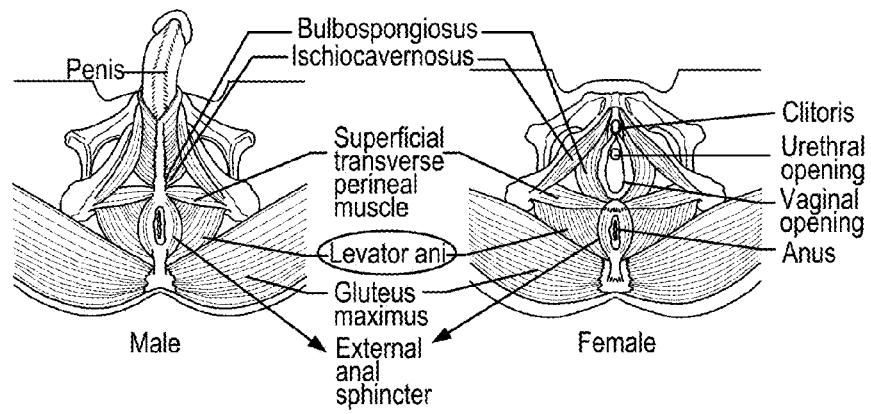

FIG. 9B illustrates example EMG patch/surface electrodes that can be adhered to the skin of the patient to obtain EMG recordings of a desired neuromuscular response. EMG recordings are obtained from a three-electrode configuration that includes a positive reference, a negative reference and a ground, typically each being provided on a surface path adhered to the skin of the patient. Alternatives to surface patches include needle electrodes and anal sponge electrodes. In one aspect, wireless EMG patches may be used to further improve the ease of use and patient comfort. In some embodiments, the EPG can be used as the stimulator within a fully wireless system setup. The EMG sensors are placed on the patient in a manner so as to record neuromuscular responses associated with a desired muscle movement. The key responses indicative of sacral nerve stimulation are the "big toe response" and the "anal bellows." The big toe response is the plantar flexion of the big toe. By placing the EMG sensor electrode patches on the flexor hallucis brevis (the primary target) or alternatively on the tendon of the flexor hallucis longus, such as shown in FIG. 9C, the system can record the EMG of the big toe response. The user may include a test stimulation of the medial plantar nerve to verify placement of big toe EMG electrodes and test nerve conduction. The "anal bellows" response is the tightening of the levators or pulling in of the pelvic floor. By placing the EMG sensor electrode patches on the levator ani muscle (both electrodes on one side) or alternatively on the levator ani muscles (one electrode on each side of the anus), see FIG. 9D, the system can record the EMG of the anal bellows response.

Figure 9E:
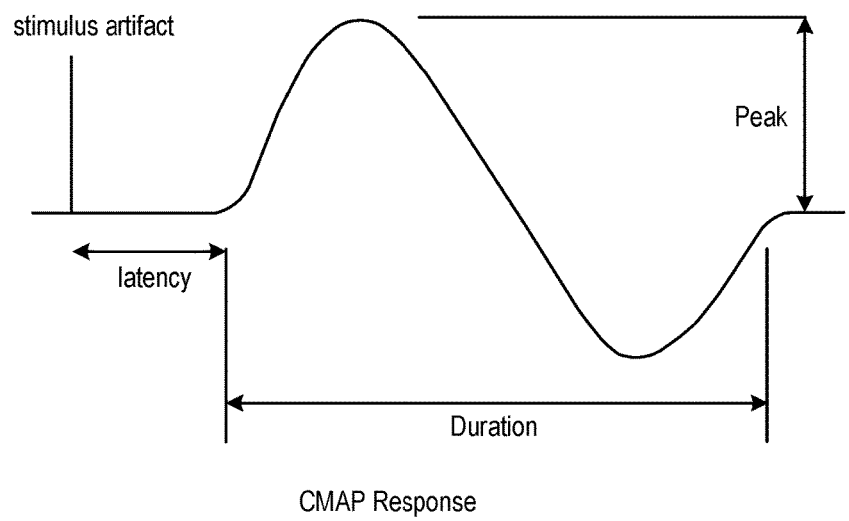
Figure 9F:
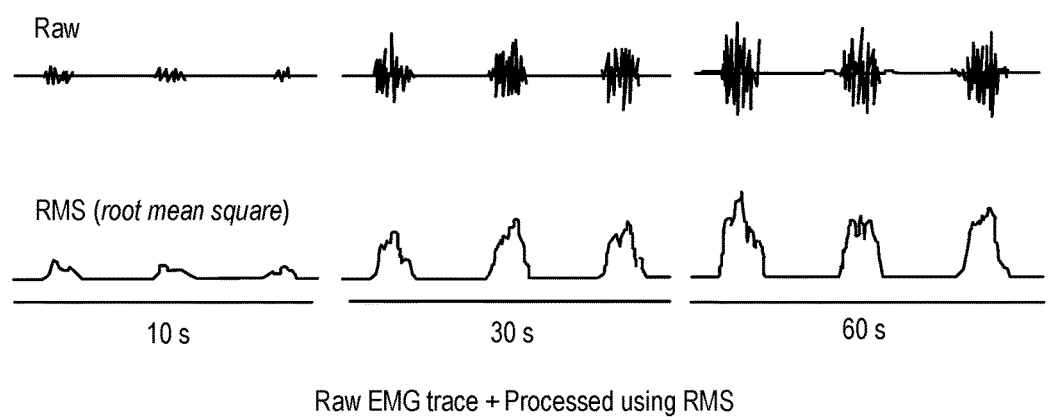

In one aspect, the EMG signal is used to evaluate placement quality and programming quality based on stimulation amplitude to evoke a response. The EMG responses are measured based on one of several approaches for quantifying the compound muscle action potential (CMAP). Referring to the EMG waveform shown in FIG. 9E, the "peak" is the maximum value of the positive peak of the CMAP, "peak-to-peak" is the value from the maximum peak to the minimum peak of the CMAP, the "root mean square (RMS) is defined as the time windowed average of the square root of the raw EMG squared. An example of raw data and the associated root mean square is shown in FIG. 9F. In some embodiments, the user will verify an EMG response by observation of the response. In other embodiments, stimulation automatically increases until an EMG response is observed.

B. Neural Localization with Foramen Needle

In conventional approaches, the foramen needle is positioned in an area adjacent the targeted nerve and energized until the desired muscle response is observed that is indicative of the targeted nerve being stimulated. A lead with multiple electrodes is inserted at approximately the same location as the foramen needle under the assumption that one or more of the electrodes will be in a position suitable for stimulating the targeted nerve. One of the drawbacks associated with this approach is that the position of the lead may differ slightly from the position of the foramen needle. In addition, since the foramen needle identifies a particular point location of the targeted nerve and the neurostimulation electrodes are disposed along a length of the lead, often the lead may be misaligned. For example, after successfully locating the target nerve with a foramen needle and inserting the neurostimulation lead, the lead may intersect the point located with the foramen needle but extend transverse or askew of the target nerve such that neurostimulation electrodes more distal and proximal of the intersecting point do not provide effective neurostimulation of the target nerve when energized, thereby limiting the neurostimulation programs available, which may lead to sub-optimal patient outcomes. Thus, while the foramen needle is effective in locating the target nerve at a particular point, often it does not provide enough resolution to ensure that the neurostimulation lead is properly positioned and aligned with the target nerve along the entire length on which the neurostimulation electrodes are disposed.

In accordance with aspects of the present invention, the recorded EMG is used to facilitate neural localization with a foramen needle. Typically, a foramen needle includes a discrete electrode that is stimulated until a desired neuromuscular response is observed. In one aspect, the stimulation level is increased until a desired EMG response (e.g. anal bellows and/or big toe) is recorded, at which point the associated amplitude is recorded as well, typically at a constant current. The user may increase the stimulation level in desired increments or the system may automatically increase the stimulation until the EMG response is recorded.

Figure 9G:
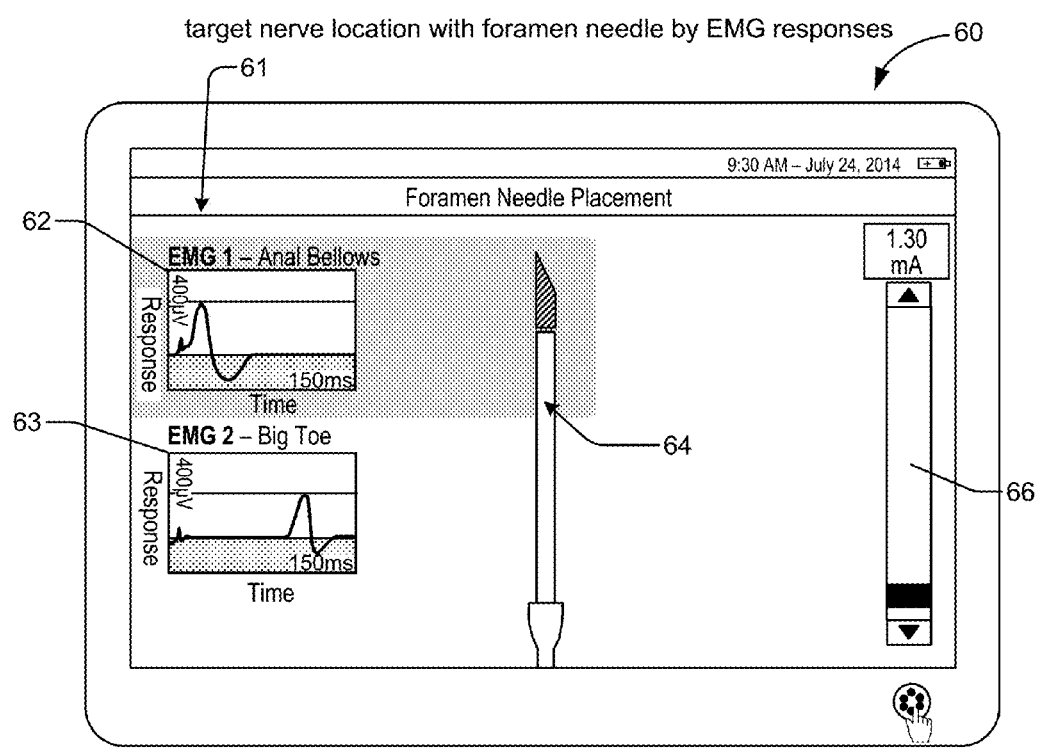

As shown in FIG. 9G, the graphical user interface display of the CP 60 allows the user to monitor the EMG responses and associated amplitudes. The CP 60 interface includes EMG waveform displays 61 are used to monitor a desired neuromuscular response, an Amplitude display 66 and an Electrode Status Indicator 64, which may include a representation of the foramen needle during neural localization. The waveform displays 61 include an Anal Bellow EMG display 62 and a Big Toe EMG displays 63. The amplitude in conjunction with the recorded EMG response can be used to identify when the electrode of the foramen needle is at the targeted nerve. An amplitude greater than a desired range may indicate that the location of the electrode is marginal or unsuitable for use as a cathode in delivering a neurostimulation treatment.

In some embodiments, the display provides feedback to the user (e.g. color coding) as to whether the foramen needle is at the targeted nerve based on the EMG and amplitude measurements. For example, the tip of the foramen representation may be green to indicate a "good" position: (<2 mA); yellow may indicate an "ok" position (2-4 mA) and red may indicate a "bad" position (>4 mA). In some embodiments, the system is configured such that amplitude adjustment is performed in auto-adjusting increments. In one example, from 0-1 mA, step-size is 0.05 mA; from 1-2 mA, step-size is 0.1 mA; from 2 mA-3 mA, step-size is 0.2 mA; and from 2 mA+, step-size is 0.25 mA. In some embodiments, the system may include an option to turn off auto-adjusting increments and use fixed increments, such as fixed increments of 0.05 or 0.1 mA.

C. Lead Placement with EMG

Figure 10:
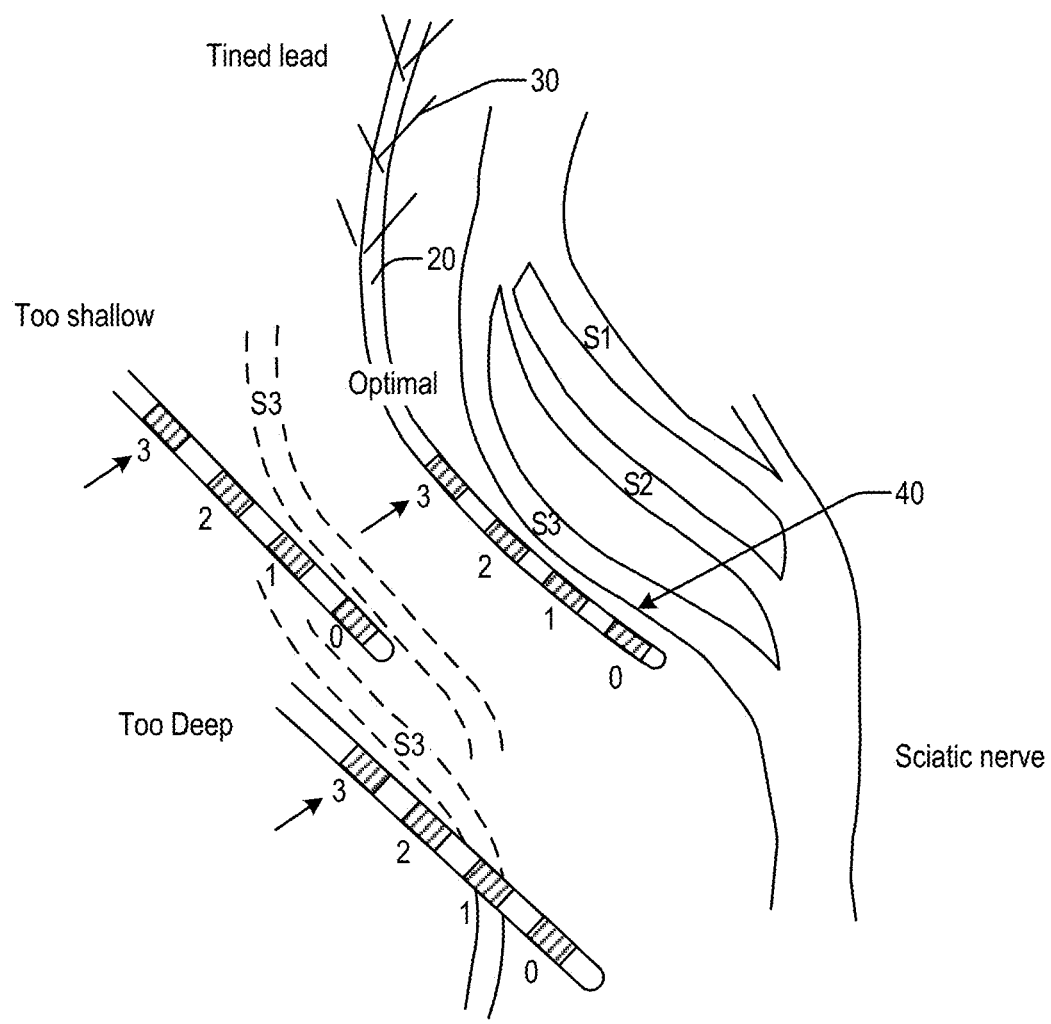
FIG. 10 illustrate differing positions of the neurostimulation lead relative the targeted nerve during placement of the lead and FIGS. 11A-11L illustrate curves of R-values of the electrodes used to determine distance of the electrodes from the target nerve to facilitate placement of the lead, in accordance with aspects of the invention.

After neural localization is complete, the neurostimulation lead is advanced to the target location identified during neural localization. Typically, a neurostimulation lead include multiple electrodes along a distal portion of the lead, as can be seen in FIG. 4, such that there are various differing positions along which the lead can be placed at or near the target location. For example, as shown in FIGS. 10 and 12A-12B, the lead can be advanced "too deep" beyond the targeted nerve, can be placed "too shallow" or can be tilted or angled such that the distal or proximal electrodes are spaced too far away from the target nerve. The neurostimulation lead can be re-positioned along various differing paths within the three-dimensional space of the implantation site to an optimal location and alignment by advancing or retracting the lead along the insertion axis and/or steering the lead in a lateral direction from the insertion axis as needed. While it is desirable for all four electrodes to be in an optimal location, three out of four electrodes being in acceptable proximity to the target nerve to deliver neurostimulation therapy is generally acceptable. Determining an actual location of the lead, however, can be difficult and time-consuming using conventional methods of manually adjusting the stimulation on each electrode separately and relying on observation of the muscle responses after each stimulation. Fluoroscopy is an often used tool to verify lead position against anatomical landmarks, however, this approach is not very effective since nerves are not visible under fluoroscopy.

In one aspect, the system provides improved lead placement by determining lead position of a multi-electrode lead relative the target nerve with EMG using an electrode sweeping process. This approach allows for fine tuning of lead placement. This feature utilizes a four-channel connecting cable so as to allow the system to energize each electrode in rapid succession without requiring separate attachment and detachment on each electrode with a J-clip or alligator slip, such as is used in convention methods. This aspect is advantageous since utilization of a J-clip or alligator clip to make contacts to tightly pitched electrode is difficult and time consuming and could potentially result in movement of the lead during testing.

In the sweeping process, the system identifies a principal electrode. This may be a default selection by the system or selected by the physician using the CP. The stimulation of the principal electrode is adjusted until an adequate motor response with a maximum amplitude CMAP is obtained at which point the stimulation level or amplitude is recorded. The system then sweeps through all the remaining electrodes of the lead with the same stimulation level and records the EMG responses from each electrode. Typically, the sweeping process is performed rapidly. For example each contact can be stimulated individually at the same stimulation level for 1 second such that the entire sweeping cycle can be conducted in about 4-5 seconds for a four-electrode lead. The system can determine responses for each electrode that can be used to indicate the relative distances of each electrode from the target nerve, which may also be recorded for subsequent use in programming of the EPG or IPG. There are several options as to how this sweeping process can be used to facilitate fine tuning of lead placement, including the following two options.

Option 1: In one approach, the EMG response value for each electrode can be indicated on a graphical user interface display of the clinician programmer. For example, the response value can be indicated by color coding the electrodes on the display (see FIG. 14D) or by bars or boxes displayed next to each electrode on the Electrode Status Indicator 64 (see FIG. 15A). These indicators readily communicate the robustness of the EMG response achieved at each electrode to the clinician. In one aspect, each electrode may be assigned an R-value, where the R-value is a unit-less number, derived from each electrode's EMG peak CMAP amplitude recorded during the sweeping process, and normalized relative to that of the principal electrode selected by the clinician. In some embodiments, an R-value>0.5 is deemed a "good" location (e.g. color coded green; R-value of 1 or higher is preferable); an electrode with an R-value that is $0.25<r<0.5$ is deemed "not ideal" (e.g. color coded yellow); and an electrode with an R-value that is $r<0.25$ is deemed not acceptable (e.g. color coded red).

Option 2: In another approach, the response value is illustrated in terms of the distance to the target nerve determined based onx the relative response value of each electrode. In one aspect, the R-values may be converted to relative distance which allows for ready interpretation of a relative position of the electrode to the target nerve. Examples of these R-value and distance curves in regard to differing positions of the leads are described in FIGS. 10-13F as follows.

FIG. 10 illustrates initial placement of the neurostimulation lead 20 along the path, the lead 20 including four neurostimulation electrodes 40, electrode #0-3, from electrode #0, the distal most electrode to electrode #3, the proximal most electrode. In one aspect, the "optimal lead position" for neurostimulation treatment is one in which each of the neurostimulation electrodes 40 are adjacent the targeted nerve (e.g. S3 sacral nerve) along the electrode portion 40. If the lead is not advance far enough, the lead position is "too shallow" such that only the more proximal electrodes (e.g. 0, 1) are adjacent the targeted nerve. If the lead is advanced too far, the lead position is "too deep" such that only the more proximal electrodes (e.g. 2, 3) are adjacent the targeted nerve and the more distal electrodes have been advanced beyond the target location.

The axial position of the lead relative the target nerve can be reflected using the R-values for each electrode obtained during sweeping. If the lead is too shallow, the R-value curves obtained may resemble FIG. 11A if the R-values were keyed off of electrode #3, the most proximal electrode. This curve is converted to the distance curve shown in FIG. 11B, which indicates that electrodes #3 and #2 are unacceptably far from the target nerve. In response to this curve, in some cases, combined with fluoroscopy images (showing the relative position of lead and anatomic landmarks), the physician may determine and/or the system may suggest to the physician, such as by indicator on the CP, to insert the lead deeper. The sweeping process can be repeated and new R-value and distance curves obtained until distance curves indicate a more optimal position of the lead, such as that shown in FIG. 11C for example. If the lead is positioned "too deep", the R-value curves obtained may resemble that in FIG. 11D if the R-values were keyed off of electrode #3. The R-value curve converts to the distance curve shown in FIG. 11E, which indicates that electrodes #0 and #1 are unacceptably far from the target nerve. In response to this curve, in some cases, combined with fluoroscopy images (showing the relative position of lead and anatomic landmarks), the physician may determine and/or the system may suggest to the physician, such as by indicator on the CP, to pull the lead back. The sweeping process can then be repeated and new R-value and distance curves obtained until distance curves indicate a more optimal position of the lead, such as that shown in FIG. 11F for example.

Figure 11A:
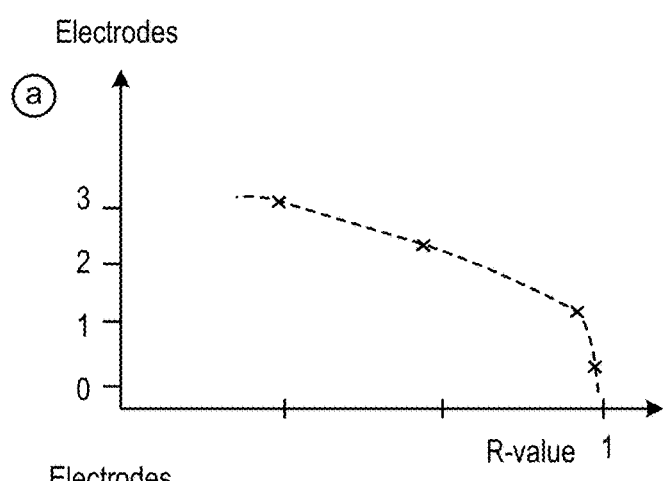
Figure 11B:
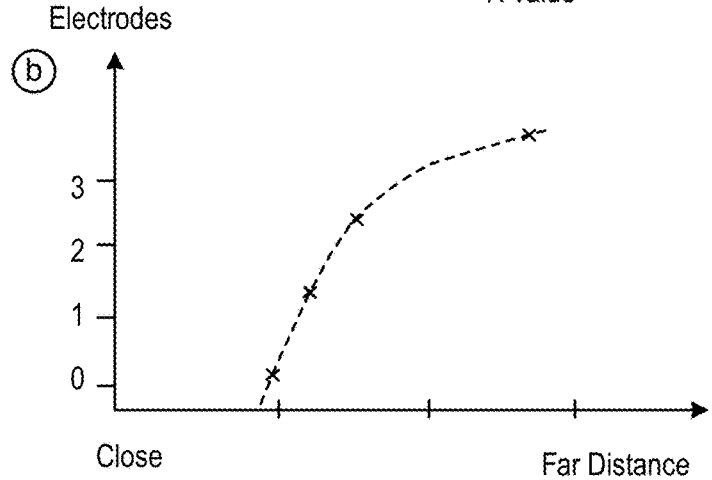
Figure 11C:
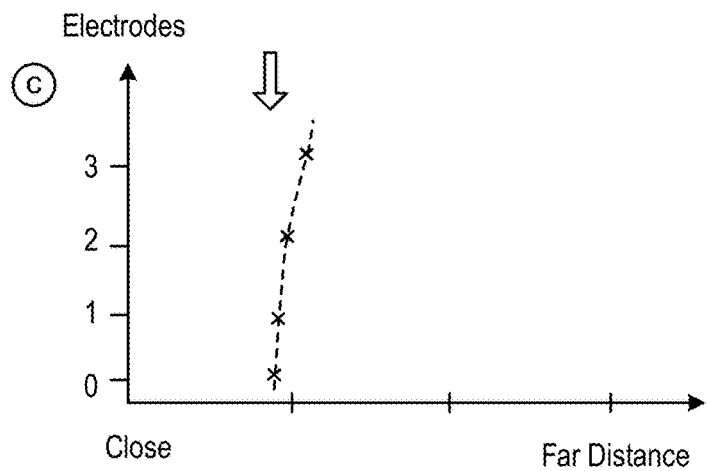
Figure 11D:
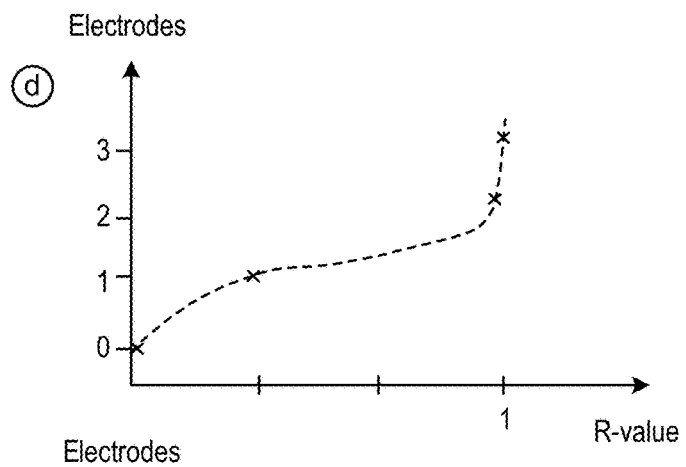
Figure 11E:
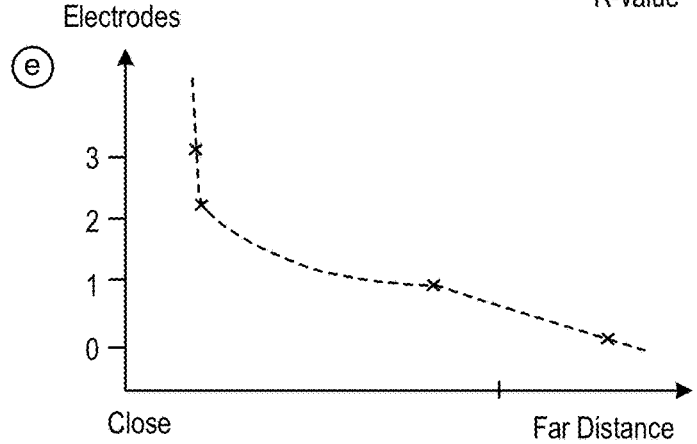
Figure 11F:
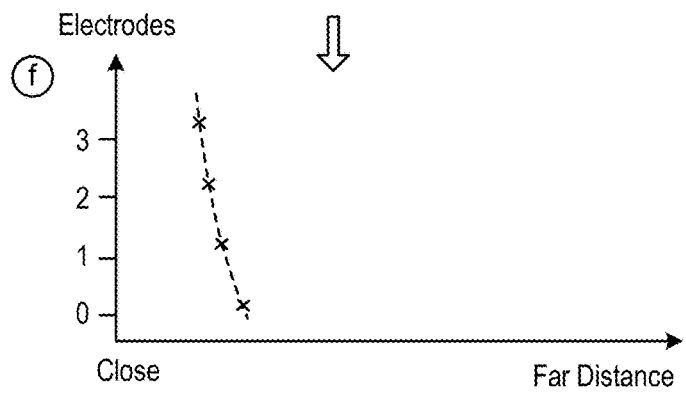
Figure 11G:
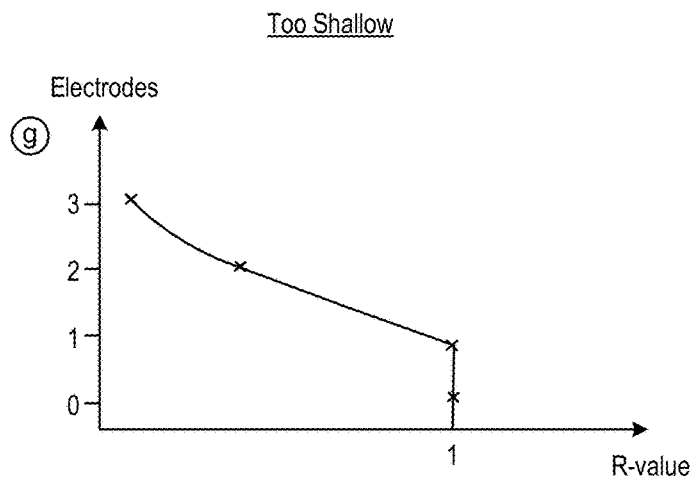
Figure 11H:
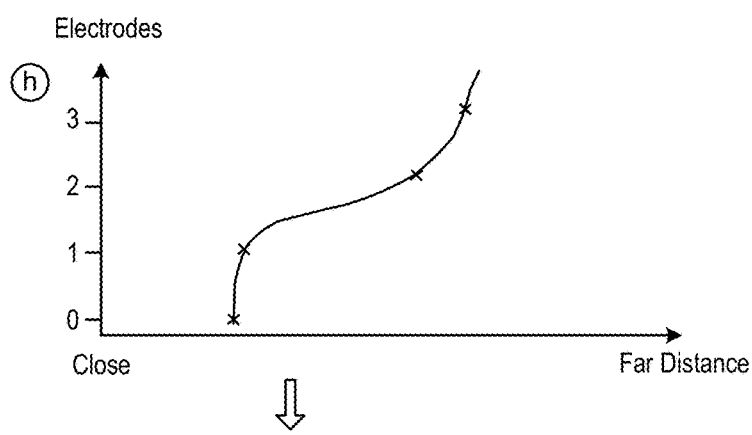
Figure 11I:
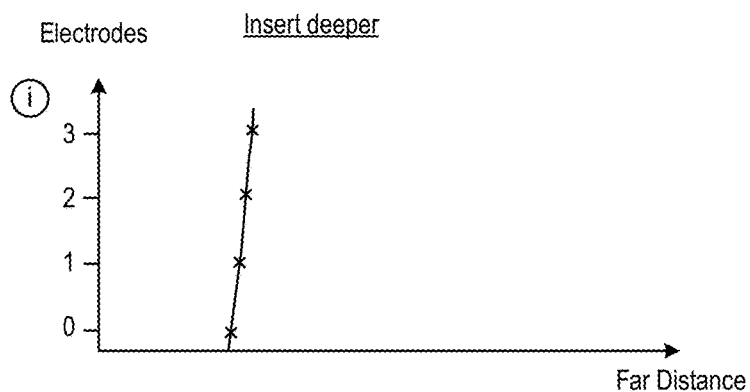
Figure 11J:
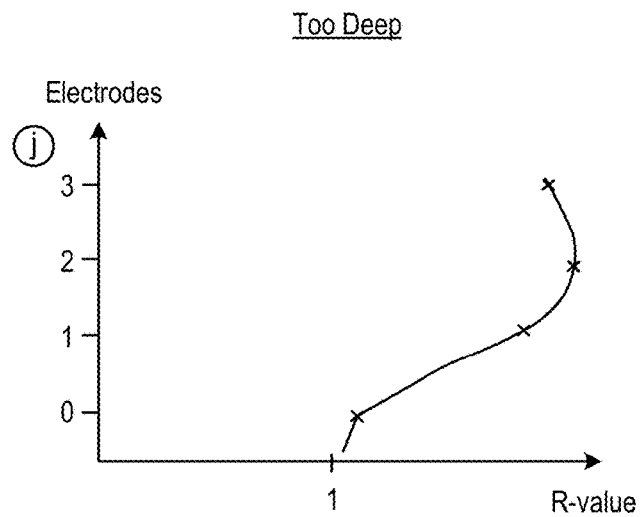
Figure 11K:
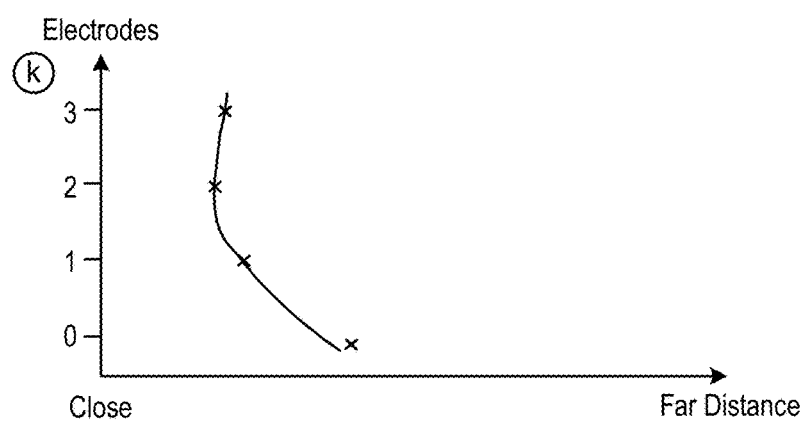
Figure 11L:
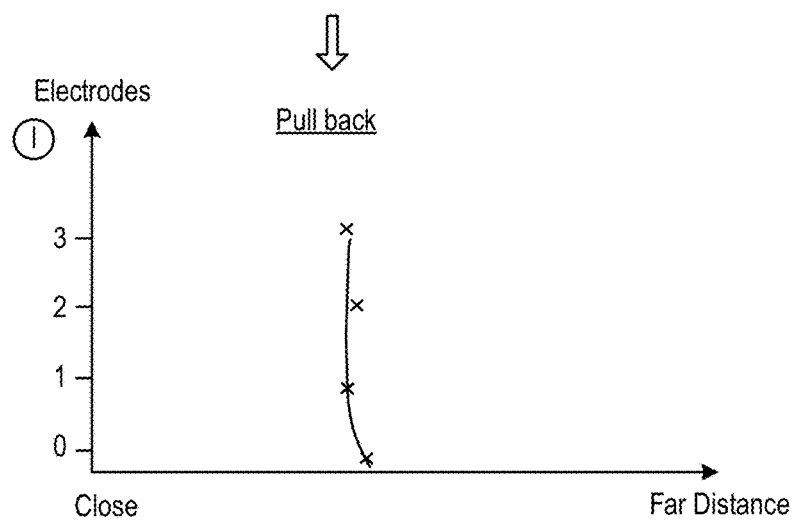
Figure 13A:
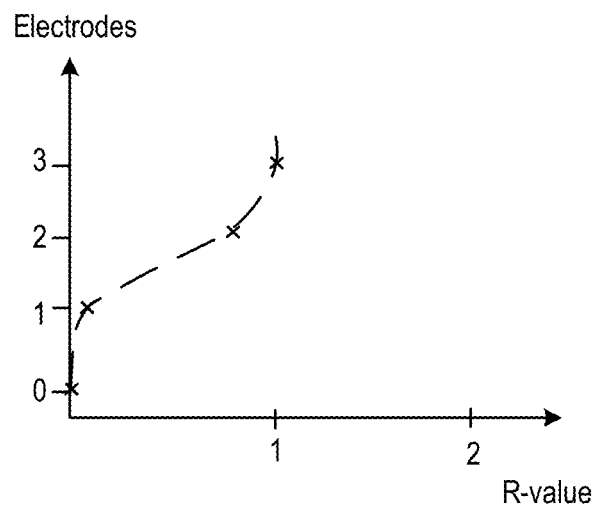
Figure 13B:
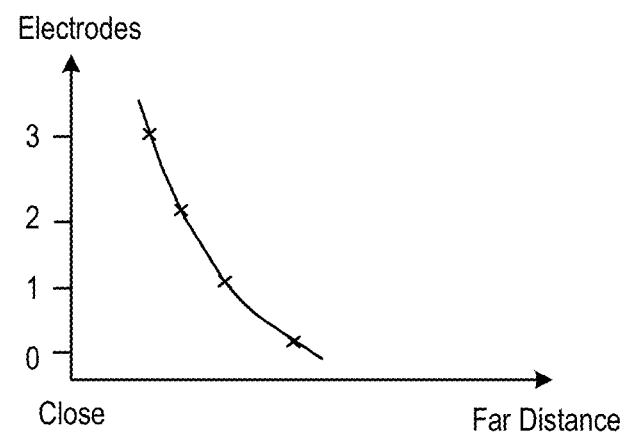
Figure 13C:
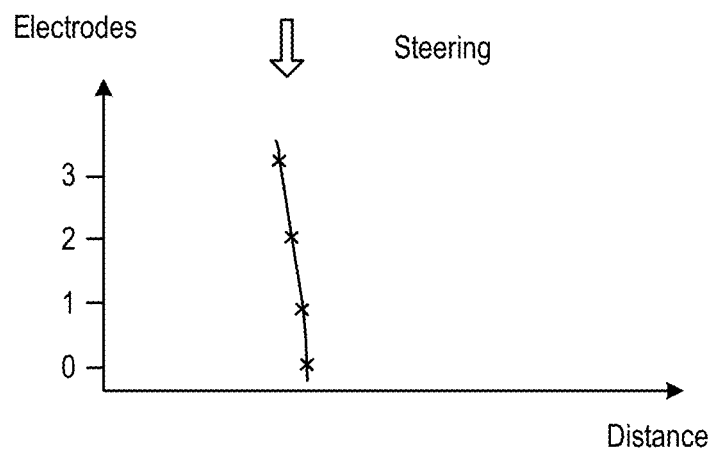
Figure 13D:
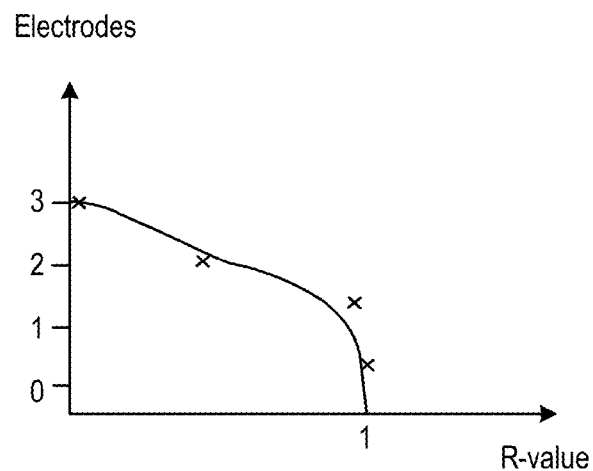
Figure 13E:
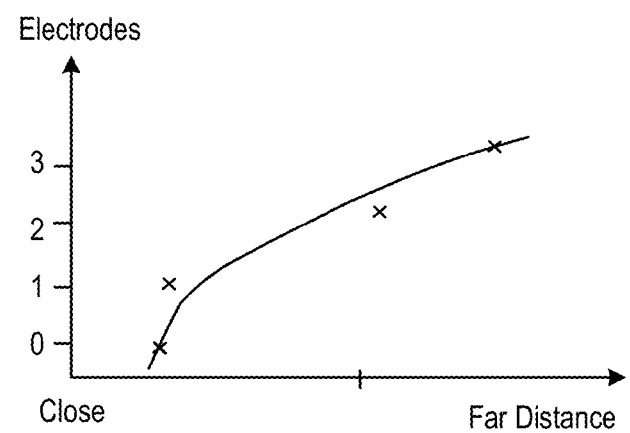
Figure 13F:
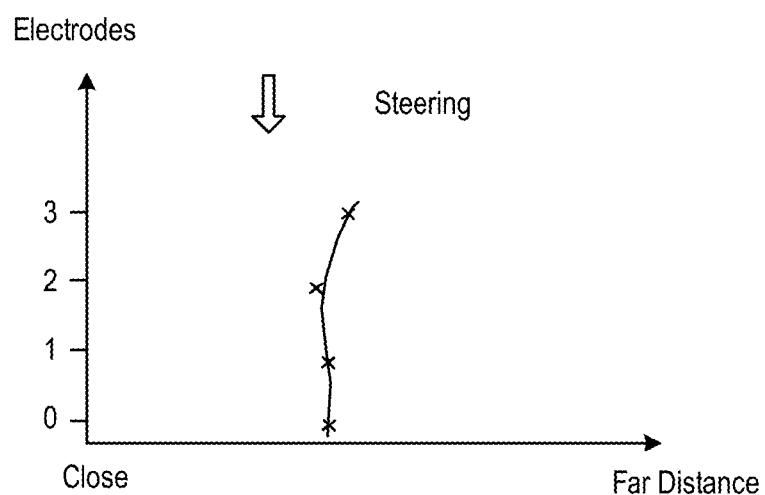

If the lead is too shallow, the R-value curves obtained may resemble FIG. 11G if the R-values were keyed off of electrode #0, the most distal electrode. This curve is converted to the distance curve shown in FIG. 11H, which indicates that electrodes #3 and #2 are unacceptably far from the target nerve. In response to this curve, in some cases, combined with fluoroscopy images (showing the relative position of lead and anatomic landmarks), the physician may determine and/or the system may suggest to the physician, such as by indicator on the CP, to insert the lead deeper. The sweeping process can be repeated and new R-value and distance curves obtained until distance curves indicate a more optimal position of the lead, such as that shown in FIG. 11I for example. If the lead is positioned "too deep", the R-value curves obtained may resemble that in FIG. 11J if the R-values were keyed off of electrode #0. The R-value curve converts to the distance curve shown in FIG. 11K, which indicates that electrodes #2 and #3 are unacceptably close from the target nerve. In response to this curve, in some cases, combined with fluoroscopy images (showing the relative position of lead and anatomic landmarks), the physician may determine and/or the system may suggest to the physician, such as by indicator on the CP, to pull the lead back. The sweeping process can then be repeated and new R-value and distance curves obtained until distance curves indicate a more optimal position of the lead, such as that shown in FIG. 11L for example. Generally, the shape of the curves FIGS. 11A-L provide a visual representation that aid in optimal lead placement. Optimal lead placement comprises R-vales in a similar range and/or robust EMG responses at reasonable stimulation amplitudes. For example, similar R-values but low EMG responses at high stimulation amplitudes alert the clinician that the lead needs to be re-positioned closer to the target nerve region. The combination of R-values, trial and error, and fluoroscopic imaging aid in optimal lead positioning, such as axial and/or lateral adjustments of the lead.

In another aspect, the lateral displacement of the lead relative the target nerve due to tilting or angling can be reflected using the R-values obtained during the sweeping process. For example, FIG. 12A illustrates a lead 20 in a position in which the distal end is skewed away from the targeted nerve, the S3 sacral nerve, and FIG. 12B illustrates a lead 20 in which the distal electrode portion is "tilted in" toward the target nerve. In the scenario shown in FIG. 12A, if the electrode measurements are keyed off electrode #3, the most proximal electrode, the R-value curves obtained may resemble that shown in FIG. 13A. This R-value curve converts to the distance curve shown in FIG. 13B, which indicates that electrode #0 is laterally displaced too far from the target nerve. In response to this curve, in combination with fluoroscopy information, the physician may determine and/or the system can provide an indicator of a suggestion to steer the distal portion of the lead nearer to the targeted nerve. The sweeping process is repeated and new R-values and distance curves obtained and the process is repeated until the curves resemble those shown in FIG. 13C, which is more indicative of an optimum alignment in which each of the electrodes 0-4 is suitably near the target nerve. In the scenario shown in FIG. 12B, if the electrode measurements are keyed off electrode #0, the most distal electrode, the R-value curve obtained may resemble that shown in FIG. 13D. This curve converts to the distance curve shown in FIG. 13E, which indicates that electrode #3 is laterally displace too far from the target nerve. In response to this curve in combination with fluoroscopy information, the physician may determine and/or the system can provide an indicator of a suggestion to steer the distal portion of the lead nearer to the targeted nerve. The sweeping process is repeated and new R-values and distance curves obtained until the curves resemble those shown in FIG. 13F, which is more indicative of an optimum alignment in which each of the electrodes 0-4 is suitably near the target nerve.

In some embodiments, the R-value and/or distance curves may be determined by the system and used to communicate a suggestion to the clinician, such as with the CP, as to whether the lead should be advanced, retracted or steered. In other embodiments, the R-values and/or the associated curves may be displayed on a graphical user interface of the CP so as to provide a visual indicator of the robustness of each electrode and/or its relative location. In one aspect, a suitable lead position is one in which at least three of the four electrodes are disposed adjacent to and along the targeted nerve. Due to the unique shapes of nerve structures, an optimal lead position in which all electrodes are adjacent the target nerve may not always be readily achievable.

Figure 14A:
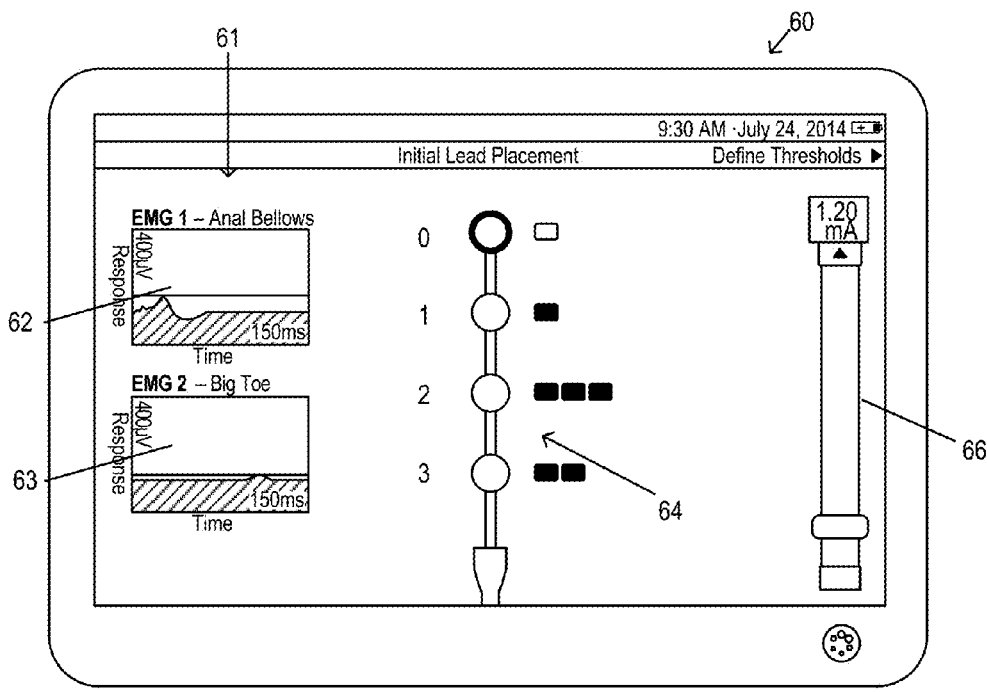
FIGS. 14A-14B illustrate a graphical user interface display of a clinician programmer during electromyography assisted lead placement, in accordance with aspects of the invention.
Figure 14B:
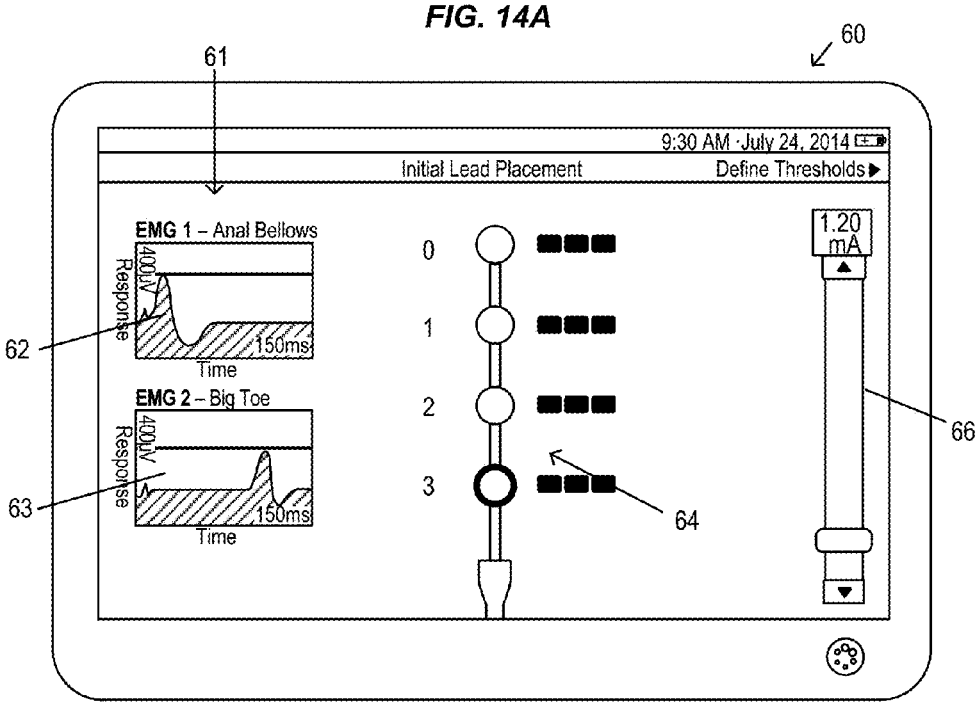

FIGS. 14A-14B illustrate a graphical user interface of the CP 60 during initial lead placement procedure, in accordance with aspects of the invention. The CP 60 interface can includes EMG waveform displays 61 used to monitor a desired neuromuscular response, an Amplitude display 66 and an Electrode Status Indicator 64, which during lead placement includes a representation of the electrode portion of the lead 20. In this procedure, the EMG signal is used to evaluate placement quality based on stimulation amplitude to evoke a response. In some embodiments, the user selects the amplitude and presses "stimulate," after which each electrode is stimulated for one second. The user determines if the response amplitudes are acceptable. In other embodiments, the system automatically increases until a self-determined level is reached or until a pre-determined EMG response is recorded. In some embodiments, amplitude adjustment can be done in auto-adjusting increments, as described previously. The system may provide a suggestion as to a direction to move the lead if the responses are unacceptable. As shown in FIG. 14A, the responsiveness of each electrode may be graphically represented, for example by bars or boxes to the right of each electrode in the graphical representation of the lead in the Electrode Status Indicator 64. In this example, boxes to right of each contact represent the EMG value (e.g., peak value) for that contact as follows: open square (<50 uV), 1 closed square (50-100 uV), 2 closed squares (100-150 uV), and 3 closed squares (150+uV). A visual indicator that the more distal electrodes (electrode #0, 1) have sub-optimal EMG peak values, such as shown in FIG. 14A, may communicate to the clinician that the lead needs to be pulled back proximally until at least three of the four electrodes, preferably all electrodes, have acceptable EMG peak values (e.g. 3 closed square at 150+ uV).

Figure 15A:
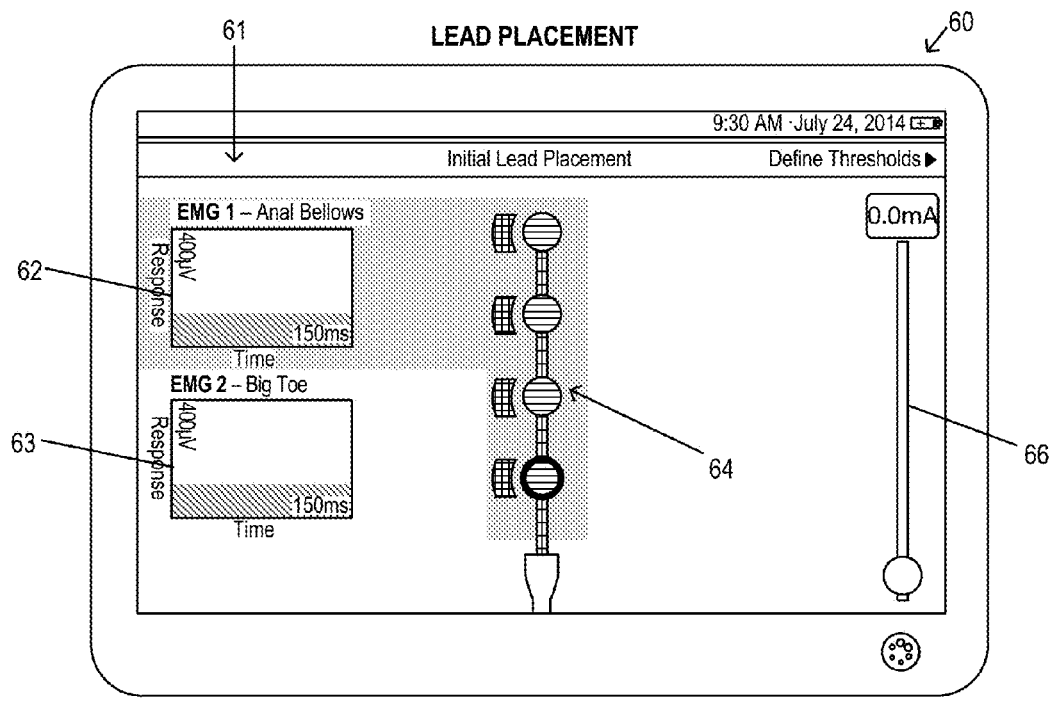
FIG. 15A-15L illustrate a graphical user interface display of a clinician programmer during an alternative electromyography assisted neurostimulation lead placement procedure, in accordance with aspects of the invention. in accordance with aspects of the invention.
Figure 15B:
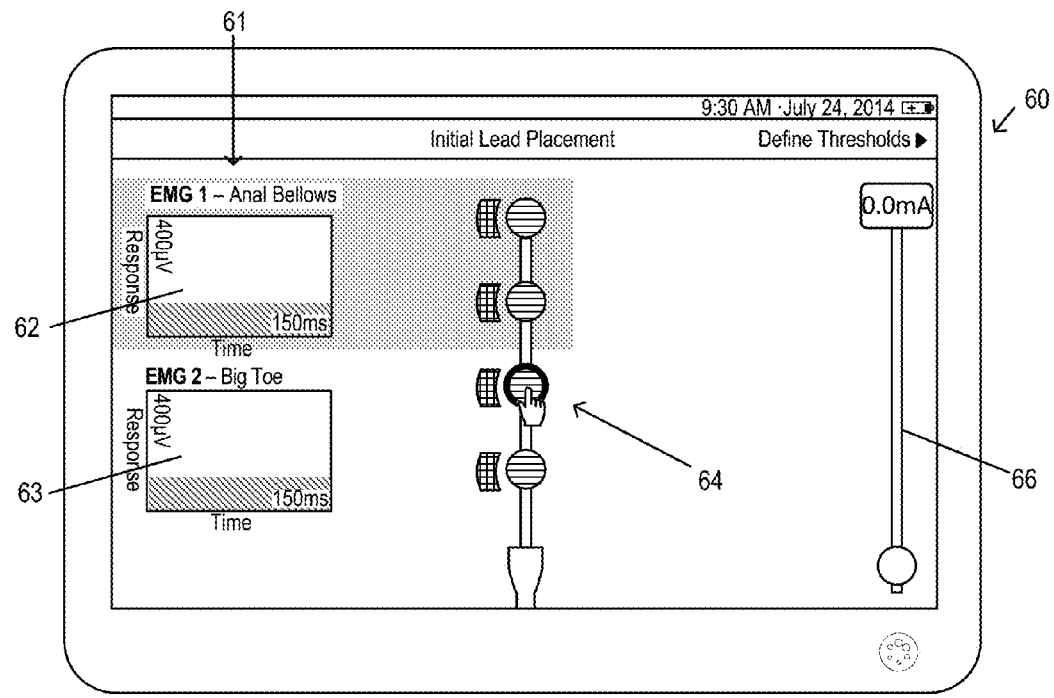

FIGS. 15A-15M illustrate the graphical user interface display of the clinician program during another lead placement procedure, in accordance with the invention. The four channel lead and stimulation cables are attached to a CP with a graphical user interface to facilitate lead positioning, electrode characterization and neurostimulation programming. As shown in FIG. 15A, the graphical user interface of the CP 60 includes EMG waveform displays 61, electrode status display 64 and electrode threshold display 66. The EMG waveform display 61 includes two waveform displays, an Anal Bellows EMG display 62, which is coupled with EMG 1 patch, and a Big Toe EMG display 63 coupled with EMG 2 patches adhered on the patient's foot. The electrode status display 64 can be configured to display which electrode is being energized along with a status of the electrode (e.g. suitability for neurostimulation, amplitude threshold within pre-determined limits), and can further allow selection of an electrode by use of an onscreen selector or cursor, as shown in FIG. 15B. The threshold display 66 displays the amplitudes of the selected electrode.

Figure 15C:
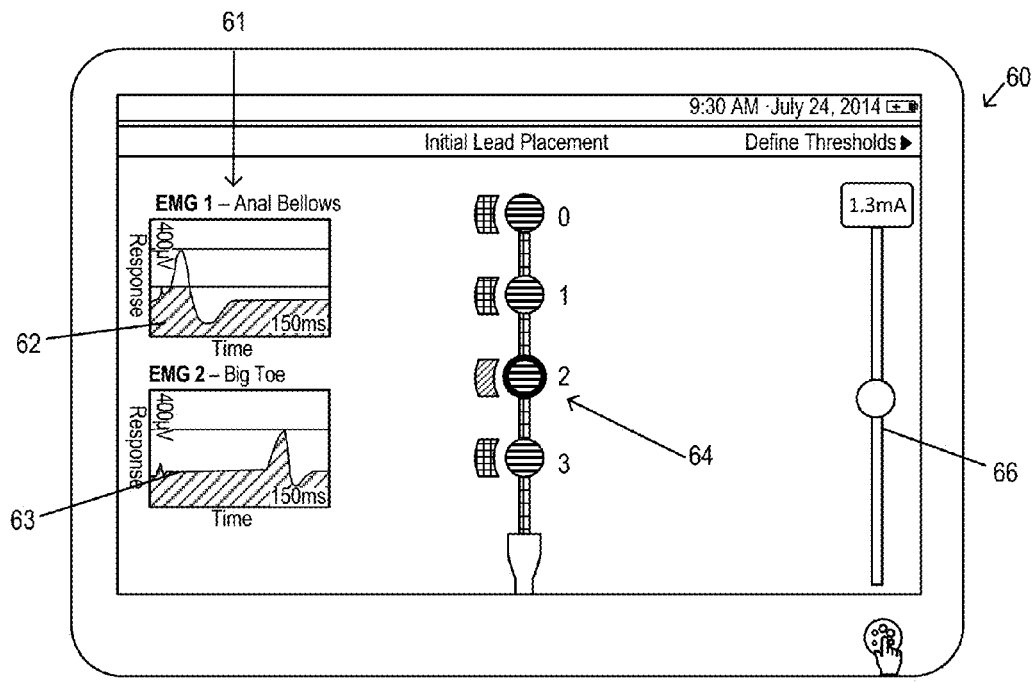
Figure 15D:
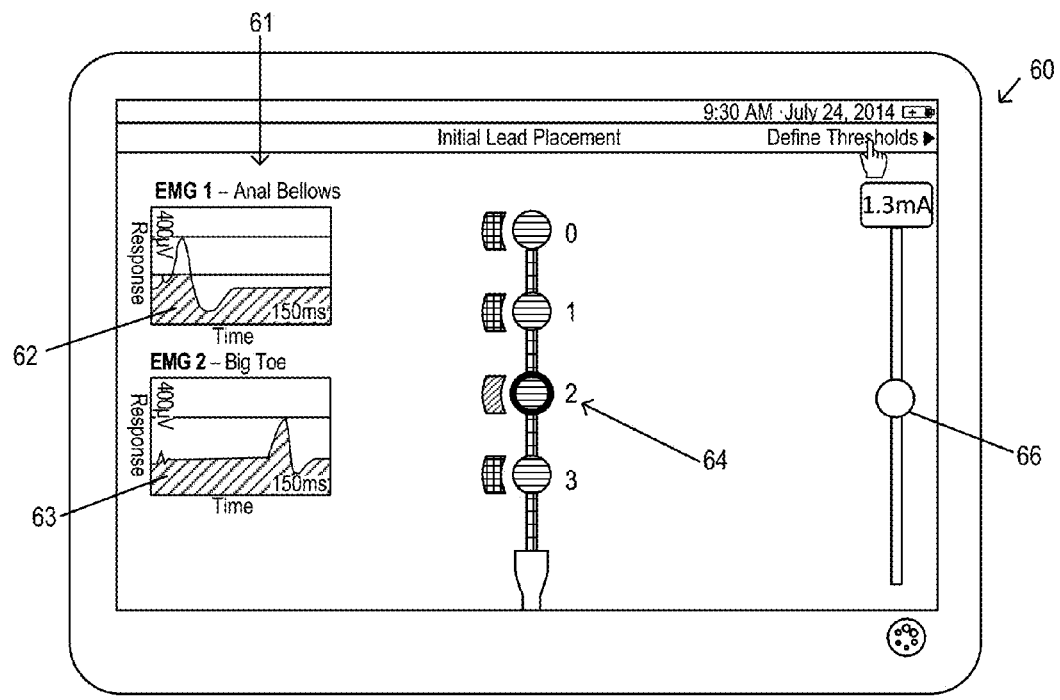

After selection of a principal electrode, the CP performs a test stimulation on the 4-channel lead, which is typically a quick check across all electrodes of the lead (e.g., sweep). In one aspect, the CP records the EMG waveform displays 62 and 63 and the amplitude threshold reading for each selected electrode during this test stimulation. From this test stimulation, the CP 60 may display the suitability of each electrode for neurostimulation in the electrode status display 64 by a color coding or other suitable indicator. For example, in the electrode status display 64 in FIG. 15C, the electrode icons to the left of each electrode can be color coded in differing colors, for example electrodes 0, 1 can be coded as "green," electrode 2 coded as "orange," and electrode 3 coded as "red" based on based on its threshold and EMG response, green indicating that the electrode is suitable for use in neurostimulation, orange indicating that the electrode is marginal for use in neurostimulation and red indicating that the electrode is not suitable for use as a cathode in neurostimulation. The electrode may be marginal or unsuitable for use as a cathode based on either or both of the amplitude threshold being too high or based on lack of response in the EMG. FIG. 15C may communicate to the clinician that the lead needs to be advanced distally until at least three of the four electrodes have green indications to denote optimal positioning. After initial lead placement, the amplitude thresholds for each electrode may be determined upon selection of "Define Thresholds" by the user, as shown in FIG. 15D.

D. Electrode Threshold Determination/Validation of Lead Placement

Figure 15E:
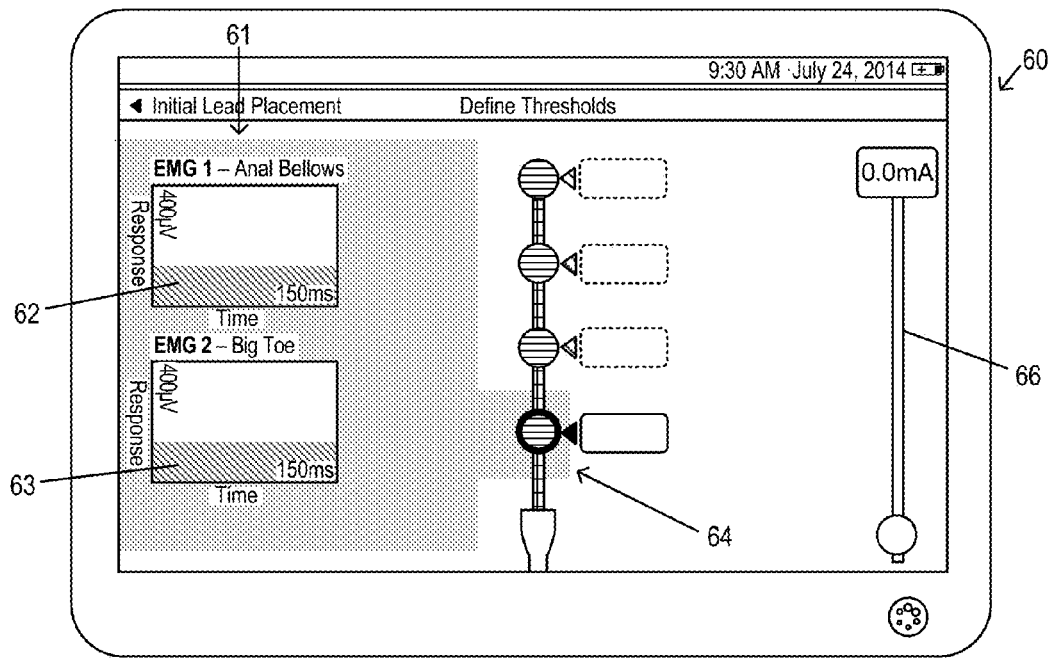
Figure 15F:
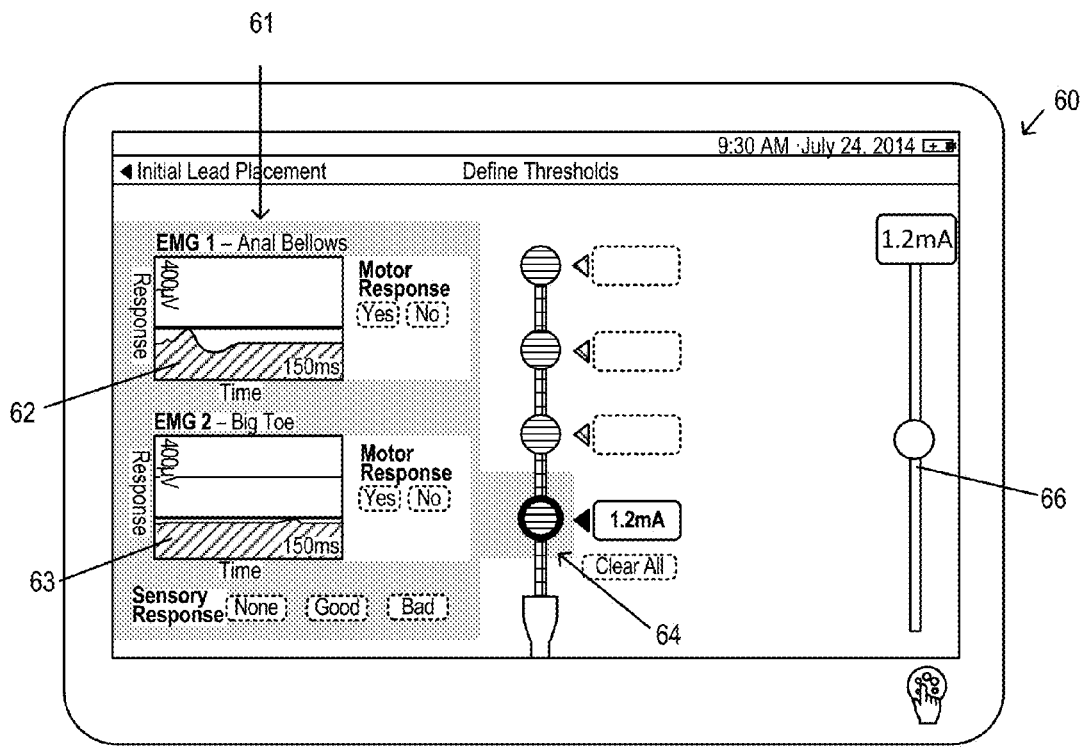
Figure 15G:
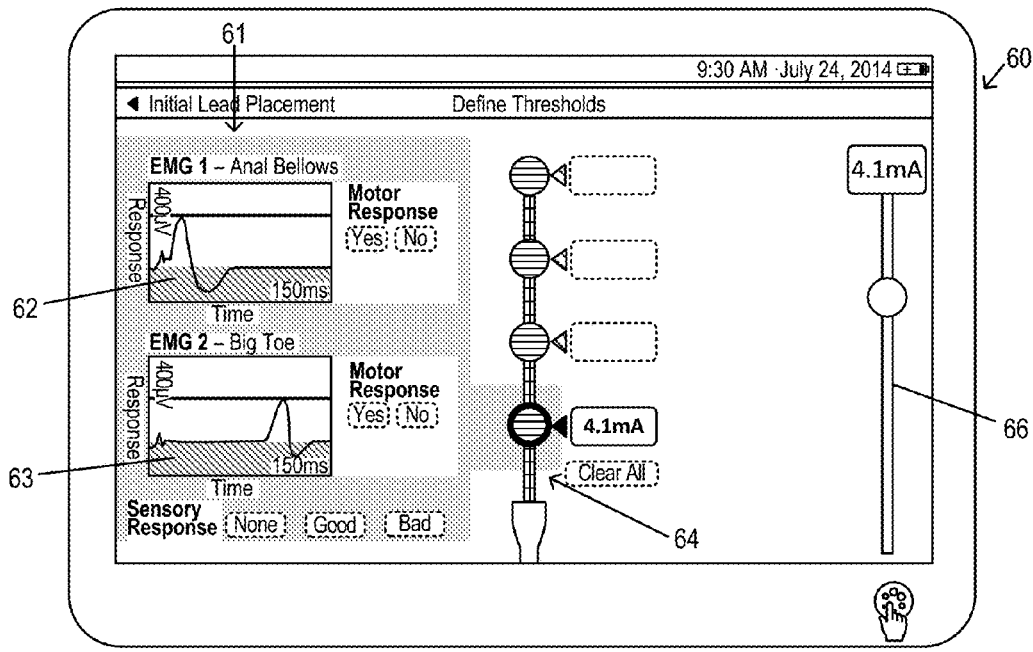
Figure 15H:
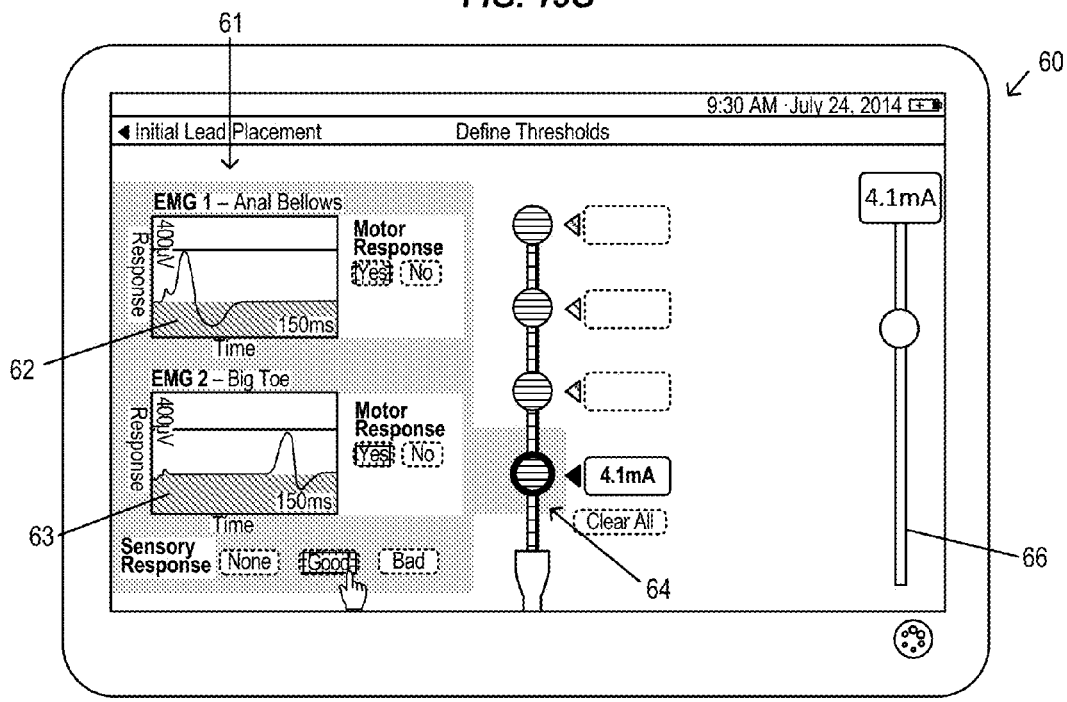
Figure 15I:
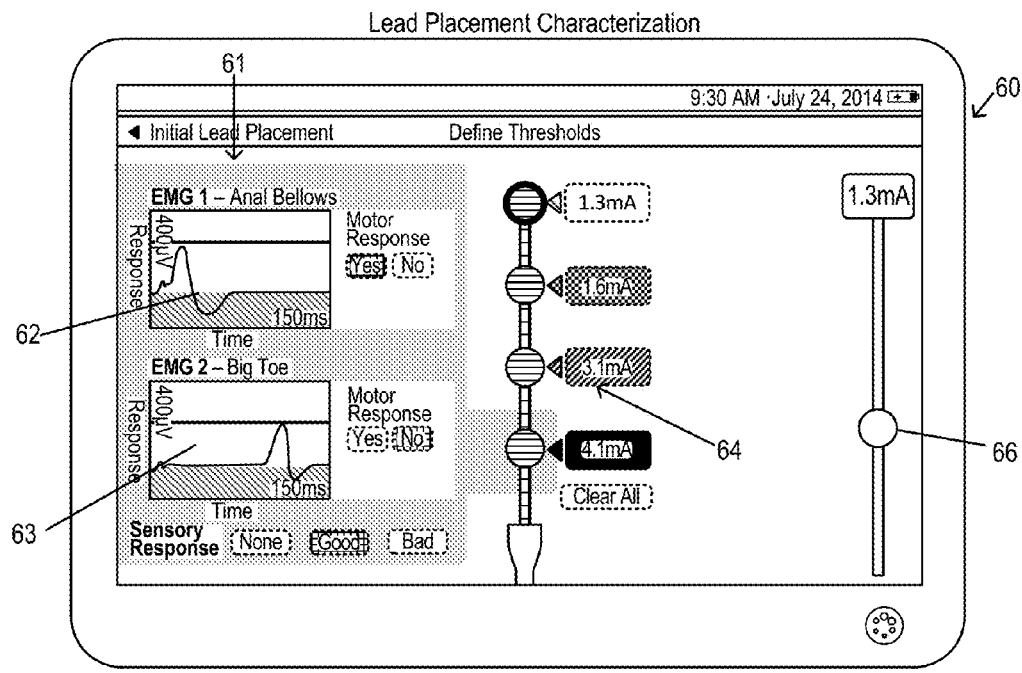

As shown in FIG. 15E, the CP can validate lead placement by testing for stimulation thresholds for each electrode of the four channel lead. The CP increases the stimulation level of the selected electrode and records the magnitude of the EMG response, which appears in the EMG waveform displays 61 on the graphical user interface of the CP 60 (see line on each waveform in FIG. 15F). The stimulation is increased until a pre-determined or desired EMG response threshold is reached, at which point the amplitude is recorded and displayed on the electrode status display 64 next to the subject electrode, as shown in FIG. 15F. Optionally, the response for each electrode is characterized at this time and recorded for use in subsequent programming. The above process is repeated for each electrode. If the threshold amplitude is outside a suitable range of amplitude thresholds, the amplitude may be designated as marginal or unsuitable for use as a cathode in neurostimulation. Designations may be made by visual indicators, such as color coding (e.g. green, orange, red) to indicate suitability of the selected electrode for use as a cathode in a neurostimulation treatment, as shown in FIG. 15I, which shows electrodes #0 and #1 as green, electrode #2 as orange and electrode #3 as red.

Figure 15J:
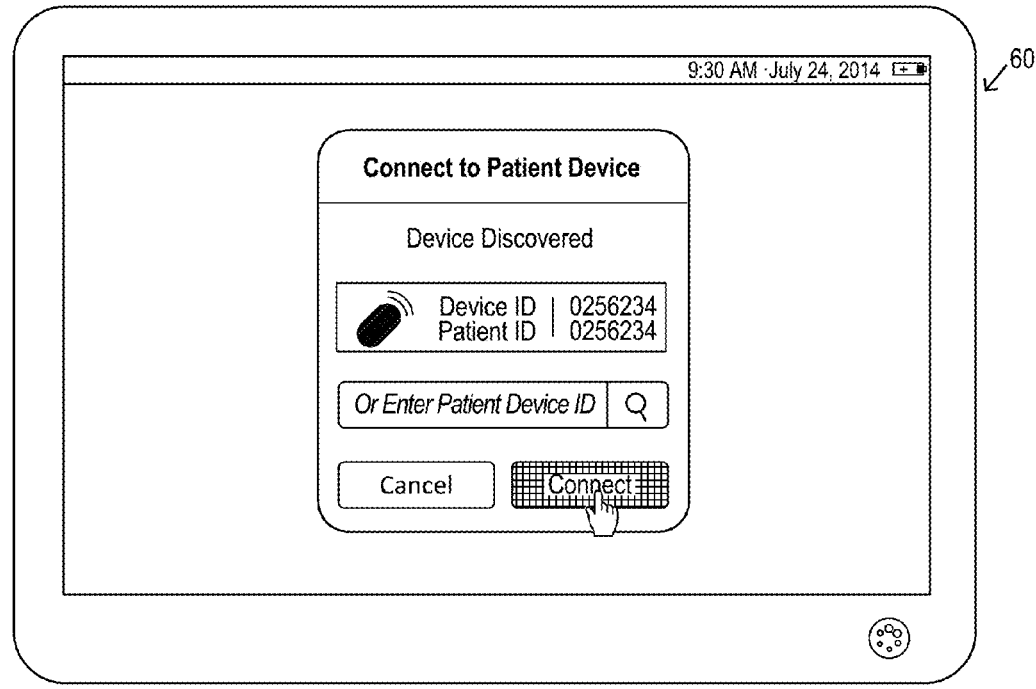
Figure 15K:
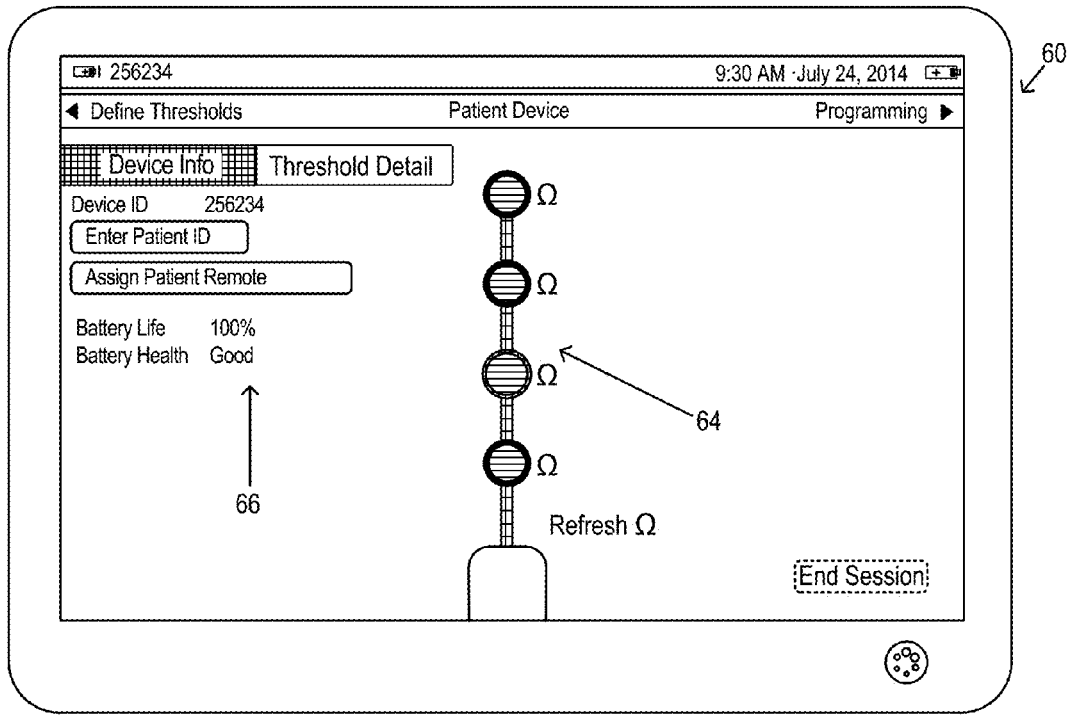
Figure 15L:
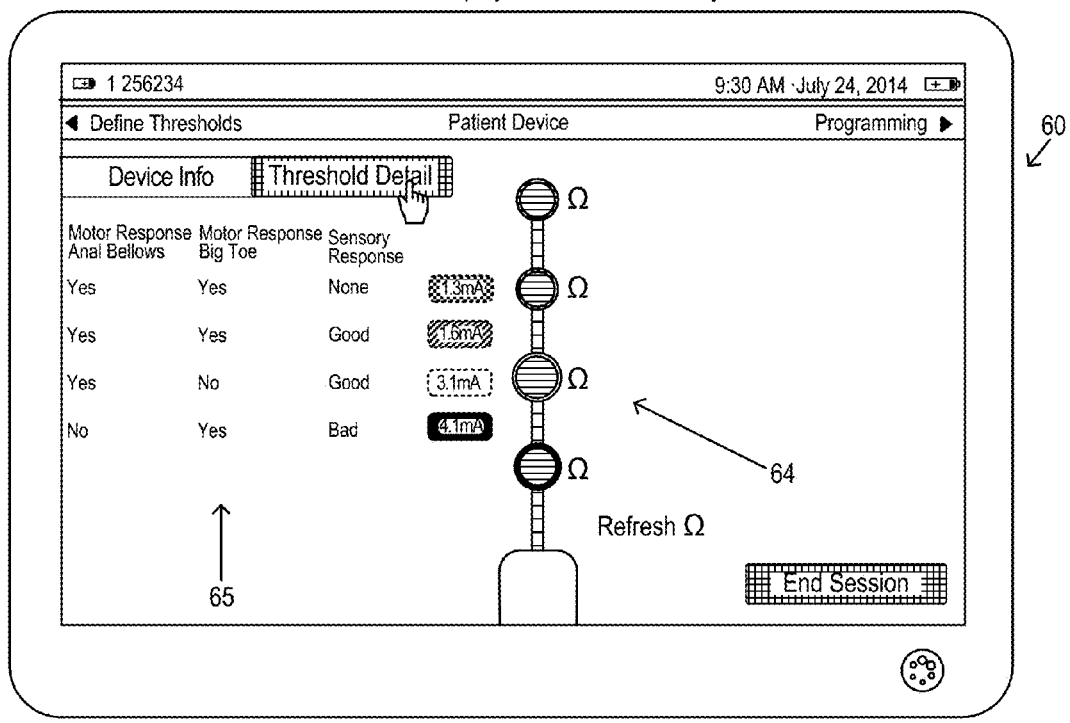

In one aspect, the CP 60 connects to the EPG/IPG and establishes communication, which may be indicated on the graphical user interface as shown in FIG. 15J. The CP can obtain and review EPG/IPG device info and record the stimulation levels on the EPG/IPG and/or associate the EPG/IPG with the recorded stimulation levels, as shown in FIG. 15K. The graphical user interface may include a Threshold Detail Display 65 that displays a summary of EMG motor responses, as well as recorded sensory responses and amplitude thresholds, as shown in FIG. 15L.

In order to confirm correct lead placement, it is desirable for the physician to confirm that the patient has both adequate motor and sensory responses before transitioning the patient into the staged trial phase or implanting the permanent IPG. However, sensory response is a subjective evaluation and may not always be available, such as when the patient is under general anesthesia. Experiments have shown that demonstrating appropriate motor responses is advantageous for accurate placement, even if sensory responses are available. As discussed above, EMG is a tool which records electrical activity of skeletal muscles. This sensing feature provides an objective criterion for the clinician to determine if the sacral nerve stimulation results in adequate motor response rather than relying solely on subjective sensory criteria. EMG can be used not only to verify optimal lead position during lead placement, but also to provide a standardized and more accurate approach to determine electrode thresholds, which in turn provides quantitative information supporting electrode selection for subsequent determinations of electrode recommendation and programming, discussed in further detail below. Using EMG to verify activation of motor responses can further improve the lead placement performance of less experienced operators and allow such physicians to perform lead placement with confidence and greater accuracy. Advantageously, as the positioning and programming functionality are integrated in many embodiments of the clinician programmer, at least some of the validation thresholds may be correlated to the subsequent stimulation programming, so that (for example) positioning is validated for a particular programming protocol to be used with that patient. Regardless, stimulation programming protocols may employ EMG data obtained during lead positioning or validation to more efficiently derive suitable neurostimulation treatment parameters for that patient.

While the above illustrates an example method of integrating the CP 60 with EMG measurements to assist in placement of the lead it is appreciated that various other aspects and features may be used in accordance with aspects of the invention. The following Table 2 illustrates various features of EMG enhanced lead placement used in a various devices as well as various other alternative features.

TABLE 2

EMG-enhanced Lead Placement

| | CP Device | | Alternate CP Device | |
|---|---|---|---|---|
| Step | Use of EMG | User feedback | Use of EMG | User feedback |
| General | Patch/surface EMG recording from bellows (perineal musculature) and big toe Display individual | Visual response, including indicator of max response amplitude | Patch/surface EMG recording from bellows (perineal musculature) and big toe Tool for automating the determination of | Visual response, including indicator of max response amplitude |

TABLE 2-continued

EMG-enhanced Lead Placement

| | CP Device | | Alternate CP Device | |
| --- | --- | --- | --- | --- |
| Step | Use of EMG | User feedback | Use of EMG | User feedback |
| | CMAP responses Visual bar used to indicate maximum CMAP response | | stimulation thresholds and evaluation of lead placement | |
| Foramen needle placement | EMG responses displayed during stimulation | Color-coded qualitative feedback of needle placement, based on stimulation amplitude Represents relative proximity to the sacral nerve | Stimulation increases automatically until an EMG response is evoked Increases rapidly until initial response is seen Increases slowly until maximum response is seen User has option to push button to stop stimulation at any time | Color-coded qualitative feedback of needle placement, based on stimulation amplitude Represents relative proximity to the sacral nerve |
| Initial lead placement | EMG responses displayed Calculate maximum EMG response for each contact at a given stimulation amplitude, then normalize value as % of response from reference contact | Visual feedback that represents relative distance of each contact from the target nerve, based on relative maximum EMG response values triggers off "reference contact" | (step is collapsed with "contact characterization") | (step is collapsed with "contact characterization") |
| Contact characterization | EMG responses displayed during stimulation | Color-coded qualitative feedback on contact based on stimulation amplitude and, captured by user input, the presence/absence of motor and sensory response | Stimulation increases automatically until an EMG response is evoked Increases rapidly until initial response is seen Increases slowly until maximum response is seen User has option to push button to stop stimulation at any time The CP stores the threshold data (presence of response, amplitude to evoke) and user can input sensory response | Color-coded qualitative feedback on contact based on stimulation amplitude and the presence/absence of motor and sensory response (auto-captured) and the presence/absence of sensory response (user input) |

IV. Neurostimulation Programming with EMG

After implantation of the lead and placement of the neurostimulation is verified with the CP using EMG, the CP can be used outside the operating room to program the IPG/EPG for delivery of the neurostimulation treatment. Programming may be performed using thresholds obtained from EMG obtained during and/or after lead placement and tested using EMG data associated with at least one neuromuscular response.

A. EMG Assisted Programming Setup

Figure 16A:
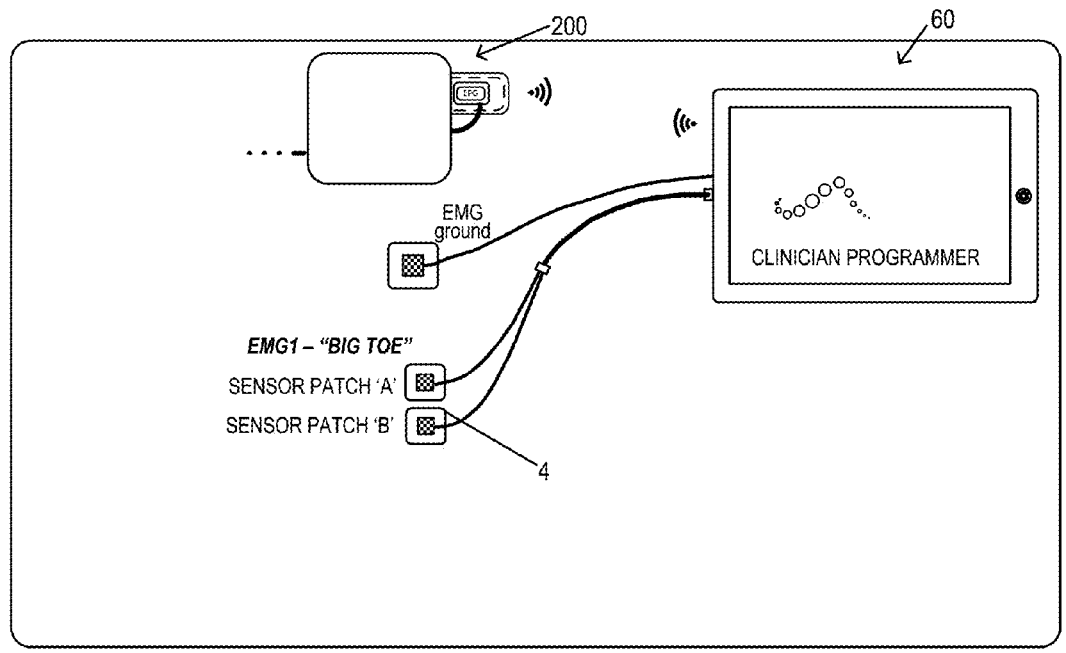
FIGS. 16A-16B illustrates system setups for conducting electromyography assisted programming of the neurostimulation system, in accordance with aspects of the invention.
Figure 16B:
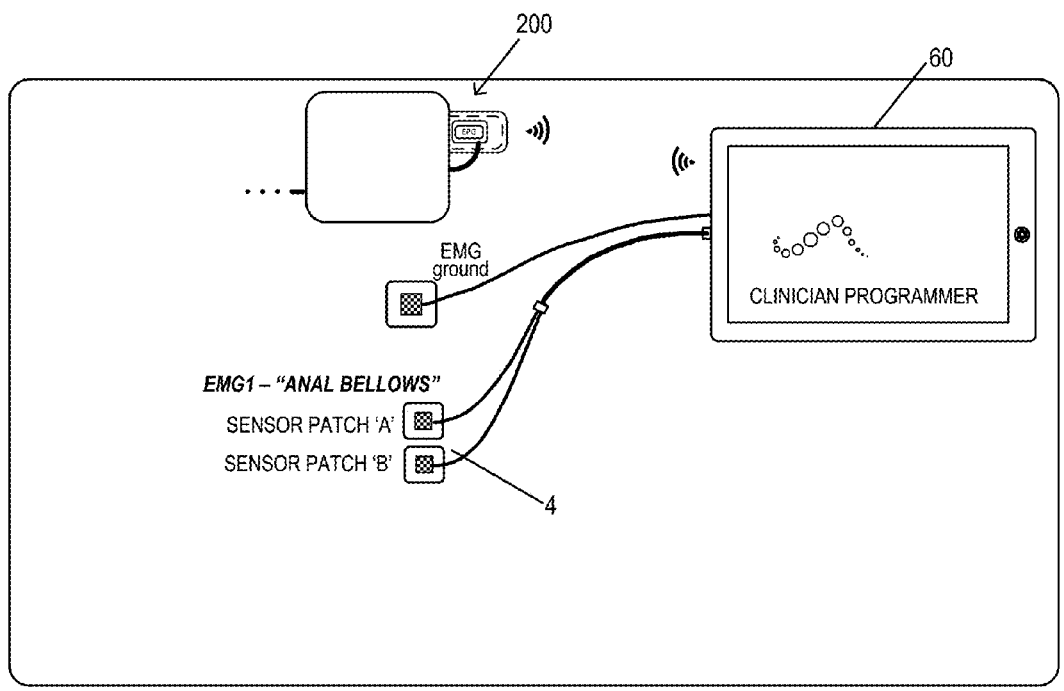

FIGS. 16A-16B illustrate example system setups for EMG assisted programming of the neurostimulation system using the CP, in accordance with aspects of the invention. Typically, this configuration is used for initial programming of the IPG/EMG, although it may also be used in re-programming. Re-programming may also utilized threshold data, EMG data or electrode configuration recommendation data accessed or determined during initial programming without otherwise obtaining new EMG data.

In one aspect, the integration of the EMG recording and display into the clinician tool used for lead placement and programming provides significant advantages over conventional programming methods, including a reduction in time required to determine a program that is efficacious in providing relief for the treated condition. In addition, the use of proportional increases in stimulation amplitude during test programming to reduce the time required for these activities. Recording of motor and sensory responses and stimulation amplitude thresholds directly into the CP during lead placement and conversion of these responses into feedback on the quality of programming recommendations. In another aspect, methods may utilize an EMG recording of a single neuromuscular response (e.g. big toe) to verify the appropriate electrode position and selection and then tune down the amplitude so as to avoid invoking the neuromuscular response during long term therapy stimulation. This aspect may simplify and reduce the time associated with programming of the neurostimulation device as well as improve patient comfort during programming and long term therapy. In another aspect, the CP is configured with an automated threshold determination based on EMG responses to provide rapid feedback during lead placement and to identify optimal programming parameters.

In some embodiments, the system is configured to have EMG sensing capability during re-programming, which is particularly valuable. Stimulation levels during re-programming are typically low to avoid patient discomfort which often results in difficult generation of motor responses. Involuntary muscle movement while the patient is awake may also cause noise that is difficult for the physician to differentiate. In contrast to conventional approaches, EMG allows the clinician to detect motor responses at very low stimulation levels at which the responses are not visible to the naked eye, and help them distinguish a motor response originated by sacral nerve stimulation from involuntary muscle movement.

In some embodiments, the system stores the last four programs used onboard a memory of the IPG/EPG. This is particularly advantageous for reprogramming as it allows a physician to access the most recent programs used in the neurostimulation with an entirely different CP that may not otherwise have access to the programming information. In another aspect, the programming data may be accessible online or on a cloud serve and associated with an unique identifier of a given IPG/EPG such that a different CP could readily access and download programming information as needed for re-programming.

B. Electrode Characterization

In one aspect, during lead placement, the CP 60 can utilize the thresholds previously recorded in characterizing each electrode as to its suitability for use in neurostimulation. In some embodiments, the CP 60 is configured to program the IPG/EPG with an EMG recording from only one muscle, either the anal bellows or the big toe response. Such programming can also utilize a visual observation of the response as well as the recorded maximum response amplitude. In one aspect, the CP 60 performs programming without requiring an anal bellow response observation or EMG waveform measurement of an anal bellows response. In some embodiments, the CP 60 performs programming using an EMG recording from only the big toe response, such as shown in FIG. 15C in which the graphical user interface of the CP displays only the Big Toe EMG waveform display 63. In an alternative embodiment, the CP 60 can be used to program the EPG/IPG using an EMG from only the anal bellows response.

In one aspect, the EMG recording may be that obtained during lead placement, or more typically, obtained during programming so that the patient can provide subjective sensory response data concurrent with performing a big toe response with a given electrode during testing. The programming may further include visual observations of the big toe response and/or the maximum response amplitude obtained during programming. Allowing programming of the IPG/EPG without requiring an anal bellow response is advantageous since the patient is not under general anesthesia while programming is performed and the anal bellows response can be uncomfortable and painful for the patient. This also allows the CP to receive subjective sensory data from the patient during programming as to any discomfort, paresthesia or pain associated with stimulation of a particular electrode configuration. The following Table 3 shows various features of EMG-enabled neurostimulation programming of the IPG/EPG with the CP as used in various devices as well as alternative features.

In one aspect, the electrodes can be configured to deliver neurostimulation in varying electrode configurations, for example, neurostimulation may be delivered in a monopolar mode from one or more of the electrodes in various combinations and sequences and/or in a bi-polar mode between two or more electrodes in various combinations and sequences. The suitability of the programming can be determined by use of the electrode characterizations described above determined from EMG recording of at least one neuromuscular response, typically the big toe response, and may further include visual response and amplitude data and subject sensory response data from the patient. From these characterizations, the CP determines multiple electrode configuration recommendations, which may be provided on the graphical user interface of the CP 60 on the Electrode Recommendation display 67 to allow the physician to review and select each recommendation for subsequent testing.

C. Electrode Configuration Recommendations

Figure 17:
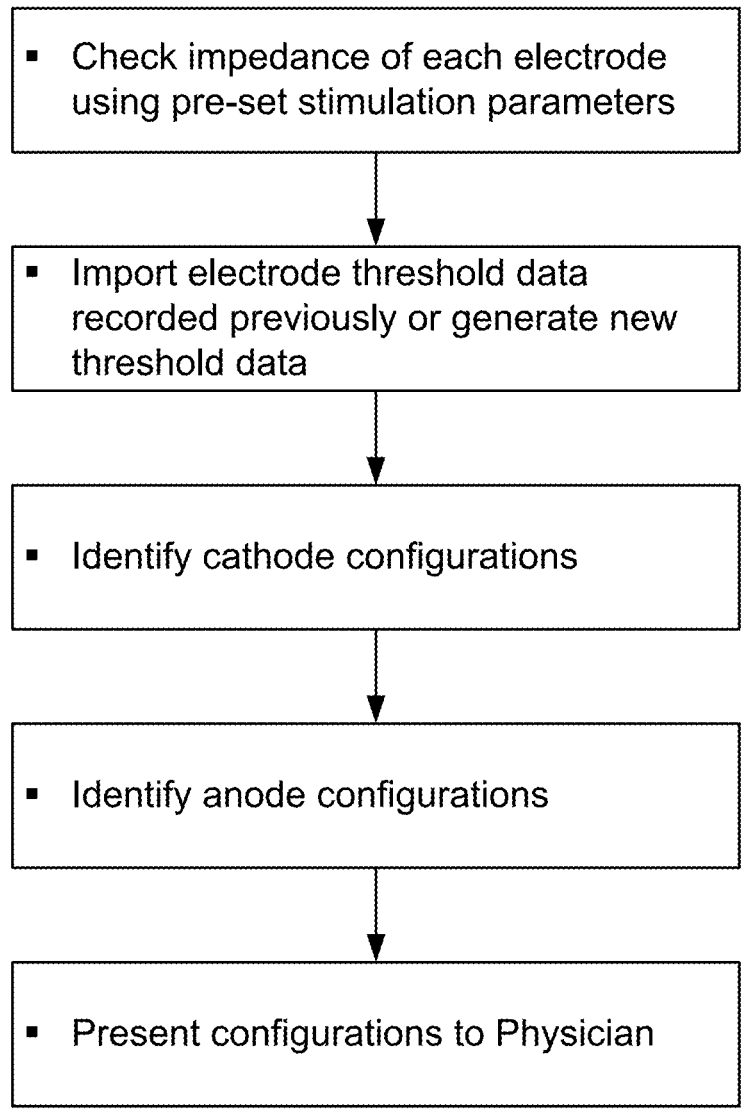
FIG. 17 illustrates an example method by which electrode configuration recommendations are determined and provided to a physician during programming, in accordance with aspects of the invention.

In one aspect, the system configuration determines multiple electrode configuration recommendations based on using electrode characterization and/or threshold data based in part on EMG recordings of the electrodes and provides the recommendations to the user. FIG. 17 illustrates an example method of determining and providing electrode configuration recommendations implemented with a CP. In such methods, the system first checks the impedance of each electrode using pre-set stimulation parameters and may lock out any electrode with unacceptable impedance (<50 or >3,000 Ohms) from being assigned as an anode or cathode. The system then identifies threshold data associated with each electrode, either from data recorded previously during lead placement or by generating new threshold data. The system tiers the electrodes based on the threshold values (e.g. "good," "ok," "bad") and rank the electrodes within each tier. Any electrodes that result in an unpleasant sensation are excluded from being used as a cathode. The system then determines multiple electrode configuration recommendation, preferably at least four differing configurations, according to pre-determined rules and are then presented to the clinician using the CP.

In one aspect, the electrode configurations are determined based on the threshold data according to the following rules: (1) Assign single cathode configurations for each contact in the "Good" tier, prioritized from farthest pair to closest pair; (2) Assign single cathode configurations for each contact in the "Good" tier, prioritized from lowest to highest threshold; (3) Assign double cathode configurations for each pair of adjacent electrodes in "Good" tier, prioritized by lowest combined threshold; (4) Assign single cathode configurations for each contact in the "OK" tier, prioritized from lowest to highest threshold; and (5) Assign double cathode configurations for each pair of adjacent electrodes from "Good" and "OK" tiers, prioritized by lowest combined threshold. The anodes for the cathode configurations are assigned as follows: for monopolar configuration, the IPG housing or "can" is assigned as the anode; for bipolar configuration, the electrode furthest from the cathode with acceptable impedance is assigned as the anode.

Figure 18:
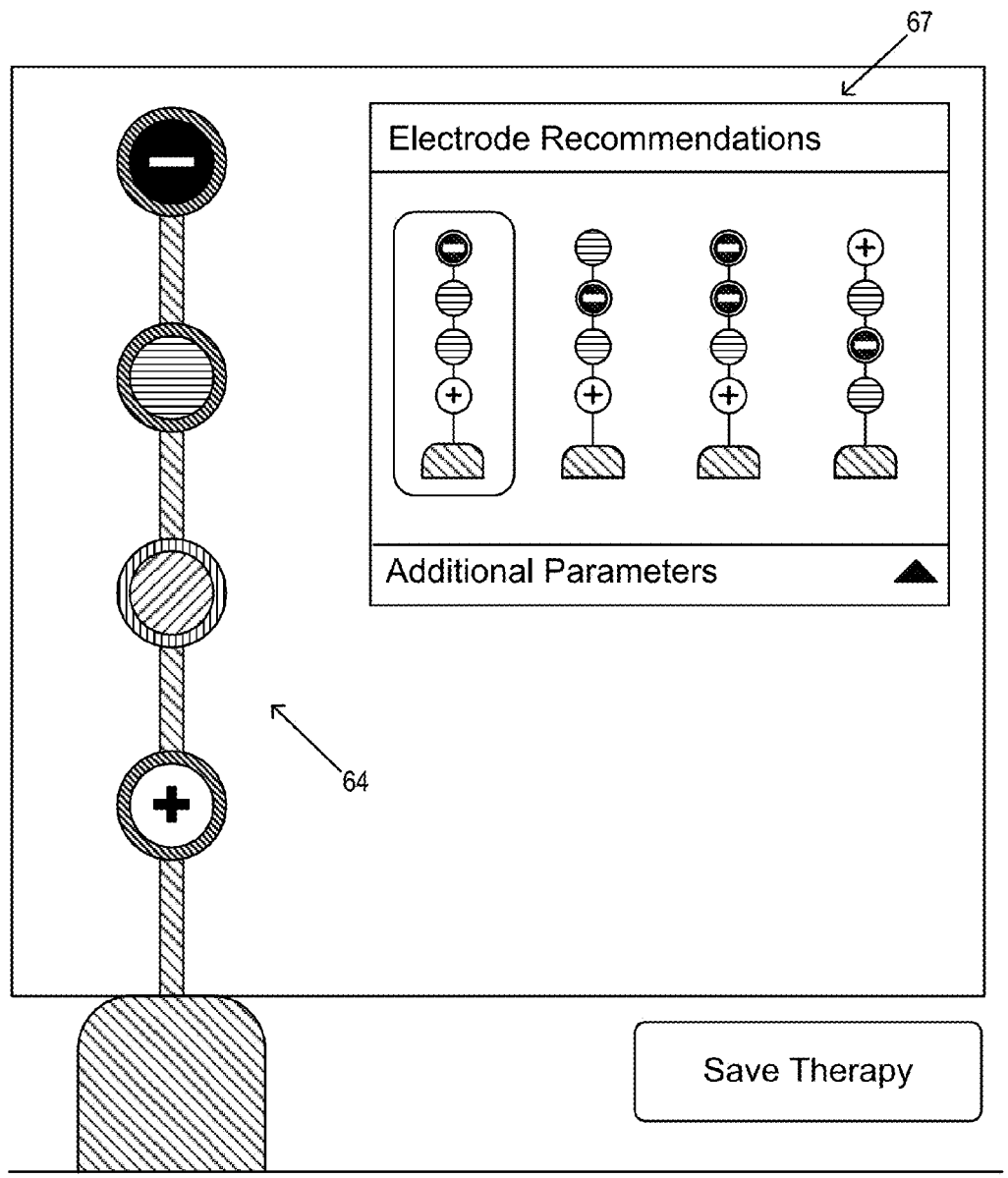
FIG. 18 illustrates an example electrode configuration recommendation for display on a clinician programmer during programming and/or reprogramming of a neurostimulation system, in accordance with aspects of the invention.

After identification of the electrode configuration recommendations, the system presents the electrode configuration recommendations to the physician, typically on a user interface of the CP such as shown in FIG. 18, on which the physician may select any of the electrode configurations for testing, modify a recommended electrode configuration as desired, or create a new electrode configuration. In one aspect, the system presents the electrode configuration recommendations within a selectable menu and may include one or more default values or attributes for a given electrode recommendation.

In one aspect, in an idealized setting in which each of the electrodes has a "good" impedance, the system simply recommends each of the contacts as a single cathode. Although it is desirable to have four "good" electrodes, it is acceptable to have at least three "good" electrodes for initial programming. The above algorithm recommends the best electrode selection for a given case. While each physician may have their own way to select electrode for programming, providing a set of electrode configuration recommendations that are easily viewed and selected by the physician helps standardize the process, reduce the duration of the procedure and provide improve patient outcomes, particularly for inexperienced implanters or minimally trained personnel.

In one aspect, the above algorithm assumes a single input parameter for the electrode threshold. In some embodiments, the system allows the physician to select, through the CP, what parameter(s) (sensory or motor responses or in combination) to use to determine the threshold for each electrode. The physician can also select whether to rely on EMG feedback or not for threshold determination. In another aspect, qualitative sensory feedback will be considered in electrode selection, e.g., if a patient reports unpleasant sensation for any specific electrode, this electrode will be excluded from being used as cathode. In another aspect, the algorithm prioritizes single cathode over double cathodes for all contacts in the "good" tier. In some embodiments, the electrodes are tiered according to the following tiers: "good"="1-3 mA"; "ok"="0.5-1 mA" and "3-4 mA"; "bad"="<0.5 mA" and ">4 mA."

FIGS. 19A-19B depict case studies illustrating selection of four electrode recommendations for a bipolar and monopolar treatment according to the algorithms described above for each case 1 in FIG. 19A and case 2 in FIG. 19B.

D. Program Selection, Modification and Testing

In programming the neurostimulation system, an EMG signal can be used to evaluate programming quality by allowing user to see if a motor response is evoked by stimulation. In some embodiments, the user can manually observe EMG responses and enter the observations into the CP and try to set a stimulation amplitude at a level that evokes a desired motor response.

Figure 20A:
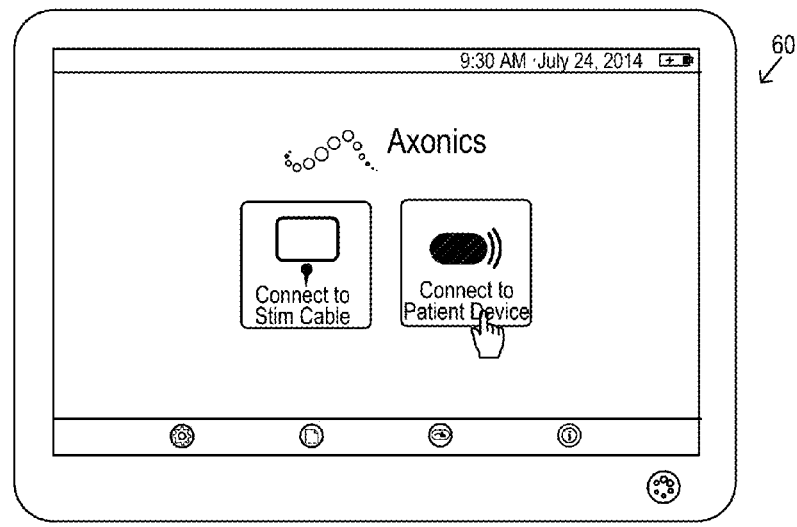
FIGS. 20A-20K illustrate a graphical user interface display of a clinician programmer during an alternative electromyography assisted neurostimulation lead placement procedure, in accordance with aspects of the invention. in accordance with aspects of the invention
Figure 20B:
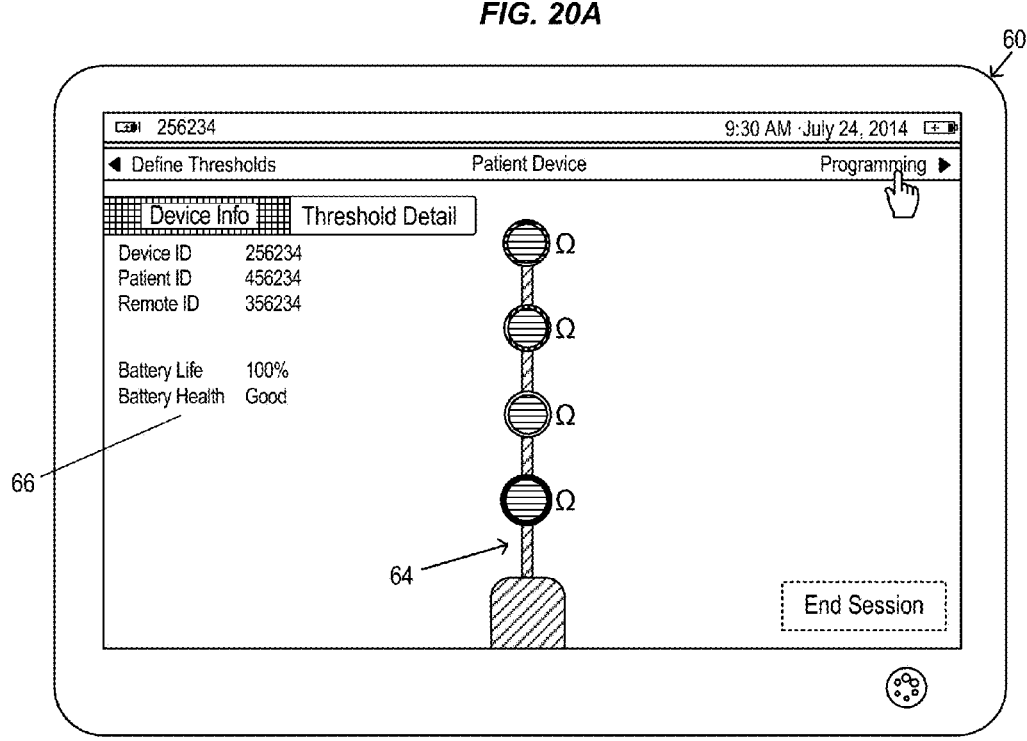

FIGS. 20A-20K illustrate the graphical user interface of the CP during initial programming and testing. FIG. 20A depicts the CP 60 re-connecting with the patient device and verifying the device info. The physician can confirm this by viewing the device info display 66 shown in FIG. 20B before proceeding with programming. FIG. 20B is the IPG data display which shows the threshold summary and contact status. The threshold data from "lead placement" will be recorded and can be viewed in summary form on this page. Symbols to right of each contact represent the impedance associated with that contact: Green ("good"): 50-3,000 Ohms, Red ("bad"): <50 or >3,000 Ohms. In some embodiments, yellow may indicate "marginal," while in other embodiments there will not be a yellow option. The colored circles around each contact represent the qualitative assessment of that contact from lead placement. It is a summary of the information in the "threshold detail" tab. As shown in FIG. 20B, electrodes #0 and #1 are shown in green, electrode #2 is shown as orange, and electrode #3 is shown as red. In one aspect, the CP 60 can program the IPG/EPG without re-attaching to EMG patches by use of the electrode information and EMG waveforms and/or visual response and patient sensory data obtained by the CP 60 during lead placement. More typically, additional EMG data is obtained during programming from EMG patches coupled to the patient to detect at least one neuromuscular response. Programming may also utilize visual response data and sensory data obtained from the patient during programming.

Figure 20C:
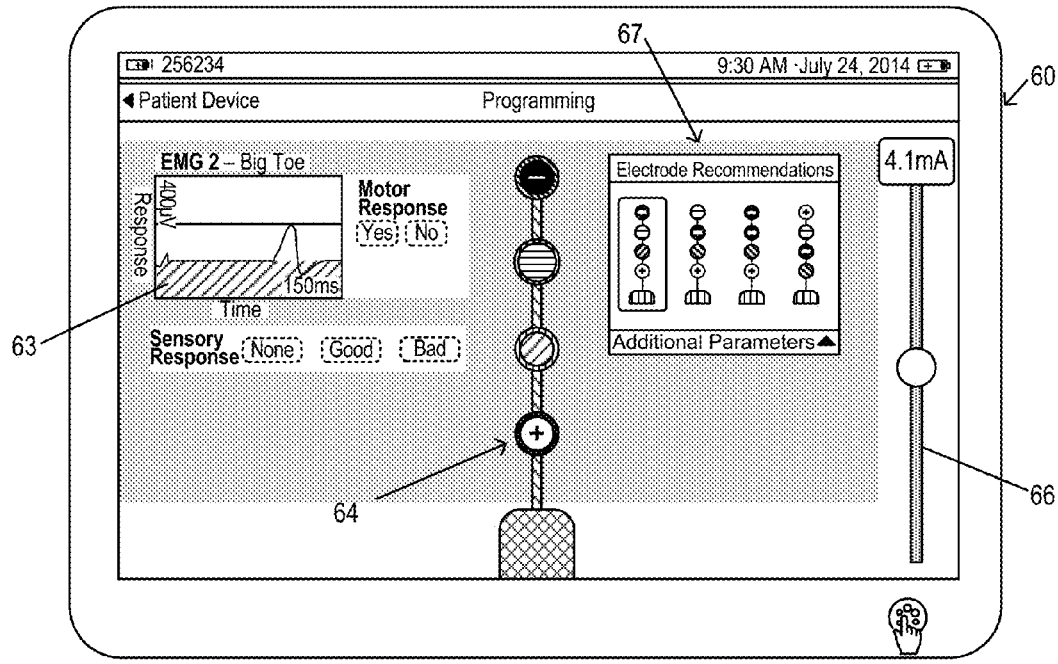

FIG. 20C illustrates programming of the IPG and testing of the first electrode configuration recommendation shown on display 67, which shows four electrode configuration recommendations determined according to the algorithms discussed above. The electrode configuration recommendations are based off input from the Threshold Detail determined during lead placement characterization (see FIG. 15I). It is appreciated that the electrode thresholds could also be determined during programming. Colored circles around each contact represent the qualitative assessment of that contact from lead placement. It is a summary of the information in the "threshold detail" tab. The presence of motor response and quality of the sensory response is manually recorded for retrospective data analysis purposes. The amplitude adjustment can be done in an auto-adjusting increments or fixed increments as discussed previously.

Figure 20D:
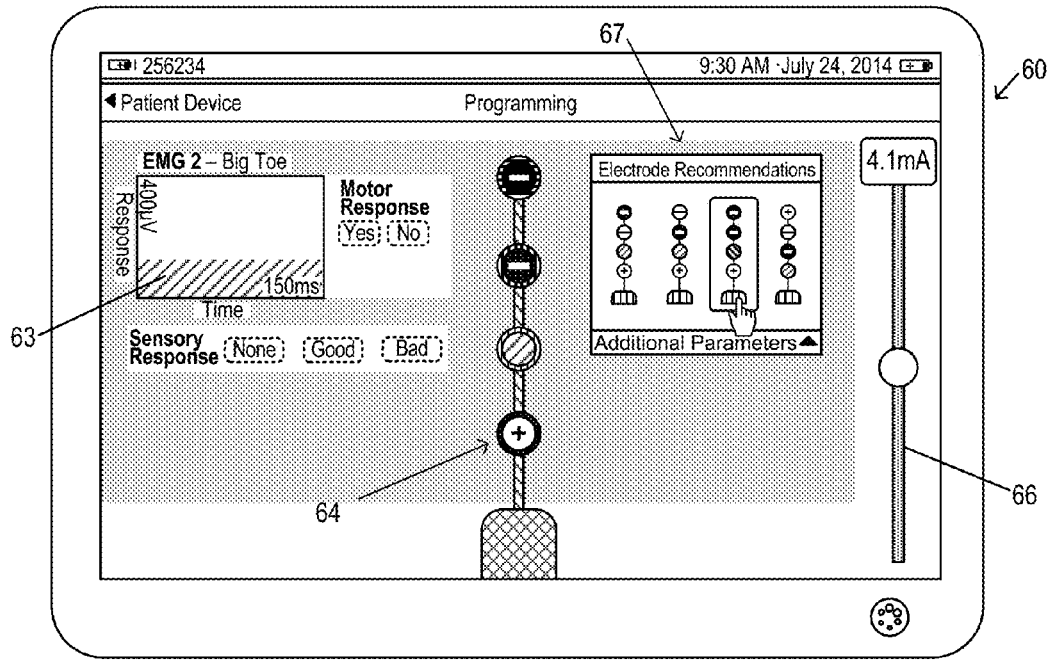

In the first electrode configuration recommendation in FIG. 20C, the lead operates in a bi-polar mode between electrodes 0 and 3, electrode #0 acting as the cathode and electrode #3 acting as the anode. The big toe response and amplitude is recorded during stimulation of the first configuration and the visually observed motor response and the subjective sensory response from the patient is entered through the display. The same procedure is repeated for each of the four electrode recommendations, as shown in FIG. 20D, in which a double cathode configuration is being tested.

Figure 20E:
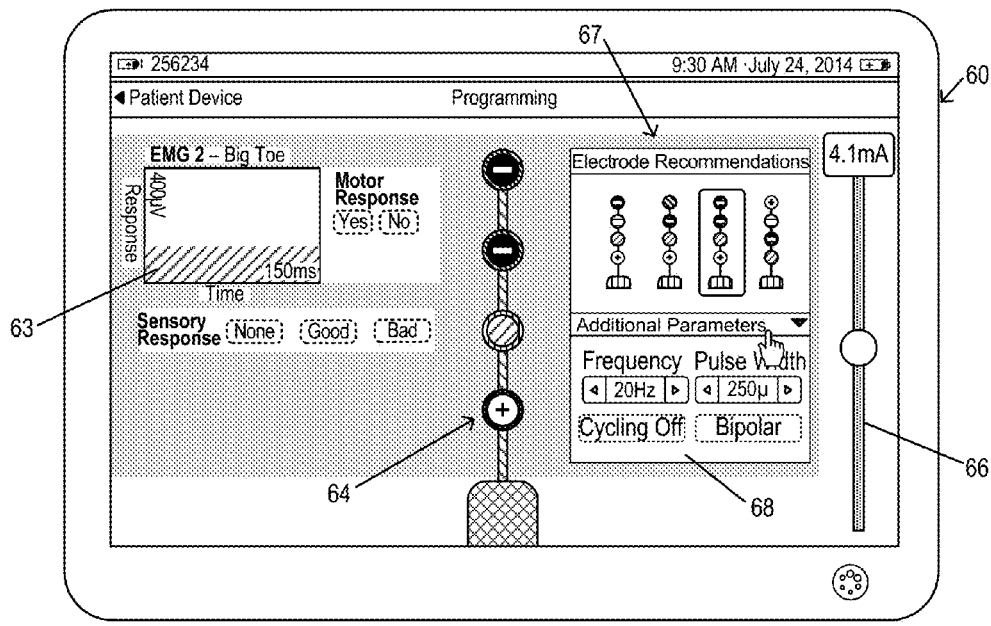
Figure 20F:
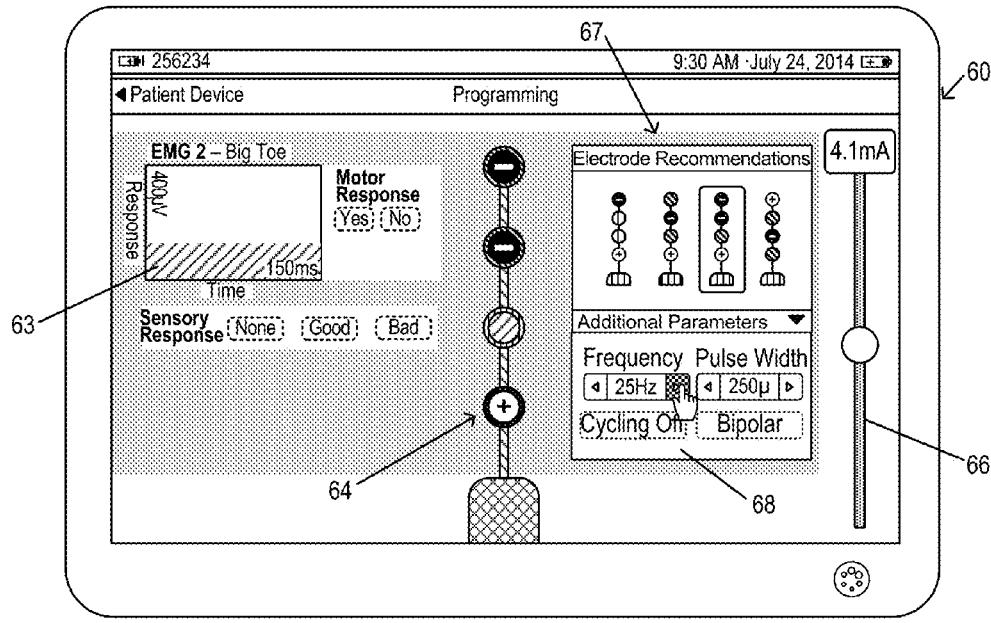
Figure 20G:
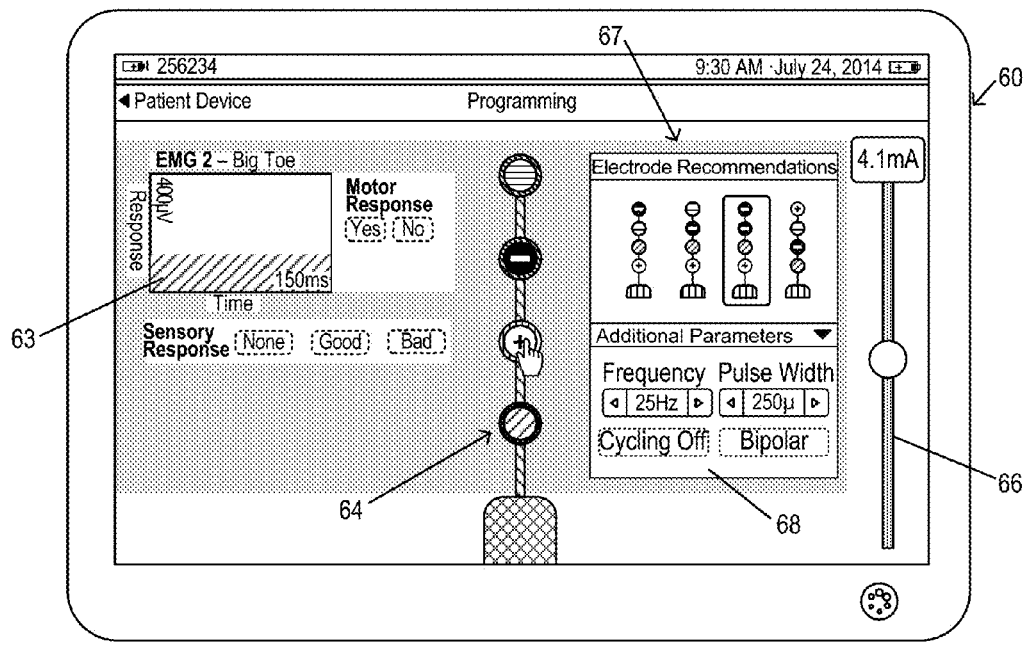
Figure 20H:
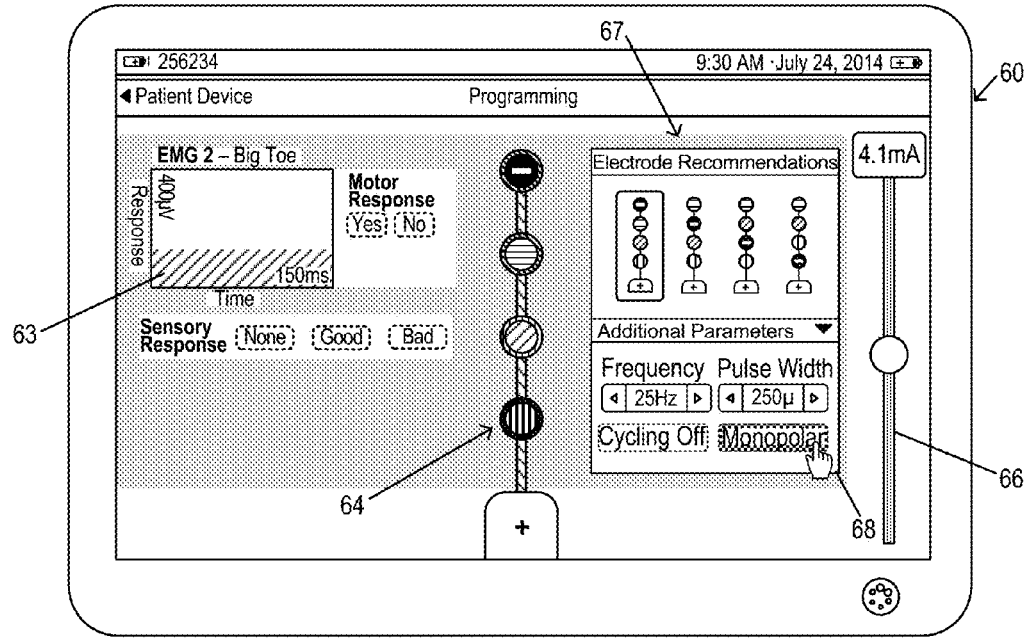
Figure 20I:
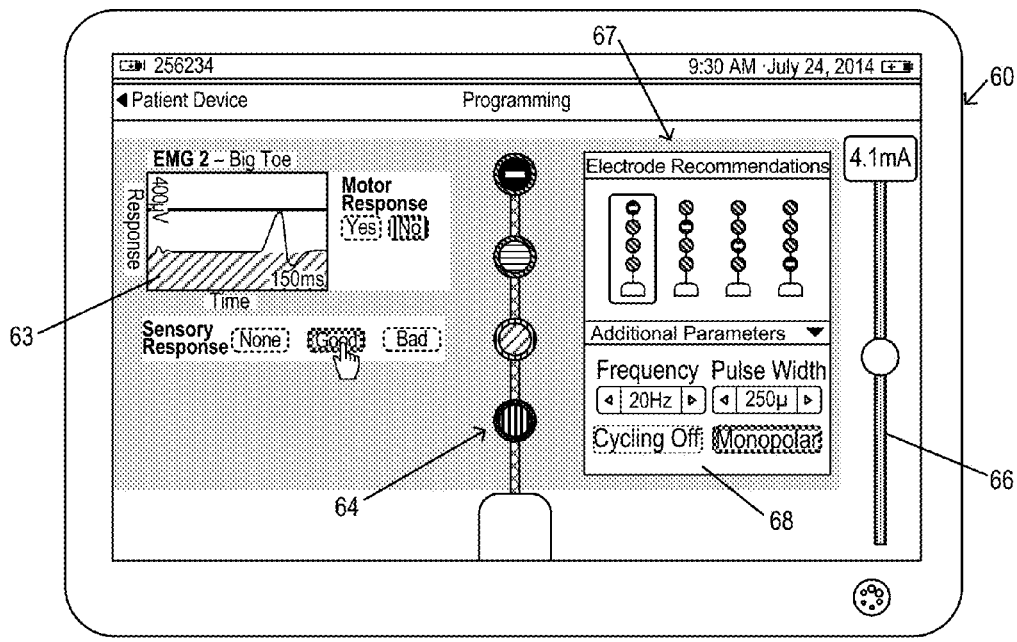
Figure 20J:
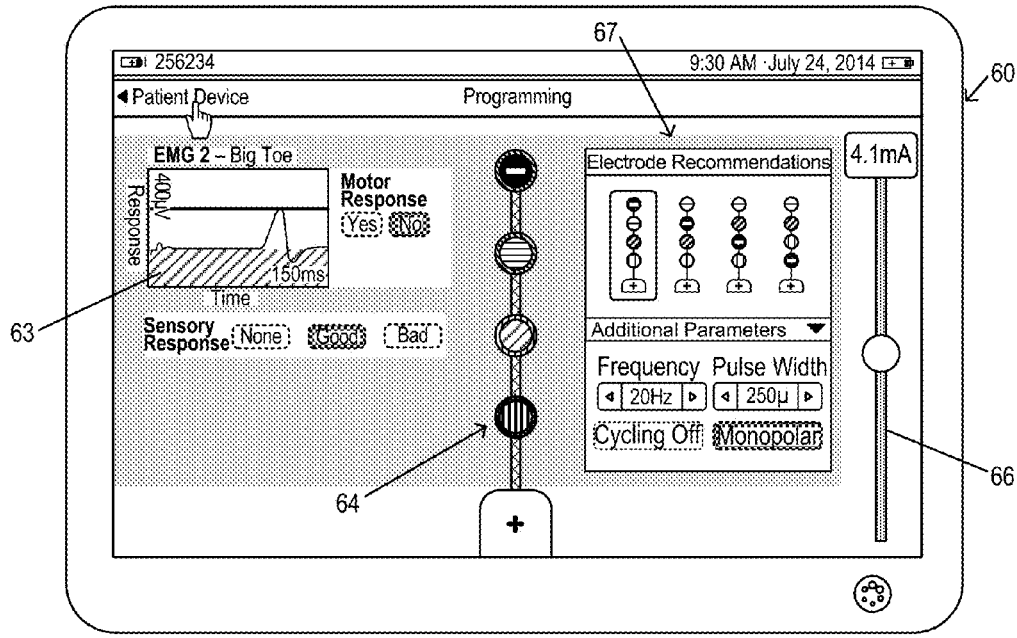
Figure 20K:
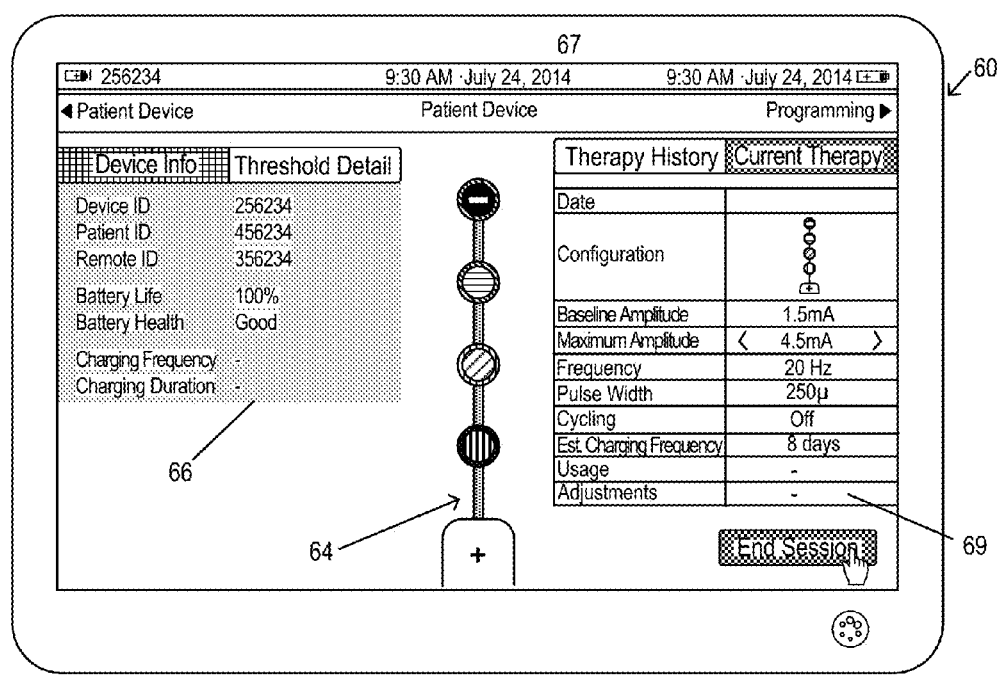

In one aspect, the graphical user interface allows the user to adjust various parameters associated with each of the recommended electrode configurations being tested. For example, as shown in FIG. 20E, the graphical user interface of the CP 60 includes an Additional Parameters display 68 in which the physician select and adjust various parameters (e.g. Frequency, Pulse Width, Cycling and Mode) associated with each electrode configuration as needed for a particular therapy and/or patient. After adjustment, the EMG response and amplitude data can be updated and recorded in the CP 60. In another aspect, the physician may re-assign the electrode polarity associated with a given electrode configuration recommendation using the CP, such as shown in FIG. 20G, in which the cursor can be used to change the electrode polarity on the electrode status display 64. In yet another aspect, the user may switch between bipolar and mono-polar modes by selecting the Mode button in the Additional Parameters display 68. Upon selection of mono-polar mode, the CP 60 will display multiple mono-polar electrode configuration recommendations, as shown in FIG. 20H. When the physician is satisfied with the electrode configuration settings, the physician may proceed to save the settings in the CP 60 by selecting the Patient Device menu, as shown in FIG. 20J, confirming the therapy settings, such as viewing the Current Therapy display 69 shown in FIG. 20K, and saving the therapy to the Patient Device, after which the IPG/EPG are fully programmed and the CP 60 may be detached.

In one aspect, after programming of the IPG/EPG in accordance with the above described methods, the patient evaluates the selected program over a pre-determined period of time. Typically, the patient is able to make limited adjustments to the program, such as increasing or decreasing the amplitude or turning the treatment off. If after the assessment period, the patient has not experienced relief from the treated condition or if other problems develop, the patient returns to the physician and a re-programming of the IPG/EPG is conducted with the CP in a process similar to the programming methods described above, to select an alternative electrode configuration from the recommended configuration or to develop a new treatment program that provides effective treatment.

TABLE 3

EMG-enabled Neurostimulation Programming

| Step | CP Device | | Alternate CP Device | |
|---|---|---|---|---|
| | Use of EMG | User feedback | Use of EMG | User feedback |
| General | Patch/surface EMG recording from only 1 muscle (either bellows or big toe) | Visual response, including indicator of max response amplitude | Patch/surface EMG recording from only 1 muscle (either bellows or big toe) | Visual response, including indicator of max response amplitude |
| Electrode characterization | EMG responses displayed during stimulation | Visual response indicates whether or not the electrode is activating the target nerve (e.g., confirms placement still good) | Stimulation automatically screens each contact to verify a motor response can be evoked | Simple display to indicate whether each contact is good/bad |
| Parameter selection | EMG responses displayed during stimulation | Visual response indicates whether or not the selected amplitude sufficient to evoke a response | Stimulation increases automatically and gives a simple indication of when an intial EMG response and a maximum response are evoked User can stop stimulation if patient becomes uncomfortable | Simple visual representation lets the user know a response has been evoked |

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A method for improved positioning of an implantable neurostimulation lead in a patient with clinician programmer coupled to the implantable lead for treatment of bladder and/or bowel dysfunction, wherein the implantable lead comprises at least four neurostimulation electrodes, and at least one EMG sensing electrode minimally invasively positioned on a skin surface or within the patient, the method comprising:

delivering a first test stimulation at a stimulation amplitude level from the clinician programmer to a nerve tissue of the patient with a principal electrode of the implantable lead, wherein the principal electrode is selected from the at least four neurostimulation electrodes of the implantable lead;

delivering another test stimulation at a same stimulation amplitude level for a same period of time sequentially to each remaining electrode for the at least four electrodes of the implantable lead from the clinician programmer;

receiving, with the clinician programmer, EMG information based on recording a stimulation-induced EMG motor response for each test stimulation on each electrode of the implantable lead via the at least one EMG sensing electrode so as to provide improved lateral and/or axial resolution of the at least four electrodes relative to a target nerve for positioning of the implantable lead at a target stimulation region along the target nerve for treatment of bladder and/or bowel dysfunction;

outputting feedback on a graphical user interface of the clinician programmer, the feedback based on the EMG information associated with the first test stimulation of the principal electrode and the other test stimulations of remaining electrodes, the feedback indicating proximity of the at least four electrodes relative the target nerve so as to facilitate improved placement of the at least four electrodes along the target nerve; and repeating steps of: delivering a test stimulation to the principle electrodes and each remaining electrode at a same stimulation and period of time, receiving EMG information based on recording a stimulation-induces EMG motor response for each test stimulation, and outputting feedback on the graphical user interface of the clinician programmer based on the EMG information until the EMG information is indicative of multiple electrodes of the at least four neurostimulation electrodes being within the target stimulation region along the target nerve.

2. The method of claim 1, further comprising:
selecting a principal electrode based on a user input received via the graphical user interface of the clinician programmer.

3. The method of claim 1, further comprising:
automatically adjusting the stimulation amplitude level of the test stimulation for the principal electrode until a desired stimulation-induced motor response is detected by use of EMG and received by the clinician programmer.

4. The method of claim 3, wherein automatically adjusting comprises increasing the stimulation amplitude in increments of 0.05 mA for a test stimulation less than or equal to 1 mA.

5. The method of claim 3, wherein automatically adjusting comprises any of:
increasing the stimulation amplitude in increments of 0.05 mA for a test stimulation less than or equal to 1 mA;

increasing the stimulation amplitude in increments of 0.1 mA for a test stimulation more than or equal to 1 mA and less than or equal to 2 mA;

increasing the stimulation amplitude in increments of 0.2 mA for a test stimulation more than or equal to 2 mA and less than or equal to 3 mA; and increasing the stimulation amplitude in increments of 0.25 mA for a test stimulation more than or equal to 3 mA.

6. The method of claim 1, further comprising receiving a user input related to adjustment of the stimulation amplitude level of the test stimulation for the principal electrode in increments in a range from 0.05 mA to 0.25 mA to achieve a desired stimulation-induced motor response indicated via an EMG and shown on a graphical user interface of the clinician programmer.

7. The method of claim 1, wherein the period of time is such that a sweeping cycle of the implantable lead is completed in 5 seconds or less.

8. The method of claim 1, further comprising:
calculating an EMG response value for each test stimulation delivered at a given stimulation amplitude level to each electrode based on a maximum EMG response amplitude associated with each electrode.

9. The method of claim 1, further comprising:
calculating an EMG response value for each test stimulation delivered at a given stimulation amplitude level to each electrode based on a maximum EMG response amplitude associated with each electrode which is normalized relative to an EMG response amplitude associated with the principal electrode.

10. The method of claim 9, wherein the visual feedback is based at least in part on the EMG response value associated with each electrode and indicates to a user on how to laterally or axially position the implantable lead at the target stimulation region via a graphical user interface of the clinician programmer.

11. The method of claim 9, further comprising calculating a relative distance or position of each electrode to the target stimulation region based on the EMG response value associated with each electrode.

12. The method of claim 11, further comprising:
repeating the delivering test stimulations to each of the at least four electrodes of the implantable lead and recording steps after lead re-positioning to confirm the calculated EMG response value for each electrode are within a desired value range, or to confirm the maximum EMG response amplitude for each electrode are within a desired response range and the associated stimulation amplitude for each electrode is within a desired stimulation range.

13. The method of claim 1, wherein the lead is inserted through a foramen of a sacrum of the patient and positioned in proximity of a sacral nerve root of the patient so as to treat bladder and/or bowel related dysfunction of the patient.

14. The method of claim 1, further comprising displaying a visual image of the recorded stimulation-induced motor response during each test stimulation on a graphical user interface of the clinician programmer, wherein the visual image includes a waveform comprising a compound muscle action potential (CMAP).

15. The method of claim 1, further comprising:
validating lead placement by testing for a stimulation amplitude threshold for each electrode.

16. The method of claim 15, further comprising:
receiving a user input related to an adjustment of the stimulation amplitude threshold of the test stimulation for each electrode in increments in a range from 0.05 mA to 0.25 mA to achieve a desired stimulation-induced motor response at a minimum stimulation amplitude threshold via a graphical user interface of the clinician programmer.

17. The method of claim 16, further comprising displaying visual feedback to a user on the stimulation amplitude threshold for each electrode via a graphical user interface of the clinician programmer, wherein the visual feedback comprises color coding from at least three contrasting colors.

18. A method for improved positioning of an implantable neurostimulation lead in a patient with an integrated electromyography (EMG) and stimulation clinician programmer coupled to the implantable lead for treatment of bladder and/or bowel dysfunction, wherein the implantable lead comprises at least four neurostimulation electrodes, and the integrated clinician programmer is further coupled to at least one EMG sensing electrode minimally invasively positioned on a skin surface or within the patient, the method comprising:

delivering a first test stimulation at a stimulation amplitude level from the integrated clinician programmer to a nerve tissue of the patient with a principal electrode of the implantable lead, wherein the principal electrode is selected from the at least four neurostimulation electrodes of the implantable lead;

delivering another test stimulation at a same stimulation amplitude level for a same period of time sequentially to each remaining electrode of the at least four electrodes of the implantable lead from the integrated clinician programmer;

recording via EMG a stimulation-induced motor response with the integrated clinician programmer for each test stimulation on each electrode of the implantable lead via the at least one EMG sensing electrode so as to provide improved lateral and/or axial resolution of the at least four electrodes relative a target nerve for positioning of the implantable lead at a target stimulation region along the target nerve for treatment of bladder and/or bowel dysfunction;

outputting feedback on a graphical user interface of the integrated clinician programmer, the feedback based on the EMG information associated with the first test stimulation of the principal electrode and the other test stimulations of remaining electrodes, the feedback indicating proximity of the at least four electrodes relative the target nerve so as to facilitate improved placement of the at least four electrodes along the target nerve; and repeating steps of: delivering a test stimulation to the principle electrode and each remaining electrode at a same stimulation and period of time, recoding via EMG a stimulation-induces motor response for each test stimulation, and outputting feedback on the graphical user interface of the clinician programmer based on the EMG recordings until the EMG recording are indicative of multiple electrodes of the at least four neurostimulation electrodes being in the target stimulation region along the target nerve the second occurrence of.

19. The method of claim 18, further comprising:
selecting a principal electrode based on a user input received via the graphical user interface of the integrated clinician programmer.

20. The method of claim 18, further comprising:
automatically adjusting the stimulation amplitude level of the test stimulation for the principal electrode until a desired stimulation-induced motor response is detected.

21. The method of claim 20, wherein automatically adjusting comprises any of: increasing the stimulation amplitude in increments of 0.05 mA for a test stimulation less than or equal to 1 mA; increasing the stimulation amplitude in increments of 0.1 mA for a test stimulation more than or equal to 1 mA and less than or equal to 2 mA; increasing the stimulation amplitude in increments of 0.2 mA for a test stimulation more than or equal to 2 mA and less than or equal to 3 mA; increasing the stimulation amplitude in increments of 0.25 mA for a test stimulation more than or equal to 3 mA; or any combination thereof.

22. The method of claim 18, further comprising receiving a user input related to adjustment of the stimulation amplitude level of the test stimulation for the principal electrode in increments in a range from 0.05 mA to 0.25 mA to achieve a desired stimulation-induced EMG motor response via a graphical user interface of the integrated clinician programmer.

23. The method of claim 18, wherein the period of time is such that a sweeping cycle of the implantable lead is completed in 5 seconds or less.

24. The method of claim 18, further comprising:
calculating an EMG response value for each test stimulation delivered at a given stimulation amplitude level to each electrode based on a maximum EMG response amplitude associated with each electrode, or
calculating an EMG response value for each test stimulation delivered at a given stimulation amplitude level to each electrode based on a maximum EMG response amplitude associated with each electrode which is normalized relative to an EMG response amplitude associated with the principal electrode.

25. The method of claim 24, wherein the visual feedback is based at least in part on the EMG response value associated with each electrode and indicates to a user on how to laterally or axially position the implantable lead at the target stimulation region via a graphical user interface of the integrated clinician programmer.

26. The method of claim 25, further comprising calculating a relative distance or position of each electrode to the target stimulation region based on the EMG response value associated with each electrode.

27. The method of claim 26, further comprising:
repeating the delivering test stimulations to each of the at least four electrodes of the implantable lead and recording steps after lead re-positioning to confirm the calculated EMG response value for each electrode are within a desired value range, or to confirm the maximum EMG response amplitude for each electrode are within a desired response range and the associated stimulation amplitude for each electrode is within a desired stimulation range.

28. The method of claim 27, further comprising displaying a visual image of the recorded stimulation-induced EMG motor response during each test stimulation on a graphical user interface of the integrated clinician programmer, wherein the visual image includes a waveform comprising a compound muscle action potential (CMAP).

29. The method of claim 18, wherein the least one EMG sensing electrode comprises one or more EMG sensing electrode patches that are minimally invasively positioned on a skin surface of the patient.

30. The method of claim 18, wherein the feedback of the proximity of the at least four electrodes relative the target nerve is based on a single sweep of the single test stimulation at the same stimulation amplitude level through each of the at least four neurostimulation electrodes.

* * * * *